(12) United States Patent
Cen et al.

(10) Patent No.: US 12,318,441 B2
(45) Date of Patent: Jun. 3, 2025

(54) POLYNUCLEOTIDE MOLECULES USED FOR THE PREVENTION OR TREATMENT OF HPV INFECTION RELATED DISEASES

(71) Applicants: RINUAGENE BIOTECHNOLOGY CO., LTD., Jiangsu (CN); RINUAGENE INTERNATIONAL HK LIMITED, Kowloon (CN)

(72) Inventors: Shan Cen, Suzhou (CN); Jing Wang, Suzhou (CN); Weiguo Zhang, Suzhou (CN); Yijie Dong, Suzhou (CN)

(73) Assignees: RINUAGENE BIOTECHNOLOGY CO., LTD., Suzhou (CN); RINUAGENE INTERNATIONAL HK LIMITED, Hong Kong (CN)

( * ) Notice: Subject to any disclaimer, the term of this patent is extended or adjusted under 35 U.S.C. 154(b) by 0 days.

(21) Appl. No.: 18/770,056

(22) Filed: Jul. 11, 2024

(65) Prior Publication Data

US 2024/0358814 A1    Oct. 31, 2024

Related U.S. Application Data

(63) Continuation of application No. PCT/CN2023/142229, filed on Dec. 27, 2023.

(30) Foreign Application Priority Data

Dec. 29, 2022  (WO) ............... PCT/CN2022/143328
Dec. 8, 2023   (CN) .......................... 202311684185.8
Dec. 8, 2023   (WO) ............... PCT/CN2023/114487

(51) Int. Cl.
| | |
|---|---|
| A61K 39/12 | (2006.01) |
| A61K 9/51 | (2006.01) |
| A61K 39/39 | (2006.01) |
| A61K 39/395 | (2006.01) |
| A61P 31/20 | (2006.01) |
| A61P 35/00 | (2006.01) |
| C07K 14/005 | (2006.01) |
| A61K 39/00 | (2006.01) |

(52) U.S. Cl.
CPC ............ *A61K 39/12* (2013.01); *A61K 9/5123* (2013.01); *A61K 39/39* (2013.01); *A61K 39/3955* (2013.01); *A61P 31/20* (2018.01); *A61P 35/00* (2018.01); *C07K 14/005* (2013.01); *A61K 2039/53* (2013.01); *A61K 2039/55516* (2013.01); *C07K 2319/02* (2013.01); *C12N 2710/20022* (2013.01); *C12N 2710/20034* (2013.01)

(58) Field of Classification Search
CPC .... A61K 2039/70; A61K 39/12; A61K 39/39; A61K 2039/53; A61K 2039/55516; A61K 2039/55555; A61P 31/20; A61P 35/00; C07K 14/005; C07K 14/025; C07K 19/00; C12N 15/62
See application file for complete search history.

(56) References Cited

FOREIGN PATENT DOCUMENTS

| | | |
|---|---|---|
| CN | 105463001 A | 4/2016 |
| CN | 107073070 A | 8/2017 |
| CN | 110564751 A | 12/2019 |
| CN | 111529699 A | 8/2020 |
| CN | 112574317 A | 3/2021 |
| CN | 113941011 A | 1/2022 |
| CN | 114901360 A | 8/2022 |
| EP | 2 604 629 A1 | 6/2013 |
| WO | WO 2013/090648 A1 | 6/2013 |
| WO | WO 2014/152211 A1 | 9/2014 |
| WO | WO 2015/038892 A1 | 3/2015 |
| WO | WO 2015/164674 A1 | 10/2015 |
| WO | WO 2016/024255 A1 | 2/2016 |
| WO | WO 2016/118724 A1 | 7/2016 |
| WO | WO 2017/031232 A1 | 2/2017 |
| WO | WO 2017/049074 A1 | 3/2017 |
| WO | WO 2017/049245 A2 | 3/2017 |
| WO | WO 2017/075531 A1 | 5/2017 |
| WO | WO 2017/099823 A1 | 6/2017 |
| WO | WO 2017/112865 A1 | 6/2017 |
| WO | WO 2017/117528 A1 | 7/2017 |
| WO | WO 2017/180917 A2 | 10/2017 |
| WO | WO 2017/218704 A1 | 12/2017 |
| WO | WO 2017/223135 A1 | 12/2017 |
| WO | WO 2019/151760 A1 | 8/2019 |
| WO | WO 2021/123332 A1 | 6/2021 |

OTHER PUBLICATIONS

China National Intellectual Property Administration, International Search Report in International Application No. PCT/CN2023/142229 (Apr. 10, 2024).

*Primary Examiner* — Bao Q Li
(74) *Attorney, Agent, or Firm* — Leydig, Voit & Mayer, Ltd.

(57) ABSTRACT

The present application relates to a polynucleotide molecule that can be used for preventing or treatment HPV infection-related diseases, and a pharmaceutical product, a pharmaceutical composition, or an mRNA vaccine comprising said polynucleotide.

25 Claims, 15 Drawing Sheets
Specification includes a Sequence Listing.

```
                              SEQUENCE LISTING

Sequence total quantity: 54
SEQ ID NO: 1                  moltype = AA   length = 85
FEATURE                       Location/Qualifiers
source                        1..85
                              mol_type = protein
                              organism = synthetic construct
SEQUENCE: 1
MHQKRTAMFQ DPQERPRKLP HLCTELQTTI HDIILECVYC KQQLLRREVY DFAFRDLCIV   60
YRDGNPYAVC DKCLKFYSKI SEYRY                                        85

SEQ ID NO: 2                  moltype = AA   length = 65
FEATURE                       Location/Qualifiers
source                        1..65
                              mol_type = protein
                              organism = synthetic construct
SEQUENCE: 2
MHGDTPTLHE YMLDLQPETT DLYCYEQLND SSEEEDEIDG PAGQAEPDRA HYNIVTFCCK   60
CDSTL                                                              65

SEQ ID NO: 3                  moltype = AA   length = 88
FEATURE                       Location/Qualifiers
source                        1..88
                              mol_type = protein
                              organism = synthetic construct
SEQUENCE: 3
DKCLKFYSKI SEYRYYCYSV YGTTLEQQYN KPLCDLLIRC INCQKPLCPE EKQRHLDKKQ   60
RFHNIRGRWT GRCMSCCRSS RTRRETQL                                     88

SEQ ID NO: 4                  moltype = AA   length = 48
FEATURE                       Location/Qualifiers
source                        1..48
                              mol_type = protein
                              organism = synthetic construct
SEQUENCE: 4
HYNIVTFCCK CDSTLRLCVQ STHVDIRTLE DLLMGTLGIV CPICSQKP                48

SEQ ID NO: 5                  moltype = AA   length = 85
FEATURE                       Location/Qualifiers
source                        1..85
                              mol_type = protein
                              organism = synthetic construct
SEQUENCE: 5
MARFEDPTRR PYKLPDLCTE LNTSLQDIEI TCVYCKTVLE LTEVFEFAFK DLFVVYRDSI   60
PHAACHKCID FYSRIRELRY YSDSV                                        85

SEQ ID NO: 6                  moltype = AA   length = 65
FEATURE                       Location/Qualifiers
source                        1..65
                              mol_type = protein
                              organism = synthetic construct
SEQUENCE: 6
MYGPKATLQD IVLHLEPQNE IPVDLLCHEQ LSDSEEENDE IDGVNHQHLP ARRAEPQRHT   60
MLCMC                                                              65

SEQ ID NO: 7                  moltype = AA   length = 88
FEATURE                       Location/Qualifiers
source                        1..88
                              mol_type = protein
                              organism = synthetic construct
SEQUENCE: 7
FYSRIRELRY YSDSVYGDTL EKLTNTGLYN LLIRCLRCQK PLNPAEKLRH LNEKRRFHKI   60
```

```
AGHYRGQCHS CCNRARQERL QRRRETQV                                            88

SEQ ID NO: 8            moltype = AA   length = 55
FEATURE                 Location/Qualifiers
source                  1..55
                        mol_type = protein
                        organism = synthetic construct
SEQUENCE: 8
ARRAEPQRHT MLCMCCKCEA RIELVVESSA DDLRAFQQLF LSTLSFVCPW CASQQ              55

SEQ ID NO: 9            moltype = AA   length = 306
FEATURE                 Location/Qualifiers
source                  1..306
                        mol_type = protein
                        organism = synthetic construct
SEQUENCE: 9
MNVCQDKILE HYENDSKDIL EHYENDSKDL CDHICDHIDY WKHIRLECAI MYKARIRLEC         60
AIMYKAREMG FHQFDGDICN TMHYTNWIYI CEDAQCTVVE GQVDKKWEVH AGGGQVILCPE        120
SGQRRIKRPR SENCHPNKLL ILKCLRYRFK KHCKLSSTWH WTCHDGKHKW HWTCHDGKHK         180
NAIVTLTYDH IDYWKAIRQE NAIFFAARHQ VVPALNICKA KACKAIEWNT EPKHCFKKGG         240
QHIEVWFDYV AWDSVYYCGD DGWCKTEAEK YGCKGTWEVH FGNSIDCNDS MCSTFDDNVS         300
ATELVK                                                                   306

SEQ ID NO: 10           moltype = AA   length = 163
FEATURE                 Location/Qualifiers
source                  1..163
                        mol_type = protein
                        organism = synthetic construct
SEQUENCE: 10
ITQDCSFQHS PISSDFAVKI RELSDYLLQD YPVTVASNLQ DEELCGGLWR LVLAQRWMER         60
LKTVAGSKMQ GLLERVNTEI HFVTKCAFQP PPSCLRFVQT NISRLLQETS EQLVALKPWI        120
TRQNFSRCLE LQCQPDSSTL PPPWSPRPLE ATAPTAPGGG SGD                          163

SEQ ID NO: 11           moltype = AA   length = 23
FEATURE                 Location/Qualifiers
source                  1..23
                        mol_type = protein
                        organism = synthetic construct
SEQUENCE: 11
MDAMKRGLCC VLLLCGAVFV SPS                                                23

SEQ ID NO: 12           moltype = AA   length = 579
FEATURE                 Location/Qualifiers
source                  1..579
                        mol_type = protein
                        organism = synthetic construct
SEQUENCE: 12
MHQKRTAMFQ DPQERPRKLP HLCTELQTTI HDIILECVYC KQQLLRREVY DFAFRDLCIV         60
YRDGNPYAVC DKCLKFYSKI SEYRYMHGDT PTLHEYMLDL QPETTDLYCY EQLNDSSEEE        120
DEIDGPAGQA EPDRAHYNIV TFCCKCDSTL DKCLKFYSKI SEYRYYCYSV YGTTLEQQYN        180
KPLCDLLIRC INCQKPLCPE EKQRHLDKKQ RFHNIRGRWT GRCMSCCRSS RTRRETQLHY        240
NIVTFCCKCD STLRLCVQST HVDIRTLEDL LMGTLGIVCP ICSQKPMARF EDPTRRPYKL        300
PDLCTELNTS LQDIEITCVY CKTVLELTEV FEFAFKDLFV VYRDSIPHAA CHKCIDFYSR        360
IRELRYYSDS VMYGPKATLQ DIVLHLEPQN EIPVDLLCHE QLSDSEEEND EIDGVNHQHL        420
PARRAEPQRH TMLCMCFYSR IRELRYYSDS VYGDTLEKLT NTGLYNLLIR CLRCQKPLNP        480
AEKLRHLNEK RRFHKIAGHY RGQCHSCCNR ARQERLQRRR ETQVARRAEP QRHTMLCMCC        540
KCEARIELVV ESSADDLRAF QQLFLSTLSF VCPWCASQQ                               579

SEQ ID NO: 13           moltype = AA   length = 579
FEATURE                 Location/Qualifiers
source                  1..579
                        mol_type = protein
                        organism = synthetic construct
SEQUENCE: 13
MARFEDPTRR PYKLPDLCTE LNTSLQDIEI TCVYCKTVLE LTEVFEFAFK DLFVVYRDSI         60
PHAACHKCID FYSRIRELRY YSDSVMYGPK ATLQDIVLHL EPQNEIPVDL LCHEQLSDSE        120
EENDEIDGVN HQHLPARRAE PQRHTMLCMC FYSRIRELRY YSDSVYGDTL EKLTNTGLYN        180
LLIRCLRCQK PLNPAEKLRH LNEKRRFHKI AGHYRGQCHS CCNRARQERL QRRRETQVAR        240
RAEPQRHTML CMCCKCEARI ELVVESSADD LRAFQQLFLS TLSFVCPWCA SQQMHQKRTA        300
MFQDPQERPR KLPHLCTELQ TTIHDIILEC VYCKQQLLRR EVYDFAFRDL CIVYRDGNPY        360
AVCDKCLKFY SKISEYRYMH GDTPTLHEYM LDLQPETTDL YCYEQLNDSS EEEDEIDGPA        420
GQAEPDRAHY NIVTFCCKCD STLDKCLKFY SKISEYRYYC YSVYGTTLEQ QYNKPLCDLL        480
IRCINCQKPL CPEEKQRHLD KKQRFHNIRG RWTGRCMSCC RSSRTRRETQ LHYNIVTFCC        540
KCDSTLRLCV QSTHVDIRTL EDLLMGTLGI VCPICSQKP                              579

SEQ ID NO: 14           moltype = AA   length = 591
FEATURE                 Location/Qualifiers
source                  1..591
                        mol_type = protein
```

```
                      organism = synthetic construct
SEQUENCE: 14
MHQKRTAMFQ DPQERPRKLP HLCTELQTTI HDIILECVYC KQQLLRREVY DFAFRDLCIV    60
YRDGNPYAVC DKCLKFYSKI SEYRYAAMHG DTPTLHEYML DLQPETTDLY CYEQLNDSSE   120
EEDEIDGPAG QAEPDRAHYN IVTFCCKCDS TLAADKCLKF YSKISEYRYY CYSVYGTTLE   180
QQYNKPLCDL LIRCINCQKP LCPEEKQRHL DKKQRFHNIR GRWTGRCMSC CRSSRTRRET   240
QLAAHYNIVT FCCKCDSTLR LCVQSTHVDI RTLEDLLMGT LGIVCPICSQ KPMARFEDPT   300
RRPYKLPDLC TELNTSLQDI EITCVYCKTV LELTEVFEFA FKDLFVVYRD SIPHAACHKC   360
IDFYSRIREL RYYSDSVAAM YGPKATLQDI VLHLEPQNEI PVDLLCHEQL SDSEEENDEI   420
DGVNHQHLPA RRAEPQRHTM LCMCAAFYSR IRELRYYSDS VYGDTLEKLT NTGLYNLLIR   480
CLRCQKPLNP AEKLRHLNEK RRFHKIAGHY RGQCHSCCNR ARQERLQRRR ETQVAAARRA   540
EPQRHTMLCM CCKCEARIEL VVESSADDLR AFQQLFLSTL SFVCPWCASQ Q           591

SEQ ID NO: 15           moltype = AA  length = 885
FEATURE                 Location/Qualifiers
source                  1..885
                        mol_type = protein
                        organism = synthetic construct
SEQUENCE: 15
MNVCQDKILE HYENDSKDIL EHYENDSKDL CDHICDHIDY WKHIRLECAI MYKARIRLEC    60
AIMYKAREMG FHQFDGDICN TMHYTNWIYI CEDAQCTVVE GQVDKKWEVH AGGQVILCPE   120
SGQRRIKRPR SENCHPNKLL ILKCLRYRFK KHCKLSSTWH WTCHDGKHKW HWTCHDGKHK   180
NAIVTLTYDH IDYWKAIRQE NAIFFAARHQ VVPALNICKA KACKAIEWNT EPKHCFKKGG   240
QHIEVWFDYV AWDSVYYCGD DGWCKTEAEK YGCKGTWEVH FGNSIDCNDS MCSTFDDNVS   300
ATELVKMHQK RTAMFQDPQE RPRKLPHLCT ELQTTIHDII LECVYCKQQL LRREVYDFAF   360
RDLCIVYRDG NPYAVCDKCL KFYSKISEYR YMHGDTPTLH EYMLDLQPET TDLYCYEQLN   420
DSSEEEDEID GPAGQAEPDR AHYNIVTFCC KCDSTLDKCL KFYSKISEYR YYCYSVYGTT   480
LEQQYNKPLC DLLIRCINCQ KPLCPEEKQR HLDKKQRFHN IRGRWTGRCM SCCRSSRTRR   540
ETQLHYNIVT FCCKCDSTLR LCVQSTHVDI RTLEDLLMGT LGIVCPICSQ KPMARFEDPT   600
RRPYKLPDLC TELNTSLQDI EITCVYCKTV LELTEVFEFA FKDLFVVYRD SIPHAACHKC   660
IDFYSRIREL RYYSDSVMYG PKATLQDIVL HLEPQNEIPV DLLCHEQLSD SEEENDEIDG   720
VNHQHLPARR AEPQRHTMLC MCFYSRIREL RYYSDSVYGD TLEKLTNTGL YNLLIRCLRC   780
QKPLNPAEKL RHLNEKRRFH KIAGHYRGQC HSCCNRARQE RLQRRRETQV ARRAEPQRHT   840
MLCMCCKCEA RIELVVESSA DDLRAFQQLF LSTLSFVCPW CASQQ                  885

SEQ ID NO: 16           moltype = AA  length = 885
FEATURE                 Location/Qualifiers
source                  1..885
                        mol_type = protein
                        organism = synthetic construct
SEQUENCE: 16
MNVCQDKILE HYENDSKDIL EHYENDSKDL CDHICDHIDY WKHIRLECAI MYKARIRLEC    60
AIMYKAREMG FHQFDGDICN TMHYTNWIYI CEDAQCTVVE GQVDKKWEVH AGGQVILCPE   120
SGQRRIKRPR SENCHPNKLL ILKCLRYRFK KHCKLSSTWH WTCHDGKHKW HWTCHDGKHK   180
NAIVTLTYDH IDYWKAIRQE NAIFFAARHQ VVPALNICKA KACKAIEWNT EPKHCFKKGG   240
QHIEVWFDYV AWDSVYYCGD DGWCKTEAEK YGCKGTWEVH FGNSIDCNDS MCSTFDDNVS   300
ATELVKMARF EDPTRRPYKL PDLCTELNTS LQDIEITCVY CKTVLELTEV FEFAFKDLFV   360
VYRDSIPHAA CHKCIDFYSR IRELRYYSDS VMYGPKATLQ DIVLHLEPQN EIPVDLLCHE   420
QLSDSEEEND EIDGVNHQHL PARRAEPQRH TMLCMCFYSR IRELRYYSDS VYGDTLEKLT   480
NTGLYNLLIR CLRCQKPLNP AEKLRHLNEK RRFHKIAGHY RGQCHSCCNR ARQERLQRRR   540
ETQVARRAEP QRHTMLCMCC KCEARIELVV ESSADDLRAF QQLFLSTLSF VCPWCASQQM   600
HQKRTAMFQD PQERPRKLPH LCTELQTTIH DIILECVYCK QQLLRREVYD FAFRDLCIVY   660
RDGNPYAVCD KCLKFYSKIS EYRYMHGDTP TLHEYMLDLQ PETTDLYCYE QLNDSSEEED   720
EIDGPAGQAE PDRAHYNIVT FCCKCDSTLD KCLKFYSKIS EYRYYCYSVY GTTLEQQYNK   780
PLCDLLIRCI NCQKPLCPEE KQRHLDKKQR FHNIRGRWTG RCMSCCRSSR TRRETQLHYN   840
IVTFCCKCDS TLRLCVQSTH VDIRTLEDLL MGTLGIVCPI CSQKP                  885

SEQ ID NO: 17           moltype = AA  length = 765
FEATURE                 Location/Qualifiers
source                  1..765
                        mol_type = protein
                        organism = synthetic construct
SEQUENCE: 17
MDAMKRGLCC VLLLCGAVFV SPSITQDCSF QHSPISSDFA VKIRELSDYL LQDYPVTVAS    60
NLQDEELCGG LWRLVLAQRW MERLKTVAGS KMQGLLERVN TEIHFVTKCA FQPPPSCLRF   120
VQTNISRLLQ ETSEQLVALK PWITRQNFSR CLELQCQPDS STLPPPWSPR PLEATAPTAP   180
GGGSGDMHQK RTAMFQDPQE RPRKLPHLCT ELQTTIHDII LECVYCKQQL LRREVYDFAF   240
RDLCIVYRDG NPYAVCDKCL KFYSKISEYR YMHGDTPTLH EYMLDLQPET TDLYCYEQLN   300
DSSEEEDEID GPAGQAEPDR AHYNIVTFCC KCDSTLDKCL KFYSKISEYR YYCYSVYGTT   360
LEQQYNKPLC DLLIRCINCQ KPLCPEEKQR HLDKKQRFHN IRGRWTGRCM SCCRSSRTRR   420
ETQLHYNIVT FCCKCDSTLR LCVQSTHVDI RTLEDLLMGT LGIVCPICSQ KPMARFEDPT   480
RRPYKLPDLC TELNTSLQDI EITCVYCKTV LELTEVFEFA FKDLFVVYRD SIPHAACHKC   540
IDFYSRIREL RYYSDSVMYG PKATLQDIVL HLEPQNEIPV DLLCHEQLSD SEEENDEIDG   600
VNHQHLPARR AEPQRHTMLC MCFYSRIREL RYYSDSVYGD TLEKLTNTGL YNLLIRCLRC   660
QKPLNPAEKL RHLNEKRRFH KIAGHYRGQC HSCCNRARQE RLQRRRETQV ARRAEPQRHT   720
MLCMCCKCEA RIELVVESSA DDLRAFQQLF LSTLSFVCPW CASQQ                  765

SEQ ID NO: 18           moltype = AA  length = 765
FEATURE                 Location/Qualifiers
```

| source | 1..765 |
| | mol_type = protein |
| | organism = synthetic construct |

SEQUENCE: 18

```
MDAMKRGLCC VLLLCGAVFV SPSITQDCSF QHSPISSDFA VKIRELSDYL LQDYPVTVAS  60
NLQDEELCGG LWRLVLAQRW MERLKTVAGS KMQGLLERVN TEIHFVTKCA FQPPPSCLRF 120
VQTNISRLLQ ETSEQLVALK PWITRQNFSR CLELQCQPDS STLPPPWSPR PLEATAPTAP 180
GGGSGDMARF EDPTRRPYKL PDLCTELNTS LQDIEITCVY CKTVLELTEV FEFAFKDLFV 240
VYRDSIPHAA CHKCIDFYSR IRELRYYSDS VMYGPKATLQ DIVLHLEPQN EIPVDLLCHE 300
QLSDSEEEND EIDGVNHQHL PARRAEPQRH TMLCMCFYSR IRELRYYSDS VYGDTLEKLT 360
NTGLYNLLIR CLRCQKPLNP AEKLRHLNEK RRFHKIAGHY RGQCHSCCNR ARQERLQRRR 420
ETQVARRAEP QRHTMLCMCC KCEARIELVV ESSADDLRAF QQLFLSTLSF VCPWCASQQM 480
HQKRTAMFQD PQERPRKLPH LCTELQTTIH DIILECVYCK QQLLRREVYD FAFRDLCIVY 540
RDGNPYAVCD KCLKFYSKIS EYRYMHGDTP TLHEYMLDLQ PETTDLYCYE QLNDSSEEED 600
EIDGPAGQAE PDRAHYNIVT FCCKCDSTLD KCLKFYSKIS EYRYYCYSVY GTTLEQQYNK 660
PLCDLLIRCI NCQKPLCPEE KQRHLDKKQR FHNIRGRWTG RCMSCCRSSR TRRETQLHYN 720
IVTFCCKCDS TLRLCVQSTH VDIRTLEDLL MGTLGIVCPI CSQKP              765
```

| SEQ ID NO: 19 | moltype = AA   length = 777 |
| FEATURE | Location/Qualifiers |
| source | 1..777 |
| | mol_type = protein |
| | organism = synthetic construct |

SEQUENCE: 19

```
MDAMKRGLCC VLLLCGAVFV SPSITQDCSF QHSPISSDFA VKIRELSDYL LQDYPVTVAS  60
NLQDEELCGG LWRLVLAQRW MERLKTVAGS KMQGLLERVN TEIHFVTKCA FQPPPSCLRF 120
VQTNISRLLQ ETSEQLVALK PWITRQNFSR CLELQCQPDS STLPPPWSPR PLEATAPTAP 180
GGGSGDMHQK RTAMFQDPQE RPRKLPHLCT ELQTTIHDII LECVYCKQQL LRREVYDFAF 240
RDLCIVYRDG NPYAVCDKCL KFYSKISEYR YAAMHGDTPT LHEYMLDLQP ETTDLYCYEQ 300
LNDSSEEEDE IDGPAGQAEP DRAHYNIVTF CCKCDSTLAA DKCLKFYSKI SEYRYYCYSV 360
YGTTLEQQYN KPLCDLLIRC INCQKPLCPE EKQRHLDKKQ RFHNIRGRWT GRCMSCCRSS 420
RTRRETQLAA HYNIVTFCCK CDSTLRLCVQ STHVDIRTLE DLLMGTLGIV CPICSQKPMA 480
RFEDPTRRPY KLPDLCTELN TSLQDIEITC VYCKTVLELT EVFEFAFKDL FVVYRDSIPH 540
AACHKCIDFY SRIRELRYYS DSVAAMYGPK ATLQDIVLHL EPQNEIPVDL LCHEQLSDSE 600
EENDEIDGVN HQHLPARRAE PQRHTMLCMC AAFYSRIREL RYYSDSVYGD TLEKLTNTGL 660
YNLLIRCLRC QKPLNPAEKL RHLNEKRRPH KIAGHYRGQC HSCCNRARQE RLQRRRETQV 720
AAAARRAEPQ RHTMLCMCCK CEARIELVVES SADDLRAFQQ LFLSTLSFVC PWCASQQ    777
```

| SEQ ID NO: 20 | moltype = AA   length = 1071 |
| FEATURE | Location/Qualifiers |
| source | 1..1071 |
| | mol_type = protein |
| | organism = synthetic construct |

SEQUENCE: 20

```
MDAMKRGLCC VLLLCGAVFV SPSITQDCSF QHSPISSDFA VKIRELSDYL LQDYPVTVAS  60
NLQDEELCGG LWRLVLAQRW MERLKTVAGS KMQGLLERVN TEIHFVTKCA FQPPPSCLRF 120
VQTNISRLLQ ETSEQLVALK PWITRQNFSR CLELQCQPDS STLPPPWSPR PLEATAPTAP 180
GGGSGDMNVC QDKILEHYEN DSKDILEHYE NDSKDLCDHI CDHIDYWKHI RLECAIMYKA 240
RIRLECAIMY KAREMGFHQF DGDICNTMHY TNWIYICEDA QCTVVEGQVD KKWEVHAGGQ 300
VILCPESGQR RIKRPRSENC HPNKLLILKC LRYRFKKHCK LSSTWHWTCH DGKHKWHWTC 360
HDGKHKNAIV TLTYDHIDYW KAIRQENAIF FAARHQVVPA LNICKAKACK AIEWNTEPKH 420
CFKKGGQHIE VWFDYVAWDS VYYCGDDGWC KTEAEKYGCK GTWEVHFGNS IDCNDSMCST 480
FDDNVSATEL VKMHQKRTAM FQDPQERPRK LPHLCTELQT TIHDIILECV YCKQQLLRRE 540
VYDFAFRDLC IVYRDGNPYA VCDKCLKFYS KISEYRYMHG DTPTLHEYML DLQPETTDLY 600
CYEQLNDSSE EEDEIDGPAG QAEPDRAHYN IVTFCCKCDS TLDKCLKFYS KISEYRYYCY 660
SVYGTTLEQQ YNKPLCDLLI RCINCQKPLC PEEKQRHLDK KQRFHNIRGR WTGRCMSCCR 720
SSRTRRETQL HYNIVTFCCK CDSTLRLCVQ STHVDIRTLE DLLMGTLGIV CPICSQKPMA 780
RFEDPTRRPY KLPDLCTELN TSLQDIEITC VYCKTVLELT EVFEFAFKDL FVVYRDSIPH 840
AACHKCIDFY SRIRELRYYS DSVMYGPKAT LQDIVLHLEP QNEIPVDLLC HEQLSDSEEE 900
NDEIDGVNHQ HLPARRAEPQ RHTMLCMCFY SRIRELRYYS DSVYGDTLEK LTNTGLYNLL 960
IRCLRCQKPL NPAEKLRHLN EKRRFHKIAG HYRGQCHSCC NRARQERLQR RRETQVARRA 1020
EPQRHTMLCM CCKCEARIEL VVESSADDLR AFQQLFLSTL SFVCPWCASQ Q         1071
```

| SEQ ID NO: 21 | moltype = AA   length = 1071 |
| FEATURE | Location/Qualifiers |
| source | 1..1071 |
| | mol_type = protein |
| | organism = synthetic construct |

SEQUENCE: 21

```
MDAMKRGLCC VLLLCGAVFV SPSITQDCSF QHSPISSDFA VKIRELSDYL LQDYPVTVAS  60
NLQDEELCGG LWRLVLAQRW MERLKTVAGS KMQGLLERVN TEIHFVTKCA FQPPPSCLRF 120
VQTNISRLLQ ETSEQLVALK PWITRQNFSR CLELQCQPDS STLPPPWSPR PLEATAPTAP 180
GGGSGDMNVC QDKILEHYEN DSKDILEHYE NDSKDLCDHI CDHIDYWKHI RLECAIMYKA 240
RIRLECAIMY KAREMGFHQF DGDICNTMHY TNWIYICEDA QCTVVEGQVD KKWEVHAGGQ 300
VILCPESGQR RIKRPRSENC HPNKLLILKC LRYRFKKHCK LSSTWHWTCH DGKHKWHWTC 360
HDGKHKNAIV TLTYDHIDYW KAIRQENAIF FAARHQVVPA LNICKAKACK AIEWNTEPKH 420
CFKKGGQHIE VWFDYVAWDS VYYCGDDGWC KTEAEKYGCK GTWEVHFGNS IDCNDSMCST 480
FDDNVSATEL VKMARFEDPT RRPYKLPDLC TELNTSLQDI EITCVYCKTV LELTEVFEFA 540
FKDLFVVYRD SIPHAACHKC IDFYSRIREL RYYSDSVMYG PKATLQDIVL HLEPQNEIPV 600
```

```
DLLCHEQLSD SEEENDEIDG VNHQHLPARR AEPQRHTMLC MCFYSRIREL RYYSDSVYGD  660
TLEKLTNTGL YNLLIRCLRC QKPLNPAEKL RHLNEKRRFH KIAGHYRGQC HSCCNRARQE  720
RLQRRRETQV ARRAEPQRHT MLCMCCKCEA RIELVVESSA DDLRAFQQLF LSTLSFVCPW  780
CASQQMHQKR TAMFQDPQER PRKLPHLCTE LQTTIHDIIL ECVYCKQQLL RREVYDFAFR  840
DLCIVYRDGN PYAVCDKCLK FYSKISEYRY MHGDTPTLMY YMLDLQPETT DLYCYEQLND  900
SSEEEDEIDG PAGQAEPDRA HYNIVTFCCK CDSTLDKCLK FYSKISEYRY YCYSVYGTTL  960
EQQYNKPLCD LLIRCINCQK PLCPEEKQRH LDKKQRFHNI RGRWTGRCMS CCRSSRTRRE 1020
TQLHYNIVTF CCKCDSTLRL CVQSTHVDIR TLEDLLMGTL GIVCPICSQK P          1071

SEQ ID NO: 22           moltype = RNA   length = 50
FEATURE                 Location/Qualifiers
source                  1..50
                        mol_type = other RNA
                        organism = synthetic construct
SEQUENCE: 22
acatttgctt ctgacacaac tgtgttcact agcaacctca aacagacacc             50

SEQ ID NO: 23           moltype = RNA   length = 214
FEATURE                 Location/Qualifiers
source                  1..214
                        mol_type = other RNA
                        organism = synthetic construct
SEQUENCE: 23
gctcgctttc ttgctgtcca atttctatta aaggttcctt tgttccctaa gtccaactac  60
taaactgggg gatattatga agggccttga gcatctggat tctgcctgct cgcttttctt 120
ctgtccaatt tctattaaag gttcctttgt tccctaagtc caactactaa actgggggat 180
attatgaagg gccttgagca tctggattct gcct                             214

SEQ ID NO: 24           moltype = RNA   length = 130
FEATURE                 Location/Qualifiers
source                  1..130
                        mol_type = other RNA
                        organism = synthetic construct
SEQUENCE: 24
aaaaaaaaaa aaaaaaaaaa aaaaaaaaaa aaaaaaaaaa aaaaaaaaaa aaaaaaaaaa  60
gcatatgact aaaaaaaaaa aaaaaaaaaa aaaaaaaaaa aaaaaaaaaa aaaaaaaaaa 120
aaaaaaaaaa                                                        130

SEQ ID NO: 25           moltype = RNA   length = 37
FEATURE                 Location/Qualifiers
source                  1..37
                        mol_type = other RNA
                        organism = synthetic construct
SEQUENCE: 25
actcttctgg tccccacaga ctcagagaga acccacc                           37

SEQ ID NO: 26           moltype = RNA   length = 110
FEATURE                 Location/Qualifiers
source                  1..110
                        mol_type = other RNA
                        organism = synthetic construct
SEQUENCE: 26
gctggagcct cggtggccat gcttcttgcc ccttgggcct cccccagcc cctcctcccc   60
ttcctgcacc cgtaccccg tggtctttga ataaagtctg agtgggcggc              110

SEQ ID NO: 27           moltype = RNA   length = 123
FEATURE                 Location/Qualifiers
source                  1..123
                        mol_type = other RNA
                        organism = synthetic construct
SEQUENCE: 27
aaaaaaaaaa aaaaaaaaaa aaaaaaaaaa aaaaaaaaaa aaaaaaaaaa aaaaaaaaaa  60
gatatcaaaa aaaaaaaaaa aaaagaaaa aaaaaaaaaa aaaagaaaa aaaaaaaaaa   120
aaa                                                               123

SEQ ID NO: 28           moltype = RNA   length = 69
FEATURE                 Location/Qualifiers
source                  1..69
                        mol_type = other RNA
                        organism = synthetic construct
SEQUENCE: 28
atggacgcca tgaagcgcgg tctttgctgc gtcctgctgt tatgcggcgc tgtgttcgtc  60
agccctagc                                                          69

SEQ ID NO: 29           moltype = RNA   length = 489
FEATURE                 Location/Qualifiers
source                  1..489
                        mol_type = other RNA
                        organism = synthetic construct
```

```
SEQUENCE: 29
ataacgcagg actgcagctt ccagcacagc cctatatctt cggacttcgc ggtcaagatt      60
cgggagctct ccgactatct gctccaggac tatcccgtca cggtcgccag caaccttcag     120
gacgaagagt tgtgtggcgg cctgtggcgg ttagtcctgg cgcagcgttg gatggagcgc     180
ctgaagaccg tggctggttc gaagatgcag ggcttgctgg agcgggtgaa cacggagatt     240
cacttcgtga ccaagtgcgc gtttcagcct ccgccgagct gtctgaggtt cgtgcaacg      300
aacatcagtc ggctcttgca ggagactagc gagcagttgg tcgcgttgaa gccgtggatc     360
acccgccaga acttctcacg ttgccttgag ctgcagtgcc agccggattc ctcgaccctc     420
cctccgccgt ggtcgccgcg gccgctggag gccacgcgc ccacggcgcc tggcggcggg      480
agcggagat                                                             489

SEQ ID NO: 30            moltype = RNA    length = 255
FEATURE                  Location/Qualifiers
source                   1..255
                         mol_type = other RNA
                         organism = synthetic construct
SEQUENCE: 30
atgcatcaga agagaaccgc catgttccaa gatccgcaag agagacctag aaaactccct      60
catctgtgca ccgaactgca gaccaccatc cacgacatca tcctggagtg cgtgtattgc     120
aaacaacagc tgctgagaag agaggtgtac gacttcgcct tcagagacct gtgcatcgtg     180
taccgggacg gcaatcccta cgccgtgtgc gacaagtgcc tcaagttcta tagcaagatc     240
agcgagtata gatac                                                      255

SEQ ID NO: 31            moltype = RNA    length = 195
FEATURE                  Location/Qualifiers
source                   1..195
                         mol_type = other RNA
                         organism = synthetic construct
SEQUENCE: 31
atgcacggag atacgccgac cctgcacgag tacatgctgg acctgcagcc cgagaccacc      60
gacctgtact gctacgagca gctgaacgac agcagcgaag aggaggacga gattgacggc     120
ccggccggcc aagccgagcc cgacagagcc cactacaaca tcgtgacctt ctgctgtaaa     180
tgcgatagca cactg                                                      195

SEQ ID NO: 32            moltype = RNA    length = 264
FEATURE                  Location/Qualifiers
source                   1..264
                         mol_type = other RNA
                         organism = synthetic construct
SEQUENCE: 32
gacaagtgcc tgaagttcta cagcaagatt agcgagtaca gatattactg ctactccgtg      60
tacgggacaa ccctggagca gcagtacaac aagcctctgt gcgacctgct gatccggtgt     120
attaactgtc agaagcccctt gtgtcccgag gagaagcaga cacacctgga caagaagcag    180
agattccaca acatcagagg cagatggacc ggcagatgca tgagctgctg cagaagcagc     240
agaacaagaa gagagacaca actg                                            264

SEQ ID NO: 33            moltype = RNA    length = 150
FEATURE                  Location/Qualifiers
source                   1..150
                         mol_type = other RNA
                         organism = synthetic construct
SEQUENCE: 33
cactacaata tcgtcacctt ctgctgcaag tgcgactcca cactgcggct ctgcgtgcag      60
agcacccacg tggacatcag aaccctggag gacctgctga tgggcaccct gggcatcgtg     120
tgtcccatct gcagccaaaa gccctgatga                                      150

SEQ ID NO: 34            moltype = RNA    length = 255
FEATURE                  Location/Qualifiers
source                   1..255
                         mol_type = other RNA
                         organism = synthetic construct
SEQUENCE: 34
atggcccgat tcgaagatcc cacaagaaga ccctacaagc tgcccgacct gtgcaccgag      60
ctgaacacaa gcctccaaga catcgagatt acctgcgtgt actgcaagac cgtgctgagg     120
ctgaccgagg tgttcgagtt cgccttcaag gacctgttcg tggtgtacag agacagcatc     180
ccacacgccg cctgccacaa gtgcatcgac ttctacagcc ggattcggga actgcggtac     240
tacagcgaca gcgtg                                                      255

SEQ ID NO: 35            moltype = RNA    length = 195
FEATURE                  Location/Qualifiers
source                   1..195
                         mol_type = other RNA
                         organism = synthetic construct
SEQUENCE: 35
atgtatgggc ccaaggccac cctgcaagac atcgtgctgc acctggagcc tcagaacgaa      60
ataccgtgg acctgctgtg ccatgagcaa ctgagcgaca gcgaggaaga gaatgatgag      120
atcgacggcg tgaatcatca gcacctgccc gctagaaggg ccgagccaca acggcacacc     180
atgctgtgca tgtgc                                                      195
```

| SEQ ID NO: 36 | moltype = RNA length = 264 |
| --- | --- |
| FEATURE | Location/Qualifiers |
| source | 1..264 |
| | mol_type = other RNA |
| | organism = synthetic construct |

SEQUENCE: 36
```
ttctacagca gaatcagaga actccggtat tacagcgact ccgtgtacgg agataccctc   60
gagaagctga ccaacaccgg cctgtacaat ctgctgatca gatgtctgag atgtcagaaa  120
cccttaaatc ccgccgagaa gctgagacac ctgaacgaga agagaagatt ccacaagatc  180
gccggccact acagagggca gtgccacagc tgctgcaaca gagctagaca agagagactg  240
cagagaagac gggagaccca agtg                                         264
```

| SEQ ID NO: 37 | moltype = RNA length = 165 |
| --- | --- |
| FEATURE | Location/Qualifiers |
| source | 1..165 |
| | mol_type = other RNA |
| | organism = synthetic construct |

SEQUENCE: 37
```
gctagaaggg ctgagccgca aagacatacc atgctgtgta tgtgctgcaa atgcgaggct   60
agaatcgagc tggtggtgga gagcagcgcc gacgacctga gagccttttca gcagctgttc  120
ctgagcaccc tgagcttcgt gtgtccctgg tgcgctagcc aacag                  165
```

| SEQ ID NO: 38 | moltype = RNA length = 918 |
| --- | --- |
| FEATURE | Location/Qualifiers |
| source | 1..918 |
| | mol_type = other RNA |
| | organism = synthetic construct |

SEQUENCE: 38
```
atgaacgtgt gccaggataa gatcttggag cattacgaga atgactccaa ggatatcctg   60
gagcactatg agaacgactc caaggatcta tgtgatcaca tctgtgatca catagattat  120
tggaagcaca tccggctgga gtgcgccatt atgtataagg ctcggatacg gctggaatgt  180
gctataatgt ataaagcccg tgagatgggc tttcaccagt tcgatggtga catttgtaac  240
acaatgcact atacgaactg gatatacatc tgcgaggacg cgcagtgtac ggtagttgag  300
ggtcaggtag acaagaagtg ggaggttcac gcgggtgggc aggtcatcct gccccggag   360
tccgggcagg ggaggatcaa gcgtccgcgg agtgaaaact gccaccctaa caagctactg  420
atcctcaagt gccttcgcta tcgcttcaag aagcattgca agttgtcgtc cacgtggcac  480
tggacttgcc acgacggcaa gcacaagtgg cactggacgt gccacgacgg caagcacaag  540
aacgcgatag tgacgcttac ctatgatcac atagattatt ggaaagcgat ccggcaggag  600
aatgcgatat tcttcgctgc tagacaccag gtggtgcccg cgttgaatat ctgcaaggcg  660
aaggcctgca aggccataga gtggaacaca gagccgaagc actgctttaa gaaaggcggt  720
cagcacatcg aggtctggtt cgactatgtg gcctgggact cggtctacta ttgcggcgac  780
gacggttggt gcaagaccga ggccgagaaa tacggctgca agggacgtg ggaagttcac   840
ttcgggaact ccatcgattg caacgactcc atgtgcagca cgtttgacga taacgtgtct  900
gccacggagt tggtaaag                                                918
```

| SEQ ID NO: 39 | moltype = RNA length = 1740 |
| --- | --- |
| FEATURE | Location/Qualifiers |
| source | 1..1740 |
| | mol_type = other RNA |
| | organism = synthetic construct |

SEQUENCE: 39
```
atgcaccaga agagaaccgc catgttccag gaccctcagg agagacctag gaagctgcct   60
cacctgtgta cagagctcca gacaaccatc cacgacatca tcctggagtg cgtgtactgt  120
aagcagcagc tgctgagaag agaggtgtac gacttcgcct tcagagacct gtgcatcgtg  180
tacagagacg gcaaccctta cgccgtgtgc gataagtgtc tgaagttcta ttccaaaatc  240
tccgaatata ggtacatgca cggcgacacc cctaccctgc acgagtacat gctggacctc  300
cagcctgaga ccacagacct gtactgctac gagcagctga cgacagctc tgaggaagag   360
gacgagattg acggacctgc tggccaggcc gagcctgaca gagccactca aatatcgtg   420
acattctgtt gcaaatgcga ctccacactg gacaagtgcc tgaagttcta cagcaagatc  480
tctgagtaca gatactactg ctactctgtg tacggcacca cactggagca gcagtcaacc  540
aagcctctgt gcgacctcct gatccgctgc atcaactgcc agaagcctct gtgccctgag  600
gagaagcaga gacacctgga caagaagcag cggttccaca acatcagagg cagatggacc  660
ggcaggtgca tgtcctgctg tagatcctcc agaaccagac gggagaccca gctgcactac  720
aacatcgtga ccttcctgctg caagtcgac tctaccctga gactgtgcgt gcagtctacc   780
cacgtggaca tcagaccct ggaggacctg ctgatgggca ccctgggcat cgtgtgccct   840
atctgctctc agaagcctat ggccaggttc gaggaccta ccagaagacc ctacaagctg   900
cctgacctgt gcaccgagct gaacacctct ctgcaagaca tcgagatcac ctgcgtgtac  960
tgcaagaccg tgctggagct gaccgaggtg ttcgagttcg ccttcaagt cctgttcgtg 1020
gtgtacagag acagcatccc tcacgctgcc tgccacaagt gcatcgactt ctattccagg 1080
atcagggagc tgcgctatta ctccgactct gtgatgtacg gcccaaggc caccctccag 1140
gacatcgtgc tgcacctgga gcctcagaac gagatccccg tggacctgct gtgccacgag 1200
cagctgtctc actctgaaga ggagaacgac gagatcgacg gcgtgaacca ccagcacctg 1260
cctgccagga gagctgaacc ccagcggcat accatgctgt gtatgtgctt ctactctagg 1320
atcagaggag tgaggtacta tctctgactct gtgtacgcg acacctggaggaagctgacc 1380
aacaccggcc tgtacaacct gctgatccgg tgcctgaggt gccagaagcc tctgaaccct 1440
gccgagaagc tgacacacct gaacgagaag agaagattcc acaagatcgc tggcactac 1500
agaggccagt gccactcttg ctgcaacaga gccagacagg agagactcca gcggagaagg 1560
gagacccagt ggccaggag agccgagcct cagacacca ccatgctgtg catgtgctgc 1620
aagtgcgagg ccagaatcga gctggtggtg gagagctctg ccgacgacct gagagccttc 1680
```

| | | | |
|---|---|---|---|
| cagcagctgt | tcctgtctac | cctgagcttc gtgtgcccttggtgcgcctc tcagcagtaa | 1740 |

SEQ ID NO: 40  moltype = RNA  length = 1743
FEATURE        Location/Qualifiers
source         1..1743
               mol_type = other RNA
               organism = synthetic construct
SEQUENCE: 40

| | | | | | |
|---|---|---|---|---|---|
| atggctagat | tcgaggaccc | cacaagaaga | ccctacaagc | tgcccgacct | gtgcaccgaa | 60 |
| ctgaacacaa | gcctgcaaga | catcgagatt | acctgcgtgt | attgcaagac | cgtgctggag | 120 |
| ctgaccgagg | tgttcgagtt | cgccttcaag | gacctgttcg | tggtgtacag | agatagcatc | 180 |
| ccccacgccg | cctgccacaa | gtgcatcgac | ttctatagca | gaatcagaga | actgcggtac | 240 |
| tacagcgata | gcgtgatgta | cggccccaag | gccacctcc | aagacatcgt | cctgcacctg | 300 |
| gagcctcaga | atgagatccc | cgtggacctg | ctgtgccacg | agcagctgag | cgacagcgag | 360 |
| gaagaaaacg | acgagatcga | cggcgtcaat | catcagcacc | tgcccgctag | acgggctgag | 420 |
| cctcagcggc | acaccatgct | gtgtatgtgc | ttctacagca | gaattagaga | gctcagatac | 480 |
| tacagcgaca | gcgtgtatgg | cgacacccctg | gagaagctga | ccaacaccgg | cctgtacaat | 540 |
| ctgctgatca | gatgcctgag | atgtcagaag | cccctcaacc | ccgccgagaa | gctgagacac | 600 |
| ctgaacgaga | agagaagatt | ccacaagatc | gccggccact | acagagggca | gtgccacagc | 660 |
| tgctgcaaca | gagctagaca | agagagactg | cagagacggc | gggaaaccca | gtggctaga | 720 |
| agggccgagc | tcagagaca | tacaatgctg | tgcatgtgct | gcaagtgcga | agctagaatc | 780 |
| gagctggtgg | tggagagcac | cgccgacgac | ctgagagctc | ttcagcagct | gttcctgagc | 840 |
| accctgagct | tcgtgtgccc | ctggtgcgct | agccaacaga | tgcatcagaa | gagaaccgcc | 900 |
| atgttccaag | accccaaga | gagacctaga | aagctgcccc | acctgtgtac | cgagctgcag | 960 |
| acaaccatcc | acgacatcat | cctggagtgc | gtgtactgca | agcagcaact | gctgagaaga | 1020 |
| gaggtgtacg | acttcgcctt | cagagacctg | tgcatcgtgt | agggacgg | gaatccctac | 1080 |
| gccgtgtgcg | acaaatgtct | caagttttat | agcaagatta | gcgagtacag | atacatgcac | 1140 |
| ggcgacaccc | ccacccttgca | cgagtacatg | ctggacctgc | agcccgagac | caccgacctg | 1200 |
| tactgctacg | aacaactgaa | cgacagctcc | gaggaagagg | acgaaatcga | cggccccgcc | 1260 |
| ggccaagccg | agcccgacag | agcccactac | aacattgtga | cattctgttg | caagtgtgac | 1320 |
| agcaccctgg | acaaatgcct | gaagttctac | agcaagatca | gcgagtacag | atattactgc | 1380 |
| tacagcgtgt | acggcaccac | cctggagcag | cagtacaaca | gcccctgtg | tgacctgctg | 1440 |
| attagatgca | tcaactgtca | gaagcccctg | tgccccgagg | agaagcagag | acacctggac | 1500 |
| aagaagcaga | gattccacaa | catcagaggc | agatggaccg | gcagatgcat | gagctgctgc | 1560 |
| agaagcagca | gaacaagaag | agagacacag | ctgcactaca | atatcgtgac | cttttgctgc | 1620 |
| aagtgcgata | gcaccctgcg | gctgtgcgtg | cagagcaccc | acgtggacat | cagaaccctg | 1680 |
| gaggacctgc | tgatgggcac | cctgggcatc | gtgtgcccca | tctgcagcca | aaagccctga | 1740 |
| tga | | | | | | 1743 |

SEQ ID NO: 41  moltype = RNA  length = 1743
FEATURE        Location/Qualifiers
source         1..1743
               mol_type = other RNA
               organism = synthetic construct
SEQUENCE: 41

| | | | | | |
|---|---|---|---|---|---|
| atggcgcggt | tcgaggaccc | gactcgcagg | ccgtataagt | taccggatct | ctgtacagag | 60 |
| ctgaacacgt | ccttgcagga | catcgaaatc | acctgcaagac | atgcaagac | cgtcttggag | 120 |
| ttaacggagg | tgttcgagtt | cgccttcaag | gacttgttcg | ttgtgtacag | agattcgata | 180 |
| cctcatgcgg | cctgccacaa | gtgcatcgat | ttctattcgc | gcattcgaga | gctgaggtac | 240 |
| tactcggaca | gtgtcatgta | cgggcctaag | gccacgttac | aggacattgt | cctccacctg | 300 |
| gaacctcaga | atgagattcc | ggtggacctg | tctgccatga | agcagctctc | ggactccgag | 360 |
| gaagagaacg | atgagatcga | cggagtgaac | catcagcacc | tgcccgcgag | aagggcagag | 420 |
| ccacagcgtc | acacaatgct | gtgtatgtgc | ttctactcgc | ggatcaggga | gctgaggtat | 480 |
| tactccgact | cggtctacgg | agacacctta | gagaagttga | caaacaccgg | tttgtacaac | 540 |
| cttctcataa | ggtgtctccg | ttgccaaaag | cctctgaatc | cggcggaga | gctgcggcat | 600 |
| ctcaacgaga | agcggcggtt | tcacaagatc | gccgggcact | acagaggaca | gtgccacagc | 660 |
| tgctgcaacc | cgccagaca | ggagcggttg | cagcggcggc | gcgagcccca | ggttgcccgg | 720 |
| cgagccgagc | cgcagcgaca | tacaatgctt | tgtatgtgct | gcaagtgcga | ggctcggata | 780 |
| gagcttgtcg | tggaatcttc | tgcggatgac | ctgcgagcat | tccagcagct | gtttctgagc | 840 |
| actctgtcgt | tcgtgtgccc | gtggtgcgcg | agcagcaga | tgcatcagaa | gcggactgct | 900 |
| atgttccaag | acccgcagga | gaggccacgc | aagcttccac | atctgtgtac | agagctccaa | 960 |
| accaccatcc | acgacatcat | cctggagtgc | gtgtactgca | aacagcagct | gctgagaaga | 1020 |
| gaggtgtacg | acttcgcctt | cagagacctg | tgcatcgtgt | acagagatgg | gaatccctac | 1080 |
| gccgtgtgcg | acaagtgcct | gaagttctat | agcaagatca | gcgagtacag | atacatgcat | 1140 |
| ggcgacacac | ccaccctgca | cgagtacatg | ctggacctgc | agcccgagac | caccgacctg | 1200 |
| tactgctatg | agcagctgaa | cgacagcagc | gaagaggagg | acgagatcga | cggccctgct | 1260 |
| ggccaagccg | agcccgacag | agcccactat | aacatcgtca | cattctgttg | caaatgtgac | 1320 |
| tccacccctgg | acaagtgtct | gaaattctat | agcaagatct | ccgagtaccg | gtactactgt | 1380 |
| tacagcgtgt | acggcaccac | actggagcag | cagtacaaca | gccgctttg | cgatctgctg | 1440 |
| atccggtgca | tcaactgtca | gaagcccttg | tgtcccgaag | agaagcagag | acacctggac | 1500 |
| aagaagcaga | gattccacaa | catcagaggc | agatggaccg | gcagatgcat | gagctgctgc | 1560 |
| agaagcagca | gaacccggag | agagacccaa | ctccactaca | atatcgtgac | cttctgttgc | 1620 |
| aagtgcgata | gcaccctgag | actgtgcgtg | cagagcaccc | acgtggacat | cagaaccctg | 1680 |
| gaggacctgc | tgatgggcac | cctgggcatc | gtgtgcccta | tctgcagcca | aaagccctga | 1740 |
| tga | | | | | | 1743 |

SEQ ID NO: 42  moltype = RNA  length = 1743
FEATURE        Location/Qualifiers
source         1..1743

```
                        mol_type = other RNA
                        organism = synthetic construct
SEQUENCE: 42
atggctagat tcgaggaccc cacaagaaga ccctacaagc tgcccgatct ctgcacagag    60
ctgaacacaa gcctgcaaga catcgagatc acctgcgtgt attgcaagac cgtgctggag   120
ctgaccgagg tgttcgagtt cgccttcaag gacctgttcg tggtgtacag agacagcatc   180
ccccacgccg cctgccacaa gtgcatcgac ttctacagcc ggatcagaga gctccggtac   240
tacagcgact ccgtgatgta cggccccaag gccaccctcc aagacatcgt gctgcacctg   300
gagcctcaga acgagatccc cgtggacctg ctgtgccacg agcagctgag cgacagcgag   360
gaagagaacg acgaaattga cggcgtgaac catcagcacc tgcccgctag acgggccgag   420
cctcagcggc acaccatgct gtgtatgtgc ttctacagca gaatcagaga actcagatat   480
tactccgact ccgtgtacgg cgacacactg gagaagctga ccaacaccgg cctgtacaac   540
ctgctgatca gatgcctgag atgtcagaag cctctcaatc cgccgagaa gctgagacac    600
ctgaacgaca agaaagatt ccaagatc gccggccact acagagggca gtgccacagc      660
tgctgcaaca gagctagaca agagagactg cagagaagac gggagaccca agtggctaga   720
agggccgagc tcagagaca caccatgctg tgcatgtgct gcaagtgcga agctagaatc     780
gagctggtgg tggagagcag cgccgacgac ctgagagcct tcagcagct gttcctgagc    840
accctgagct tcgtgtgccc ctggtgcgct agccaacaga tgcatcagaa ggaaccgcc    900
atgttccaag accccaaga gagacctaga aagctgcccc acctgtgtac agagctccaa   960
accaccatcc acgacatcat cctggagtgc gtgtactgca acagcagct gctgagaaga    1020
gaggtgtacg acttcgcctt cagagacctg tgcatcgtgt acagagatgg gaatccctac   1080
gccgtgtgcg acaagtgcct gaagtttat agcaagatca gcgtgtacag atacatgcat   1140
ggcgacaccc ccaccctgca cgagtacatg ctggacctgc agcccgagac caccgacctg   1200
tactgctatg agcagctgaa cgacagcagc gaagaggagg acgagatcga cggccccgct   1260
ggccaagccg agcccgacag agcccactat aacatcgtca cattctgttg caaatgtgac   1320
tccaccctgg acaagtgtct gaaattctat agcaagatct ccgagtaccg gtactactgt   1380
tacagcgtgt acggcaccac actggagcag cagtacaaca agcccctgtg cgatctgctg   1440
atccggtgca tcaactgtca gaagcccctg tgtcccgaag agaagcagag acacctggac   1500
aagaagcaga gattccacaa catcagaggc agatggaccg gcagatgcat gagctgctgc   1560
agaagcagaa gaacccggag agagacccaa ctccactaca atatcgtgac cttctgttgc   1620
aagtgcgata gcaccctgag actgtgcgtg cagagcaccc acgtggacat cagaaccctg   1680
gaggacctgc tgatgggcac cctgggcatc gtgtgcccca tctgcagcca aaagccctga   1740
tga                                                                1743

SEQ ID NO: 43          moltype = RNA    length = 1779
FEATURE                Location/Qualifiers
source                 1..1779
                       mol_type = other RNA
                       organism = synthetic construct
SEQUENCE: 43
atgcatcaga agagaaccgc catgttccaa gaccccaag agagacctag aaagctgccc    60
cacctgtgca ccgagctgca gaccaccatc cacgacatca tcctggagtg cgtgtactgt   120
aagcagtgc tgctgagaag agaggtgtac gacttcgcct tcagagacct gtgcatcgtg    180
tatagagacg gcaaccccta cgccgtgtgc gataagtgcc tgaaattcta ctccaagatc   240
agcgagtaca gatacgccgc catgcacgg gacaccccca cctgcacga gtacatgctg     300
gacctgcagc ccgagaccac cgacctgtac tgctacgagc agctgaacga cagctccgaa   360
gaggagacg agatcgacgg ccccgccggc caagccgaca ccgacagagc tcactacaat    420
atcgtgacat tctgctgcaa gtgcgactcc acactggctg ccgacaagtg cctcaagttt   480
tacagcaaga tctccgaata cagatactac tgctacagcg tgtacgggac caccctggag   540
cagcagtaca acaaacctct ctgcgacctg ctgattagat gcattaattg tcagaagccc   600
ctgtgccccg aggagaagca gagacacctg gacaagagc agagattcca caacatcaga   660
ggcagatgga ccggcagatg catgagctgc tgcagaagca gcagaacaag aagagagaca   720
cagctggccg ctcactacaa catcgtcacc ttctgttgta agtgcgactc caccctgaga   780
ctgtgcgtgc agagcaccca cgtggacatc agaaccctgg aggacctgct gatgggcacc   840
ctgggcatcg tgtgccccat ctgcagccaa aagcccatgg ctagattcga ggaccccaaa   900
agaagaccct acaagctgcc cgacctgtgt acagaactga acacaagcct gcaagacatc   960
gagatcacct gcgtgtactg caagaccgtg ctggagctga ccgaggtgtt cgagttcgcc   1020
ttcaaggacc tgttcgtggt gtacagagac agcatccccc acgccgcctg ccacaagtgc   1080
atcgacttct acagcagaat tagagaactg cggtactaca gcgacagcgt ggcgccatg    1140
tacggcccca aggccaccct ccaagacatc gtgctgcacc tcgagcctca gaacgagatc   1200
cccgtggacc tgctgtgcca cgaacagctg agcgacagcg aggaagagaa cgacgagatt   1260
gacggcgtga accatcagca cctgcccgct cggagagctg agcccaacg gcacaccatg   1320
ctgtgtatgt gtgccgcttt ctatagcaga atccgggagc tgcggtacta ttccgacagc   1380
gtgtacgggg acacactgga gaagctgacc aacaccggcc tgtacaatct gctgatcaga   1440
tgcctcagat gtcagaaacc cctcaaccct gccgagaagc tgagacacct gaacgagaag   1500
agaagattcc acaagatcgc cggccactac agagggcagt gccacagctg ctgcaacaga   1560
gctagacaag agactgca gagacggaga gagacccaag tggccgctgc tagaagggc      1620
gagcctcaga gacacacaat gctgtgcatg tgctgcaaat gcgaggctag aatcgagctg   1680
gtggtggaga gcagcgccga cgacctgaga gcctttcagc agctgttcct gagcaccctg   1740
agcttcgtgt gccctggtg cgctagccaa cagtgatga                           1779

SEQ ID NO: 44          moltype = RNA    length = 2661
FEATURE                Location/Qualifiers
source                 1..2661
                       mol_type = other RNA
                       organism = synthetic construct
SEQUENCE: 44
atgaacgtgt gccaagacaa gatcctggaa cactacgaga tgacagcaa agacattctg    60
gagcactacg aaaatgattc caaggacctg tgtgaccata tctgtgatca tatcgattat   120
```

```
tggaagcaca tcagactgga atgtgctatc atgtacaagg cccggatcag actggagtgc   180
gccatcatgt acaaggctcg ggaaatgggc ttccatcagt tcgacggcga catctgcaac   240
accatgcact acaccaactg gatctacatc tgcgaggacg ctcagtgcac cgtggtggag   300
ggccaagtgg acaagaagtg ggaggtgcac gccggcggcc aagtgatcct gtgccctgaa   360
agcggcacag aagaatcaa gagacccccg agcgagaact gccaccccaa caagctgctg   420
atcctgaagt gcctgagata cagattcaag aagcactgca agctgagcag cacctggcac   480
tggacctgcc atgatggcaa acacaagtgg cactggacct gccacgacgg caagcataag   540
aatgccatcg tgaccctgac ctacgaccac atcgattatt ggaaggccat cagacaagag   600
aacgccatct tcttcgccgc tagacaccaa gtggtgcccg ccctgaacat ctgcaaggcc   660
aaggcctgca aggccatcga gtggaacacc gagcccaagc actgcttcaa gaagggcggg   720
cagcacatcg aggtgtggtt cgactacgtc gcctgggata gcgtgtacta ctgcggcgac   780
gacggctggt gcaagaccga ggccgagaag tacggctgca agggcacctg ggaggtccac   840
ttcggcaaca gcatcgactg caacgacagc atgtgcagca ccttcgacga caacgtgagc   900
gccaccgagc tggtgaagat gatcagaag agaacccgca tgttccaaga cccccaagag   960
agacctagaa aactccccca tctgtgcacc gaactgcaga ccaccatcca cgacatcatc  1020
ctggagtgcg tgtattgcaa acaacagctg ctgagaagag aggtgtacga cttcgccttc  1080
agagacctgt gcatcgtgta ccgggacggc aatccctacg ccgtgtgcga caagtgcctc  1140
aagttttata gcaagatcag cgagtataga tacatgcacg gggacacccc caccctgcac  1200
gagtacatgc tggacctgca gcccgagacc accgacctgt actgctacga gcagctgaac  1260
gacagcagcg aagaggagga cgagattgac ggccccgccg ccaagccgga gcccgacaga  1320
gcccactaca acatcgtgac cttctgctgt aaatgcgata gcacactgga caagtgcctg  1380
aagttctaca gcaagattag cgagtacaga tattactgct actccgtgta cgggacaacc  1440
ctggagcagc agtacaacaa gcctctgtgc gacctgctga tccggtgtat taactgtcag  1500
aagcccctgt gccccgagga aagcagaga cacctggaca gaagcagag attccacaac  1560
atcagaggca gatggaccgg cagatgcatg agctgctgca aagcagcag aacaagaaga  1620
gagacacaac tgcactacaa tatcgtcacc ttctgctgca agtgcgactc cacactgcgg  1680
ctctgcgtgc agagcaccca cgtggacatc agaaccctgg aggacctgct gatgggcacc  1740
ctgggcatcg tgtgccccat ctgcagccaa aagcccatgg ctagattcga ggaccccaca  1800
agaagaccct acaagctgcc cgacctgtgc accgagctga cacaagcct ccaagacatc  1860
gagattacct gcgtgtactg caagaccgtg ctggagctga ccgaggtgtt cgagttcgcc  1920
ttcaaggacc tgttcgtggt gtacagagac agcatccccc acgccgcctg ccacaagtgc  1980
atcgacttct acagccggat cgggaactg cggtactaca gcgacagcgt gatgtatggc  2040
cccaaggcca ccctgcaaga catcgtgctg cacctggagc tcagaacga aatcccgtg  2100
gacctgctgt gccatgagca actgagcgac agcgaggaag agaatgatga gatcgacggc  2160
gtgaatcatc agcacctgcc cgctagaagg gccgagccc aacggcacac catgctgtgc  2220
atgtgcttct acagcagaat cagagaactc cggtattaca gcgactccgt gtacggggat  2280
accctcgaga agctgaccaa caccggcctg tacaatctgc tgatcagatg tctgagatgt  2340
cagaaacccc tgaacccccgc cgagaagctg agacacctga acgagaagag aagattccac  2400
aagatcgccg gccactacag agggcagtgc cacagctgct gcaacagac tagacaagag  2460
agactgcaga gaaagacggga gacccaagtg gctagaaggg ctgagcccca aagcatacc  2520
atgctgtgta tgtgctgcaa atgcgaggct agaatcgagc tggtggtgga gagcagcgcc  2580
gacgacctga gagcctttca gcagctgttc ctgagcaccc tgagcttcgt gtgcccctgg  2640
tgcgctagcc aacagtgatg a                                             2661

SEQ ID NO: 45         moltype = RNA   length = 2661
FEATURE               Location/Qualifiers
source                1..2661
                      mol_type = other RNA
                      organism = synthetic construct
SEQUENCE: 45
atgaacgtgt gccaggataa gatcttggag cattacgaga atgactccaa ggatatcctg    60
gagcactatg agaacgactc caaggatcta tgtgatcaca tctgtgatca catagattat   120
tggaagcaca tccggctgga gtgcgccatt atgtataagg cgcgtatccg gctgaatgt    180
gctataatgt ataaagcccg tgagatgggc tttcaccagt tcgatggtga catttgtaac   240
acaatgcatt atacgaactg gatatacatc tgcgaggacg cgcagtgtac ggtagttgag   300
ggtcaggtag acaagaagtg ggaggttcac gccggtgggc aggtcatcct ctgcccggag   360
tccgggcaga ggaggatcaa gcgtccgcgg agtgaaaact gccaccctaa caagctactg   420
atcctcaagt gccttcgcta tcgcttcaag aagcattgca agttgtcgtc cacgtggcac   480
tggacttgcc acgacggcaa gcacaagtgg cactggacgt gccacgacgg caagcacaag   540
aacgcgatag tgacgcttac ctatgatcac atagattatt ggaaagcgat ccggcaggag   600
aatgcgatat tcttcgctgc acgccaccag gtggtgcccg cgttgaatat ctgcaaggcg   660
aaggcctgca aggccataga gtggaacaca gagccgaagc actgctttaa gaaggcggt    720
cagcacatcg aggtctggtt cgactatgtg gcctgggact cggtctacta ttgcggcgac   780
gacggttggt gcaagaccga ggccgagaaa tacggctgca agggtacgt ggaagttcac   840
tttggtaaca gcatcgattg caacgactcc atgtgcagca cgtttgacga taacgtgtct   900
gccacggagt tggtaaagat gaccagaag cggaccgcga tgttccaaga tcctcaagag   960
agacctagaa aactcccgca tctgtgcacc gaactgcaga ccaccatcca cgacatcatc  1020
ctggagtgcg tgtattgcaa acaacagctg ctgagaagag aggtgtacga cttcgccttc  1080
agagacctgt gcatcgtgta ccgggacggc aatccctacg ccgtgtgcga caagtgcctc  1140
aagttctata gcaagatcag cgagtataga tacatgcacg gcgacacacc gaccctgcac  1200
gagtacatgc tggacctgca gcccgagacc accgacctgt actgctacga gcagctgaac  1260
gacagcagcg aagaggagga cgagattgac ggccctgccg ccaagccgga gcccgacaga  1320
gcccactaca acatcgtgac cttctgctgt aaatgcgata gcacactgga caagtgcctg  1380
aagttctaca gcaagattag cgagtacaga tattactgct actccgtgta cgggacaacc  1440
ctggagcagc agtacaacaa gcctctgtgc gacctgctga tccggtgtat taactgtcag  1500
aagccactgt gccctgagga aagcagaga cacctggaca gaagcagag attccacaac  1560
atcagaggca gatggaccgg cagatgcatg agctgctgca aagcagcag aacaagaaga  1620
gagacacaac tgcactacaa tatcgtcacc ttctgctgca agtgcgactc cacactgcgg  1680
ctctgcgtgc agagcaccca cgtggacatc agaaccctgg aggacctgct gatgggcacc  1740
```

```
ctgggcatcg tgtgcccgat ctgcagccaa aagcccatgg ctagatttga agatcccaca   1800
agaagaccct acaagctgcc cgacctgtgc accgagctga acacaagcct ccaagacatc   1860
gagattacct gcgtgtactg caagaccgtg ctggagctga ccgaggtgtt cgagttcgcc   1920
ttcaaggacc tgttcgtggt gtacagagac agcattcctc acgccgcctg ccacaagtgc   1980
atcgacttct acagccggat tcgggaactg cggtactaca gcgacagcgt gatgtatggc   2040
ccgaaggcca ccctgcaaga catcgtgctg cacctggagc ctcagaacga aatacccgtg   2100
gacctgctgt gccatgagca actgagcgac agcgaggaag agaatgatga gatcgacggc   2160
gtgaatcatc agcacctgcc cgctagaagg gccgagccgc aacggcacac catgctgtgc   2220
atgtgcttct acagcagaat cagagaactc cggtattaca gcgactccgt gtacggagac   2280
accctcgaga agctgaccaa caccggcctg tacaatctgc tgatcagatg tctgagatgt   2340
cagaaaccct gaatcccgc cgagaagctg agacacctga cgagaagag aagattccac   2400
aagatcgccg gccactacag agggcagtgc cacagctgct gcaacagagc tagacaagag   2460
agactgcaga gaagacggga gacccaagtg gctagaaggg ctgagcctca agacatacc    2520
atgctgtgta tgtgctgcaa atgcgaggct agaatcgagc tggtggtgga gagcagcgcc   2580
gacgacctga gagcctttca gcagctgttc ctgagcaccc tgagcttcgt gtgtccctgg   2640
tgcgctagcc aacagtgatg a                                              2661

SEQ ID NO: 46          moltype = RNA   length = 2661
FEATURE                Location/Qualifiers
source                 1..2661
                       mol_type = other RNA
                       organism = synthetic construct
SEQUENCE: 46
atgaacgtgt gccaggataa gatcttggag cattacgaga atgactccaa ggatatcctg    60
gagcactatg agaacgactc caaggatcta tgtgatcaca tctgtgatca catagattat   120
tggaagcaca tccggctgga gtgcgccatt atgtataagg ctcggatacg gctggaatgt   180
gctataatgt ataaagcccg tgagatgggc tttcaccagt tcgatggtga catttgtaac   240
acaatgcact atacgaactg gatatacatc tgcgaggacg cgcagtgtac ggtagttgag   300
ggtcaggtag acaagaagtg ggaggttcac gcggtgtggc aggtcatcct ctgcccggag   360
tccgggacga ggaggatcaa gcgtccgcgg agtgaaaact gccaccctaa caagctactg   420
atcctcaagt gccttcgcta tcgcttcaag aagcattgca agttgtcgtc cacgtggcac   480
tggacttgcc acgacggcaa gcacaagtgg cactggacgt gccacgacgg caagcacaag   540
aacgcgatag tgacgcttac ctatgatcac atagattatt ggaaagcgat ccggcaggag   600
aatgcgatat tcttcgctgc tagacaccag gtggtgcccg cgttgaatat ctgcaaggcg   660
aaggcctgca aggcctatga gtggaacaca gagccgaagc actgctttaa gaaaggcgt    720
cagcacatcg aggtctggtt cgactatgtg gcctgggact cggtctacta ttgcggcgac   780
gacggttggt gcaagaccga ggccgagaaa tacggctgca aagggacgtg ggaagttcac   840
ttcgggaact ccatcgattg caacgactcc atgtgcagca cgtttgacga taacgtgtct   900
gccacggagt tggtaaagat ggcccgattc gaagatccca caagaagacc ctacaagctg   960
cccgacctgt gcaccgagct gaacacaagc ctccaagaca tcgagattac ctgcgtgtac  1020
tgcaagaccg tgctggagct gaccgagtg ttcgagttcg ccttcaagga cctgttcgtg   1080
gtgtacagag acagcatccc acacgccgcc tgccacaagt gcatcgactt ctacagccgg  1140
attcgggaac tgcggtacta cagcgacagc gtgatgtatg ggcccaagtgc caccctgcaa  1200
gacatcgtgc tgcacctgga gcctcagaac gaaatacccg tggacctgct gtgccatgag  1260
caactgagcg acagcgagga agagaatgat gagatcgacg gcgtgaatca tcagcacctg  1320
cccgctagaa gggccgagcc acaacggcac accatgctgt gcatgtgctt ctacagcaga  1380
atcagagaac tccggtatta cagcgactcc gtgtacggag atacccctga gaagctgacc  1440
aacaccggcc tgtacaatct gctgatcaga tgtctgagat gtcagaaacc cttaaatccc   1500
gccgagaagc tgagacacct gaacgagaag agaagattcc acaagatcgc cggccactac  1560
agagggcagt gccacagctg ctgcaacaga gctagacaag agagactgca gagaagacgg  1620
gagacccaag tggctagaag gctgagccg caaagacata ccatgctgtg tatgtgctgc  1680
aaatgcgagg ctagaatcga gctggtggtg gagagcagcg ccgacgacct gagagccttt  1740
cagcagctgt tcctgagcac cctgagcttc gtgtgtccct ggtgcgctag ccaacagatg  1800
catcagaaga gaaccgccat gttccaagat ccgcaagaga gacctagaaa actccctcat  1860
ctgtcaccg aactgcagac caccatccac gacatcatcc tggagtgcgt gtattgcaaa   1920
caacagctgc tgagaagaga ggtgtacgac ttcgccttca gagacctgtg catcgtgtac  1980
cgggacggca atccctacgc cgtgtgcgac aagtgcctca gttctatag caagatcagc  2040
gagtatagat acatgcacgg agatacgccg accctgcacg agtacatgct ggacctgcag  2100
cccgagacca ccgacctgta ctgctacgag cagctgaacg acagcagcga agaggaggac  2160
gagattgacg gcccggccgg ccaagccgag cccgacagag cccactacaa catcgtgacc  2220
ttctgctgta aatgcgatag cacactggac aagtgcctga gttctacag caagattagc  2280
gagtacagat attactgcta ctccgtgtac gggacaaccc tggagcagca gtacaacaag  2340
cctctgtgcg acctgctgat ccggtgtatt aactgtcaga agcccttgtg tcccgaggag  2400
aagcagagac acctggacaa gaagcagaga ttccacaaca tcagaggcag atggaccggc  2460
agatgcatga gctgctgcag aagcagcaga acaagaagga gacacaact gcactacaat  2520
atcgtcacct tctgctgcaa gtgcgactcc acactgcggc tctgcgtgca gagcacccac  2580
gtggacatca gaaccctgga ggacctgctg atgggcaccc tgggcatcgt gtgtcccatc  2640
tgcagccaaa agccctgatg a                                              2661

SEQ ID NO: 47          moltype = RNA   length = 2298
FEATURE                Location/Qualifiers
source                 1..2298
                       mol_type = other RNA
                       organism = synthetic construct
SEQUENCE: 47
atggatgcta tgaaacgggg cctgtgctgc gtgctgctcc tgtgcggcgc gtgtttgtg      60
agccctagca tcacccagga ctgctccttc aacacagcc ccatctcctc cgacttcgct   120
gtcaaaatcc gtgagctgtc tgactacctg cttcaagatt acccagtcac cgtggcctcc  180
aacctgcagg acgaggagct ctgcggggc ctctggcgg tggtcctggc acagcgctgg  240
```

```
atggagcggc tcaagactgt cgctgggtcc aagatgcaag gcttgctgga gcgcgtgaac    300
acggagatac actttgtcac caaatgtgcc tttcagcccc ccccagctg tcttcgcttc    360
gtccagacca acatctcccg cctcctgcag gagacctccg agcagctggt ggcgctgaag    420
ccctggatca ctcgccagaa cttctcccgg tgcctggagc tgcagtgtca gcccgactcc    480
tcaaccctgc caccccatg gagtccccgg ccctgaggg ccacagcccc gacagccccg    540
ggcggcggca gcggcgatat gcaccgaaag agaaccgcca tgttccagga ccctcaggag    600
agacctagga agctgcctca cctgtgtaca gagctccaga caaccatcca cgacatcatc    660
ctggagtgcg tgtactgtaa gcagcagctg ctgagaagag aggtgtacga cttcgccttc    720
agagacctgt gcatcgtgta cagagacggc aaccctaccg ccgtgtgcga taagtgtctg    780
aagttctatt ccaaaatctc cgaatataggg tacatgcacg gcgacacccc taccctgcac    840
gagtacatgc tggacctcca gcctgagacc acagacctgt actgctacga gcagctgaac    900
gacagctctg aggaagagga cgagattgac ggacctgctg gccaggccga gcctgacaga    960
gcccactaca atatcgtgac attctgttgc aaatgcgact ccacactgga caagtgcctg    1020
aagttctaca gcaagatctc tgagtacaga tactactgct actctgtgta cggcaccaca    1080
ctggagcagc agtacaacaa gcctctgtgc gacctcctga tccgctgcat caactgccag    1140
aagcctctgt gccctgagga agcagagaca cctggaca agaagcagcg gttccacaac    1200
atcagaggca gatggaccgg caggtgcatg tcctgctgta gatcctccag aaccagacgg    1260
agacccagc tgcactacaa catcgtgacc ttctgctgca agtgcgactc tacctgaga    1320
ctgtgcgtgc agtctaccca cgtggacatc agaaccctgg aggacctgct gatgggcacc    1380
ctgggcatcg tgtgccctat ctgctctcag aagcctatgg ccaggttcga ggaccctacc    1440
agaagaccct acaagctgcc tgacctgtgc accgagctga cacctctct gcaagacatc    1500
gagatcacct gcgtgtactg caagaccgtg ctggagctga gcgaggtgt cgagttcgcc    1560
ttcaaggacc tgttcgtggt gtacagagac agcatccctc acgctgcctg ccacaagtgc    1620
atcgacttct attccaggat cagggagctg cgctattact ccgactctgt gatgtacggc    1680
cccaaggcca ccctccagga catcgtgctg cacctggagc tcagaacga gatcccgtg    1740
gacctgctgt gccacgagca gctgtctgac tctgaagagg agaaacagcg gatcgacggc    1800
gtgaaccacc agcacctgcc tgccaggaga gctgaacccc agcggcatac catgctgtgt    1860
atgtgcttct actctaggat cagagagctg aggtactact ctgactctgt gtacggcgac    1920
accctggaga agctgaccaa caccggcctg tacaacctgc tgatccggtg cctgaggtgc    1980
cagaagccctc tgaaccctgc cgagaagctg agacacctga acgagaagag aagattccac    2040
aagatcgctg gccactacag aggccagtgc cactcttgct gcaacagagc cagacaggag    2100
agactccagc ggagaaggga gacccaggtg gccaggagag ccgagcctca gagacacacc    2160
atgctgtgca tgtgctgcaa gtgcgaggcc agaatcgagc tggtggtgga gagctctgcc    2220
gacgacctga gagccttcca gcagctgttc ctgtctaccc tgagcttcgt gtgcccttgg    2280
tgcgcctctc agcagtaa                                                 2298
```

```
SEQ ID NO: 48           moltype = RNA   length = 2301
FEATURE                 Location/Qualifiers
source                  1..2301
                        mol_type = other RNA
                        organism = synthetic construct
SEQUENCE: 48
atggacgcca tgaagagagg cctgtgctgc gtgctgctcc tgtgcggcgc cgtgttcgtg    60
agccctagca tcacccaaga ctgcagcttt cagcacagcc ccatcagcag cgacttcgcc    120
gtgaagatca gagagctgag cgactacctg ctgcaagact accccgtgac cgtggctagc    180
aacctgcaag acgaggagct gtgcggcggc ctgtgggaca tggtgctggc tcagagatgg    240
atggagagac tgaagaccgt ggccgagcag aagatgcaag gcctgctggc agagtgaac    300
accgagatcc acttcgtgac caagtgcgcc tttcagcccc ctcctagctg cctgagattc    360
gtgcagacca acatcagcag actgctgcaa gagacaagcg agcagctggt ggccctgaag    420
ccctggatca caagacagaa cttcagcaga tgcctcgagc tgcagtgtca gcctgacagc    480
tccaccctgc ctcctcccctg gtccctaga ccctggagg ctaccgctcc cacgccccc    540
ggcgggggca gcggcgacat ggctagattc gaggacccca caagaagacc ctacaagctg    600
cccgacctgt gcaccgaact gaacacaagc ctgcaagaca tcgagattac ctgcgtgtat    660
tgcaagaccg tgctggagct gaccgaggtg ttcgagttcg ccttcaagga cctgttcgtg    720
gtgtacagag atagcatccc ccacgccgcc tgccacaagt gcatcgactt ctatagcaga    780
atcagagaac tgcggtacta cagcgatagc gtgatgtacg gccccaaggc caccctccaa    840
gacatcgtcc tgcacctgga gcctcagaat gagatccccg tggacctgct gtgccacgag    900
cagctgagcg acagcgagga agaaacgac gagatcgacg gcgtcaatca tcagcacctg    960
cccgctagac gggctgagcc tcagcggcac accatgctgt gtatgtgctt ctacagcaga    1020
attagagagc tcagatacta cagcgacagc gtgtatgcg acaccctgga gaagctgacc    1080
aacaccggcc tgtacaatct gctgatcaga tgcctgagat gtcagaagcc cctcaacccc    1140
gccgagaagc tgagacacct gaacgagaag aaagattcc acaagatcgc cggccactac    1200
agagggcagt gccacagctg ctgcaacaga gctagacaag agagactgca gagacggcgg    1260
gaaacccaag tggctagaag ggccgagcct cagagacata caatgctgtg catgtgctgc    1320
aagtgcgaag ctagaatcga gctggtggtg gagagcagcg ccgacgacct gagagccttt    1380
cagcagctgt tcctgagcac cctgagcttc gtgtgcccct ggtgcgctag ccaacagatg    1440
catcagaaga gaaccgccat gttccaagac ccccaagaga gacctagaaa gctgccccac    1500
ctgtgtaccg agctgcagac aaccatccac gacatcatcc tggagtgcgt gtactgcaag    1560
cagcaactgc tgagaagaga ggtgtacgac ttcgccttca gagacctgtg catcgtgtac    1620
cgggacggga atccctacgc cgtgtgcgac aaatgtctca gtttttatag caagattagc    1680
gagtacagat acatgcacgg cgacacccc accctgcacg agtacatgct ggacctgcag    1740
cccgagacca ccgacctgta ctgctacgaa caactgaacg acagctccga ggaagaggac    1800
gaaatcgacg gcccgccgg ccaagccgag ccgacagag cccactacaa cattgtgaca    1860
ttctgttgca agtgtgacag cacactggac aaatgctaca agcaagatcagc    1920
gagtacagat attactgcta cagcgtgtac ggcaccaccc tggagcagca gtacaacaag    1980
cccctgtgtg acctgctgat tagatgcatc aactgtcaga gccctgtg ccccgaggag    2040
aagcagagac acctggacaa gaagcagaga ttccacaaca tcagaggcag atggaccggc    2100
agatgcatga gctgctgcag aagcagcaga acaagaagga gacacagct gcactacaat    2160
atcgtgacct tttgctgcaa gtgcgatagc accctgcggg tgtgcgtgca gagcacccac    2220
```

```
gtggacatca gaaccctgga ggacctgctg atgggcaccc tgggcatcgt gtgccccatc   2280
tgcagccaaa agccctgatg a                                             2301

SEQ ID NO: 49           moltype = RNA  length = 2301
FEATURE                 Location/Qualifiers
source                  1..2301
                        mol_type = other RNA
                        organism = synthetic construct
SEQUENCE: 49
atggacgcca tgaagcgcgg gctttgctgc gtcctgctgt tatgcggcgc tgtgttcgtc    60
agccctagca taacgcagga ctgcagcttc cagcacagcc ctatatcttc ggacttcgcg   120
gtcaagattc gggagctctc cgactatctg ctccaggact atcccgtcac ggtcgccagc   180
aaccttcagg acgaagagtt gtgtggcggc ctgtggcggt tagtcctggc gcagcgttgg   240
atggagcgcc tgaagaccgt ggctggttcg aagatgcagg gcttgctgga gcgggtgaac   300
acggagattc acttcgtgac caagtgcgcg tttcagcctc cgccgagctg tctgaggttc   360
gtgcagacga acatcagtcg gctcttgcag gagactagcg agcagttggt cgcgttgaag   420
ccgtggatca cccgccagaa ctttagtcgg tgcctcgagc tgcagtgcca gccagattcc   480
tcgaccctcc ctccgccgtg gtcgccgcgg ccgctgcagg ccacggcgca cacggcgcct   540
ggcggcggga gcggtgacat ggcgcggttc gaggacccga ctcgcaggcc gtataagtta   600
ccggatctct gtacagagct gaacacgtcc ttgcaggaca tcgaaatcac ctgcgtgtac   660
tgcaagaccg tcttggagtt aacggagtg ttcgagttcg ccttcaagga cttgttcgtt   720
gtgtacagag attcgatacc tcatgcggcc tgccacaagt gcatcgattt ctattcgcgc   780
attcgagagc tgaggtacta ctcggacagt gtcatgtacg ggcctaaggc cacgttacag   840
gacattgtcc tccacctgga acctcagaat gagattccgg tggacctgct ctgccatgag   900
cagctctcgg actccgagga agagaacgat gagatcgacg gagtgaacca tcagcacctg   960
cccgcgagaa gggcagagcc acagcgtcac acaatgctgt gtatgtgctt ctactcgcgg  1020
atcagggagc tgaggtatta ctccgactcg gtctacggaa acaccttaga gaagttgaca  1080
aacaccggtt tgtacaacct tctcataagg tgtctccgtt gccaaaagcc tctgaatccg  1140
gcggagaagc tgcggcatct caacgagaag cggcggtttc acaagatcgc cgggcactac  1200
agaggacagt gccacagctg ctgcaaccgc gccagacagg agcggttgca gcggcggcgc  1260
gagacccagg ttgcccggcg agccgagccg cagcgacata caatgctttg tatgtgctgc  1320
aagtgcgagg ctcggataga gcttgtcgtg gaatcttctg cggatgacct gcgagcattc  1380
cagcagctgt ttctgagcac tctgtcgttc gtgtgcccgt ggtgcgcgag ccagcagatg  1440
catcagaagc ggactgctat gttccaagac ccgcaggaga ggccacgcaa gcttccacat  1500
ctgtgtacag agctccaaac caccatccac gacatcatcc tggagtgcgt gtactgcaaa  1560
cagcagctgc tgagaagaga ggtgtacgac ttcgccttca gagacctgtg catcgtgtac  1620
agagatggga atccctacgc cgtgtgcgac aagtgcctga gttctatag caagatcagc  1680
gagtacagat acatgcatgg cgacacaccc accctgcacg agtacatgct ggacctgcag  1740
cccgacacca ccgacctgta ctgctatgag cagctgaacg acagcagcga agaggaggac  1800
gagatcgacg gccctgctgg ccaagccgag cccgacagag cccactataa catcgtcaca  1860
ttctgttgca aatgtgactc caccctggac aagtgtctga aattctatag caagatctcc  1920
gagtaccggt actactgtta cagcgtgtac ggcaccacac tggagcagca gtacaacaag  1980
ccgctttgcg atctgctgat ccggtgcatc aactgtcaga gccctttgtc tcccgaagag  2040
aagcagagac acctgacaa gaagcagaga ttcacaacaa tcagaggcag atggaccggc  2100
agatgcatga gctgctgcag aagcagcaga cccggagag agacccaact ccactacaat  2160
atcgtgacct tctgttgcaa gtgcgatagc accctgagac tgtgcgtgca gagcacccac  2220
gtggacatca gaaccctgga ggacctgctg atgggcaccc tgggcatcgt gtgccccatc  2280
tgcagccaaa agccctgatg a                                             2301

SEQ ID NO: 50           moltype = RNA  length = 2301
FEATURE                 Location/Qualifiers
source                  1..2301
                        mol_type = other RNA
                        organism = synthetic construct
SEQUENCE: 50
atggacgcca tgaagagagg cctgtgctgc gtgctgctcc tgtgcggcgc cgtgttcgtg    60
agccctagca tcacccaaga ctgcagcttt cagcacagcc ccatcagcag cgacttcgcc   120
gtgaagatca gagaactcag cgactacctg ctgcaagact accccgtgac cgtggctagc   180
aacctgcaag acgaggagct gtgcggcggc ctgtggcggc tcagagatgg   240
atggagagac tgaagaccgt ggccggcagc aagatgcaag gcctgctgga gagtgtgaac   300
accgagatcc acttcgtgac caagtgcgcc tttcagcccc ctcctagctg cctgagattc   360
gtgcagacca catcagcag actgctgcaa gagacaagcg agcagctggt ggccctgaag   420
ccctggatca aagacagaa cttcagcaga tgcctggagc tgcaatgtca gcccgacagc   480
agcaccctcc cccctccctg gagccctaga cccctgcagg ccaccgccca caccgcccct   540
ggcgggggca gcggcgacat ggctagattc gaggacccca agaagaccct acaagctgc   600
cccgatctct gcacagagct gaacacaagc ctgcaagaca tcgagatcac ctgcgtgtat   660
tgcaagaccg tgctggagct gaccgaggtg ttcgagttcg ccttcaagga cctgttcgtg   720
gtgtacagag acagcatccc cacgccgcc tgccacaagt gcatcgactt ctacagccgg   780
atcagagagc tccggtacta cagcgactcg gtgatgtacg gccccaaggc cacctccaa   840
gacatcgtgc tgcacctgga gcctcagaac gagatcccg tggacctgct gtgccacgag   900
cagctgagcg acagcgagga agagaacgac gaaattgacg gcgtgaacca tcagcacctg   960
cccgctagag ggccgagcc tcagcggcac accatgctgt gtatgtgctt ctacagcaga  1020
atcagagaac tcagatatta ctccgactcc gtgtacggcg acactctgga agagctgacc  1080
aacaccggtc tgtacaacct tctgatcaga tgctgcaga tgcagaagcc tctcaatccc  1140
gccgagaagc tgagacacct gaacgagaag agaagattcc acaagatcgc cggccactac  1200
agagggcagt gccacagctg ctgcaacaga gctagacaag agactgca gagaagacgg  1260
gagacccaag tggctagaag ggccgagcct cagacacca catgctgtg catgtgctgc  1320
aagtgcgaag ctagaatcga gctggtggtg gagagcagcg ccgacgacct gagagccttt  1380
cagcagctgt tcctgagcac cctgagcttc gtgtgcccct ggtgcgctag ccaacagatg  1440
```

-continued

```
catcagaaga gaaccgccat gttccaagac ccccaagaga gacctagaaa gctgccccac    1500
ctgtgtacag agctccaaac caccatccac gacatcatcc tggagtgcgt gtactgcaaa    1560
cagcagctgc tgagaagaga ggtgtacgac ttcgccttca gagacctgtg catcgtgtac    1620
agagatggga atccctacgc cgtgtgcgac aagtgcctga gttttatag caagatcagc     1680
gagtacagat acatgcatgg cgacaccccc accctgcacg agtacatgct ggacctgcag    1740
cccgagacca ccgacctgta ctgctatgag cagctgaacg acagcagcga agaggaggac    1800
gagatcgacg gccccgctgg ccaagccgag cccgacagag cccactataa catcgtcaca    1860
ttctgttgca aatgtgactc caccctggac aagtgtctga aattctatag caagatctcc    1920
gagtaccggt actactgtta cagcgtgtac ggcaccacac tggagcagca gtacaacagc    1980
cccctgtgcg atctgctgat ccggtgcatc aactgtcaga agccctgtg tcccgaagag     2040
aagcagagac acctggacaa gaagcagaga ttccacaaca tcagaggcag atggaccggc    2100
agatgcatga gctgctgcag aagcagcaga acccggagag agacccaact ccactacaat    2160
atcgtgacct tctgttgcaa gtgcgatagc accctgagac tgtgcgtgca gagcacccac    2220
gtggacatca gaaccctgga ggacctgctg atgggcaccc tgggcatcgt gtgccccatc    2280
tgcagccaaa agccctgatg a                                              2301

SEQ ID NO: 51          moltype = RNA  length = 2337
FEATURE                Location/Qualifiers
source                 1..2337
                       mol_type = other RNA
                       organism = synthetic construct
SEQUENCE: 51
atggacgcca tgaagagagg cctgtgctgc gtgctgctcc tgtgcggcgc cgtgttcgtg    60
agccctagca tcacccaaga ctgcagcttt cagcacagcc ccatcagcag cgacttcgcc    120
gtgaagatcc gggagctgtc cgactacctg ctgcaagact accccgtgac cgtggctagc    180
aacctgcaag acgaggagct gtgcggcggc ctgtggagac tggtgctggc tcagagatgg    240
atggagagac tgaagaccgt ggccggcagc aagatgcaag gcctgctgga gagagtgaac    300
accgagatcc acttcgtgac caagtgcgcc tttcagcccc ctcctagctg cctgagattc    360
gtgcagacca acatcagcag actgctgcaa gagacaagcg agcagctggt ggccctgaag    420
ccctggatca aagacagaa cttcagcaga tgcctggaac tccaatgtca gcccgacagc    480
agcaccctgc ctcccccctg gagccctaga cccctcgaag ccacagcccc cacagccccc    540
gggggggca gcggcgacat gcatcagaag agaaccgcca tgttccaaga ccccaagag     600
agacctagaa agctgcccca cctgtgcacc gagctgcaga ccaccatcca cgacatcatc    660
ctggagtgcg tgtactgtaa gcagcagctg ctgagaagag aggtgtacga cttcgccttc    720
agagacctgt gcatcgtgta tagagacggc aaccctacg ccgtgtgcga taagtgcctg     780
aaattctact ccaagatcag cgagtacaga tacgccgcca tgcacggcga caccccccac    840
ctgcacgagt acatgctgga cctgcagccc gagaccaccg acctgtactg ctacgagcag    900
ctgaacgaca gctccgaaga ggaggacgag atcgacggcc ccgccggcca agccgagccc    960
gacagagctc actacaatat cgtgacattc tgctgcaagt gcgactccac actgctgcc    1020
gacaagtgcc tcaagtttta cagcaagatc tccgaataca gatactactg ctacagcgtg    1080
tacgggacca ccctggagca gcagtacaac aaacctctct gcgacctgct gattagatgc    1140
attaattgtc agaagcccct gtgccccgag gagaagcaga gacacctgga caagaagcag    1200
agattccaca acatcagagg cagatggacc ggcagatgct gcagaagcgc    1260
agaacaagaa gagagacaca gctggccgct cactacaaca tcgtcacctt ctgttgtaag    1320
tgcgactcca ccctgagact gtgcgtgcag agcacccacg tggacatcag aaccctggag    1380
gacctgctga tgggcaccct gggcatcgtg tgccccatct gcagcaaaa gcccatggct    1440
agattcgagg accccacaag aagccctac aagtgcccg acctgtgtac agaactgaac    1500
acaagcctgc aagacatcga gatcacctgc gtgtactgca gaccgtgct ggagctgacc    1560
gaggtgttcg agttcgcctt caaggacctg ttcgtggtgt acagagacag catcccccac    1620
gccgctgcc acaagtgcat cgacttctac agcagaatta gagaactgcg gtactacagc    1680
gacagcgtgg ccgccatgta cggccccaag gccaccctcc aagacatcgt gctgcacctc    1740
gagcctcaga acgagatccc cgtggacctg ctgtgccacg aacagctgag cgacagcgag    1800
gaagagaacg acgagattga cggcgtgaac catcagcacc tgcccgctcg gagagctgag    1860
ccccaacggc acaccatgct gtgtatgtgt ccgctttct atagcagaat ccgggagctg    1920
cggtactatt ccgacagcgt gtacgggac acactgagca gctgaccaa caccggcctg    1980
tacaatctgc tgatcagatg cctcagatgt cagaaacccc tcaacccctg cgagaagctg    2040
agacacctga cgagaagag aagattccac aagatcgccg ccactacag agggcagtgc    2100
cacagctgct gcaacagagc tagacaagag agactgcaga gacggagaga gacccaagtg    2160
gccgctgcta gagggccga gcctcagaga cacacaatgc tgtgcatgtg ctgcaaatgc    2220
gaggctagaa tcgagctggt ggtggagagc agcgccgacg acgctgagac ctttcagcag    2280
ctgttcctga gcaccctgag cttcgtgtgc ccctggtgcg ctagccaaca gtgatga      2337

SEQ ID NO: 52          moltype = RNA  length = 3219
FEATURE                Location/Qualifiers
source                 1..3219
                       mol_type = other RNA
                       organism = synthetic construct
SEQUENCE: 52
atggacgcca tgaagagagg cctgtgctgc gtgctgctcc tgtgcggcgc cgtgttcgtg    60
agccctagca tcacccaaga ctgcagcttt cagcacagcc ccatcagcag cgacttcgcc    120
gtgaagatca gagagctgag cgactacctg ctgcaagact accccgtgac cgtggctagc    180
aacctgcaag acgaggagct gtgcggcggc ctgtggagac tggtgctggc tcagagatgg    240
atggagagac tgaagaccgt ggccggcagc aagatgcaag gcctgctgga gagagtgaac    300
accgagatcc acttcgtgac caagtgcgcc tttcagcccc ctcctagctg cctgagattc    360
gtgcagacca acatcagcag actgctgcaa gagacaagcg agcagctggt ggccctgaag    420
ccctggatca aagacagaa cttcagcaga tgcctggagc tgcagtgtca gcctgacagc    480
agcaccctcc cccctcccctg gagccccggg cctctgaggg ctacagcccc cacagccccc    540
ggcggggca gcggcgacat gaacgtgtgc aagacaagat cctggaaca ctacgagaat    600
gacagcaaag acattctgga gcactacgaa aatgattcca aggacctgtg tgaccatatc    660
```

```
tgtgatcata tcgattattg gaagcacatc agactggaat gtgctatcat gtacaaggcc   720
cggatcagac tggagtgcgc catcatgtac aaggctcggg aaatgggctt ccatcagttc   780
gacggcgaca tctgcaacac catgcactac accaactgga tctacatctg cgaggacgct   840
cagtgcaccg tggtggaggg ccaagtggac aagaagtggg aggtgcacgc cggcggccaa   900
gtgatcctgt gccctgaaag cgggcagaga agaatcaaga gaccccggag cgagaactgc   960
caccccaaca agctgctgat cctgaagtgc ctgagataca gattcaagaa gcactgcaag  1020
ctgagcagca cctggcactg gacctgccat gatggcaaac acaagtggca ctggacctgc  1080
cacgacggca agcataagaa tgccatcgtg accctgacct acgaccacat cgattattgg  1140
aaggccatca gacaagagaa cgccatcttc ttcgccgcta gacaccaagt ggtgcccgcc  1200
ctgaacatct gcaaggccaa ggcctgcaag gccatcgagt ggaacaccga gcccaagcac  1260
tgcttcaaga agggcgggca gcacatcgag gtgtggttcg actacgtcgc ctgggatagc  1320
gtgtactact gcgcgacga cggctggtgc aagaccgagg ccgagaagta cggctgcaag  1380
ggcacctggg aggtccactt cggcaacagc atcgactgca acgacagcat gtgcagcacc  1440
ttcgacgaca acgtgagcgc caccgagctg gtgaagatgc atcagaagag aaccgccatg  1500
ttccaagacc cccaagagag acctagaaaa ctcccccatc tgtgcaccga actgcagacc  1560
accatccacg acatcatcct ggagtgcgtg tattgcaaac aacagctgct gagaagagag  1620
gtgtacgact tcgccttcag agacctgtgc atcgtgtacc gggacggcaa tcctacgcc   1680
gtgtgcgaca agtgcctcaa gttctatagc aagatcagcg agtatagata catgcacggg  1740
gacaccccca ccctgcacga gtacatgctg gacctgcagc ccgagaccac cgacctgtac  1800
tgctacgagc agctgaacga cagcagcgaa gaggaggacg agattgacgg ccccgccggc  1860
caagccgagc ccgacagagc ccactacaac atcgtgacct tctgctgtaa atgcgatagc  1920
acactggaca agtgcctgaa ttctacagcg aagattacgg agtacagata ttactgctac  1980
tccgtgtacg ggacaaccct ggagcagcag tacaacaagc ctctgtgcga cctgctgatc  2040
cggtgtatta actgtcagaa gcccctgtgc cccgaggaga agcagagaca cctggacaag  2100
aagcagagat tccacaacat cagaggcaga tggaccggca gatgcatgag ctgctgcaga  2160
agcacgagaa caagaagaga gacacaactg cactacaata tcgtcaccct ctgctgcaag  2220
tgcgactcca cactgcggct ctgcgtgcag agcacccacg tggacatcag aaccctggag  2280
gacctgctga tgggcaccct gggcatcgtg tgccccatct gcagccaaaa gcccatggct  2340
agattcgagg accccacaag aagacccctac aagctgcccg acctgtgcac cgagctgaac  2400
acaagcctcc aagcatcga gattacctgc gtgtactgca agaccgtgct ggagctgacc  2460
gaggtgttcg agttcgcctt caaggacctg ttcgtggtgt acagagacag catccccacc  2520
gccgcctgcc acaagtgcat cgacttctac agccggattc gggaactgcg gtactacagc  2580
gacagcgtga tgtatggccc caaggccacc ctgcaagaca tcgtgctgca cctggagcct  2640
cagaacgaaa tccccgtgga cctgctgtgc catgagcaac tgagcgacag cgaggaagag  2700
aatgatgaga tcgacgacgt gaatcatcag cacctgcccg ctagaagggc cgagcccaa   2760
cggcacacca tgctgtgcat gtgcttctac agcagaatca gagaactccg gtattacagc  2820
gactccgtgt acgggatac cctcgagaag ctgaccaaca ccggcctgta caatctgctg  2880
atcagatgtc tgagatgtca gaaacccctg aaccccgccg agaagtgag acacctgaac  2940
gagaagagaa gattccacaa gatcgccggc cactacagag gcagtgcca cagctgctga  3000
aacagagcta gacaagagag actgcagaga agacggagga cccaagtggc tagaagggct  3060
gagcccccaaa gacataccat gctgtgtatg tgctgcaaat gcgaggctag aatcgagctg  3120
gtggtggaga gcagcgccga cgacctgaga gcctttcagc agctgttcct gagcaccctg  3180
agcttcgtgt gcccctggtg cgctagccaa cagtgatga               3219

SEQ ID NO: 53            moltype = RNA   length = 3219
FEATURE                  Location/Qualifiers
source                   1..3219
                         mol_type = other RNA
                         organism = synthetic construct
SEQUENCE: 53
atggacgcca tgaagcgcgg tctgtgctgc gtcctgctgt tatgcggcgc tgtgttcgtc    60
agccctagca taacgcagga ctgcagcttc cagcacagcc ctatatcttc ggacttcgcg   120
gtcaagattc gggagctctc cgactatctg ctccaggact atcccgtcac ggtcgccagc   180
aaccttcagg acgaagagtt gtgtggcggc ctgtggcggt tagtcctggc gcagcgttgg   240
atggacgcc tgaagaccgt ggctggttcg aagatgcagg gcttgctgga gcgggtgaac   300
acggagattc acttcgtgac caagtgcgcg tttcagcctc cgccgagctg tctgaggttc   360
gtgcagacga acatcagtcg gctcttgcag gagactagcg agcagttggt cgcgttgaag   420
ccgtggatca cccgccagaa cttctcacgt tgccttgagc tgcagtgcca gccggattcc   480
tcgaccctcc ctcgccgtg gtcgccgcgg ccgctggagg ccacggcgcc cacgcgcct   540
ggcggagggt cgggcgacat gaacgtgtgc caggataaga tcttggagca ttacgagaat   600
gactccaagg atatcctgga gcactatgag aacgactcca aggatctatg tgatcacatc   660
tgtgatcaca tagattattg gaagcacatc cggctggagt gcgccattat gtataaggcg   720
cgtatccggc tggaatgtgc tataatgtat aaagcccgtg agatgggctt tcaccagttc   780
gatggtgaca tttgtaacac aatgcactat acgaactgga tatacatctg cgaggacgtg   840
cagtgtacgg tagttgaggg tcaggtagac aagaagtggg aggttcacgc cggtgggcag   900
gtcatcctct gcccggagtc cgggcagagg aggatcaagg tccgcgcgag tgaaaactgc   960
caccctaaca agctactgat cctcaagtgc cttcgctatc gcttcaagaa gcattgcaag  1020
ttgtcgtcca cgtggcactg gacttgccac gacggcaaga caagtggca ctggacgtgc  1080
cacgacggca agcacaagaa cgcgatagtg acgcttacct atgatccat agattattgg  1140
aaagcgatcc ggcaggagaa tgcgatattc ttcgctgcac gccaccaggt ggtgcccgcg  1200
ttgaatatct gcaaggcgaa ggcctgcaag gccatagagt ggaacacaga gccgaagcac  1260
tgctttaaga aggcggtca gcacatcgag gtctggttcg actatgtggc ctgggactcg  1320
gtctactatt gcgcgcgacga cggttggtgc aagaccgagg ccgagaaata cggctgcaag  1380
ggcacctggg aagttcactt tggtaacagc atcgattgca acgactccat gtgcagcacg  1440
tttgacgata acgtgtctgc cacggagttg gtaaagatgc accaagaagcg gaccgcgatg  1500
ttccaagatc ctcaagagag acctagaaaa ctcccgcatc tgtgcaccga actgcagacc  1560
accatccacg acatcatcct ggagtgcgtg tattgcaaac aacagctgct gagaagagag  1620
gtgtacgact tcgccttcag agacctgtgc atcgtgtacc gggacggcaa tcctacgcc   1680
gtgtgcgaca agtgcctcaa gttctatagc aagatcagcg agtatagata catgcacggc  1740
```

```
gacacaccga cccctgcacga gtacatgctg gacctgcagc ccgagaccac cgacctgtac 1800
tgctacgagc agctgaacga cagcagcgaa gaggaggacg agattgacgg ccctgccggc 1860
caagccgagc ccgacagagc ccactacaac atcgtgacct tctgctgtaa atgcgatagc 1920
acactggaca agtgcctgaa gttctacagc aagattagcg agtacagata ttactgctac 1980
tccgtgtacg ggacaaccct ggagcagcag tacaacagcc ctctgtgcga cctgctgatc 2040
cggtgtatta actgtcagaa gccactgtgc cctgaggaga agcagagaca cctggacaag 2100
aagcagagat tccacaacat cagaggcaga tggaccggca gatgcatgag ctgctgcaga 2160
agcagcagaa caagaagaga gacacaactg cactacaata tcgtcacctt ctgctgcaag 2220
tgcgactcca cactgcggct ctgcgtgcag agcacccacg tggacatcag aaccctggag 2280
gacctgctga tgggcaccct gggcatcgtg tgcccgatct gcagccaaaa gcccatgggt 2340
agatttgaag atcccacaag aagacccta aagctgcccg acctgtgcac cgagctgaac 2400
acaagcctcc aagacatcga gattacctgc gtgtactgca agaccgtgct ggagctgacc 2460
gaggtgttcg agttcgcctt caaggacctg ttcgtggtgt acagagacag cattcctcac 2520
gccgcctgcc acaagtgcat cgacttctac agccggattc ggaactgcg gtactacagc 2580
gacagcgtga tgtatggccc gaaggccacc ctgcaagaca tcgtgctgca cctggagcct 2640
cagaacgaaa tacccgtgga cctgctgtgc catgagcaac tgagcgacag cgaggaagag 2700
aatgatgaga tcgacggcgt gaatcatcag cacctgcccg ctagaagggc cgagccgcaa 2760
cggcacacca tgctgtgcat gtgcttctac agcagaatca ggaactcctg gtattacagc 2820
gactccgtgt acgagacac cctcgagaag ctgaccaaca ccggcctgta caatctgctg 2880
atcagatgtc tgagatgtca gaaacccttg aatcccgccg agaagctgag acacctgaac 2940
gagaagagaa gattccacaa gatcgccggc cactacagag ggcagtgcca cagctgctgc 3000
aacagagcta gacaagagag actgcagaga agacgggaca cccaagtggc tagaagggct 3060
gagcctcaaa gacataccat gctgtgtatg tgctgcaaat gcgaggctag aatcgagctg 3120
gtggtggaga gcagccgcga cgacctgaga gcctttcagc agctgttcct gagcaccctg 3180
agcttcgtgt gtccctggtg cgctagccaa cagtgatga              3219

SEQ ID NO: 54         moltype = RNA   length = 3219
FEATURE               Location/Qualifiers
source                1..3219
                      mol_type = other RNA
                      organism = synthetic construct
SEQUENCE: 54
atggacgcca tgaagcgcgg tctttgctgc gtcctgctgt tatgcggcgc tgtgttcgtc 60
agccctagca taacgcagga ctgcagcttc cagcacagcc ctatatcttc ggacttcgtg 120
gtcaagattc gggagctctc cgactatctg ctccaggact atcccgtcac ggtcgccagc 180
aaccttcagg acgaagagtt gtgtggcggc ctgtggcggt tagtcctggc gcagcgttgg 240
atggagcgcc tgaagaccgt ggctggttcg aagatgcagg gcttgctgga gcgggtgaac 300
acggagattc acttcgtgac caagtgcgcg tttcagcctc cgccgagctg tctgaggttc 360
gtgcagacga acatcagtcg gctcttgcag gagactacgg agcagttggt gccgttgaag 420
ccgtggatca cccgcagaa cttctcacgt tgccttgagc tgcagtgcca gccggattcc 480
tcgaccctcc ctccgccgtg gtcgccgcgg ccgctggagg ccacgcgcc acggcgcct 540
ggcggcggga gcggagatat gaacgtgtgc caggataaga tcttggagca ttacgagaat 600
gactccaagg atatcctgga gcactatgag aacgactcca aggatctatg tgatcacatc 660
tgtgatcaca tagattattg gaagcacatc cggctggagt gcgccattat gtataaggct 720
cggatacggc tggaatgtgc tataatgtat aaagcccgtg agatgggctt tcaccagttc 780
gatggtgaca tttgtaacac aatgcactat acgaactgga tatacatctg cgaggacgcg 840
cagtgtacgg tagttgaggg tcaggtagac aagaagtgag aggttcacgc gggtgggcag 900
gtcatcctct gcccggagtc cgggcagagg aggatcaagc gtccgcggag tgaaaactgc 960
caccctaaca agctactgat cctcaagtgc cttgctatc gcttcaagaa gcattgcaag 1020
ttgtcgtcca cgtggcactg gacttgccac gacggcaagc acaagtggca ctggacgtgc 1080
cacgacggca agcacaagaa cgcgatagtg acgcttacct atgatcacat agattattgg 1140
aaagcgatcc ggcaggagaa tgcgatattc ttcgctgcta gacaccaggt ggtgcccgcg 1200
ttgaatatct gcaaggcgaa ggctgcaag gccatagagt ggaacacaga gccgaagcac 1260
tgctttaaga aaggcggtca gcacatcgag gtctggttcg actatgtggc ctgggactcg 1320
gtctactatt gcggcgacga cggttggtgc aagaccgagg cgcgagaaata cggctgcaaa 1380
gggacgtggg aagttcactt cgggaactcc atcgattgca acgactccat gtgcagcacg 1440
tttgacgata acgtgtctgc cacggagttg gtaaagatgg cccgattcga agatcccaca 1500
agaagaccct acaagctgcc cgacctgtgc accgagctga acacaagcct ccaagacatc 1560
gagattacct gcgtgtactg caagaccgtg ctggagctgc ccgaggtgtt cgagttcgcc 1620
ttcaaggacc tgttcgtggt gtacagagac agcatcccac gccgcctg ccacaagtgc 1680
atcgacttct acagccggat tcgggaactg cggtactaca gcgacagcgt gatgtatggg 1740
cccaaggcca ccctgcaaga catcgtgctg cacctggagc tcagaacga atacccgtg 1800
gacctgctgt gccatgagca actgagcgac agcgaggaag agaatgatga gatcgacggc 1860
gtgaatcatc agcacctgcc cgctagaagg gccgagccac catgctgtgc 1920
atgtgcttct acagcagaat cagagaactc cggtattaca gcgactccgt gtacgagat 1980
accctcgaga agctgaccaa caccggcctg tacaatctgc tgatcagatg tctgagatgt 2040
cagaaaccct taaatcccgc cgagaagctg agacacctga cgagaagag aagattccac 2100
aagatcgccg gccactacag agggcagtgc cacagctgct gcaacagagc tagacaagag 2160
agactgcaga gaagacggga cccaagtgg ctagaaggg aagacatacc 2220
atgctgtgta tgtgctgcaa atgcgaggct agaatcgagc tggtggtgga gagcagcgcc 2280
gacgacctga gagcctttca gcagctgttc ctgagcaccc tgagcttcgt gtgtccctgg 2340
tgcgctagcc aacagatgca tcagaagaga ccgccatgt ccaagatcc gcaagagaga 2400
cctagaaaac tccctcatct gtgcaccgaa ctgcagacca catccacga catcatcctg 2460
gagtctgtgt attgcaaaca acagtgctgt agaagagg tgtacgactt cgccttcaga 2520
gacctgtgca tcgtgtaccg ggacggcaat ccctacgcg tgtcgacaa gtgcctcaag 2580
ttctatagca agatcagcga gtatagatac atgcacggaa atacgccgac cctgcacgag 2640
tacatgctgg acctgcagcc cgagaccacc gacctgtact gctacgagca gctgaacgac 2700
agcagcgaag aggaggacga gattgacggc ccggccggcc aagccgagcc cgacagagcc 2760
cactacaaca tcgtgacctt ctgctgtaaa tgcgatagca cactggacaa gtgcctgaag 2820
```

```
ttctacagca agattagcga gtacagatat tactgctact ccgtgtacgg gacaaccctg    2880
gagcagcagt acaacaagcc tctgtgcgac ctgctgatcc ggtgtattaa ctgtcagaag    2940
cccttgtgtc ccgaggagaa gcagagacac ctggacaaga agcagagatt ccacaacatc    3000
agaggcagat ggaccggcag atgcatgagc tgctgcagaa gcagcagaac aagaagagag    3060
acacaactgc actacaatat cgtcaccttc tgctgcaagt gcgactccac actgcggctc    3120
tgcgtgcaga gcacccacgt ggacatcaga accctggagg acctgctgat gggcaccctg    3180
ggcatcgtgt gtcccatctg cagccaaaag ccctgatga                          3219
```

POLYNUCLEOTIDE MOLECULES USED FOR THE PREVENTION OR TREATMENT OF HPV INFECTION RELATED DISEASES

CROSS-REFERENCE TO RELATED APPLICATIONS

This patent application is a continuation of co-pending International Application No. PCT/CN2023/142229, filed Dec. 27, 2023, which claims priority to Chinese Patent Application No. 202311684185.8, filed Dec. 8, 2023; International Application No. PCT/CN2023/114487, filed Aug. 23, 2023; and International Application No. PCT/CN2022/143328, filed Dec. 29, 2022, the disclosures of which are incorporated herein by reference in their entireties for all purposes.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 98,284 Byte Extensible Markup Language (XML) file named "05-FG00936PCT-seq-EN," created on Jul. 8, 2024.

FIELD OF THE INVENTION

The present application relates to the field of biotechnology, specifically to an mRNA vaccine for treating HPV infection related diseases by inducing HPV antigen-specific immune responses.

BACKGROUND OF THE INVENTION

Diseases caused by high-risk human papillomavirus (HPV) infection account for 5% of all diseases worldwide, wherein 70% of cervical cancer caused by persistent infection with HPV types 16 and 18. The HPV genome contains up to 7 early genes (E1-E7) and 2 late genes (L1 and L2), wherein E6 and E7 proteins are expressed in almost all cervical cancer cells and are also necessary for maintaining the disease phenotype, making them ideal target proteins for therapeutic vaccines.

The HPV therapeutic vaccines currently under research mainly include DNA vaccines, subunit vaccines, and recombinant vector vaccines, etc. mRNA vaccines have the advantages of no integration risk, short half-life, and high safety. They can induce antigen-specific immune responses by expressing viral antigens, kill infected cells (e.g. tumor cells), and thus achieve the goal of treating related tumors. The purpose of the present application is to prepare mRNA vaccines for treatment of HPV infection related diseases.

SUMMARY OF THE INVENTION

The present application provides a preventive or therapeutic nucleic acid and fusion polypeptide for HPV infection related diseases, a pharmaceutical composition or pharmaceutical product containing said therapeutic nucleic acid or fusion polypeptide, and the use of said nucleic acid and fusion polypeptide.

Specifically, on the one hand, the present application provides a polynucleotide molecule comprising at least a coding sequence of an HPV antigen polypeptide, wherein the antigen polypeptide sequentially from the N-terminus to the C-terminus comprises at least:

1) an amino acid sequence A and an amino acid sequence B;
2) an amino acid sequence C, an amino acid sequence A, and an amino acid sequence B;
3) an amino acid sequence B and an amino acid sequence A;
4) an amino acid sequence C, an amino acid sequence B, and an amino acid sequence A;
5) an amino acid sequence A, an amino acid sequence B, and an amino acid sequence C;
6) an amino acid sequence B, an amino acid sequence A, and an amino acid sequence C;
7) an amino acid sequence A, an amino acid sequence C, and an amino acid sequence B or
8) an amino acid sequence B, an amino acid sequence C, and an amino acid sequence A.

wherein, the amino acid sequence A sequentially from the N-terminus to the C-terminus comprises at least SEQ ID NOs: 1, 2, 3, 4 or variants thereof, and each of the amino acid sequences represented by the SEQ ID NOs is connected directly and sequentially or by a linker sequentially;

the amino acid sequence B sequentially from the N-terminus to the C-terminus comprises at least SEQ ID NOs: 5, 6, 7, 8 or variants thereof, and each of the amino acid sequences represented by the SEQ ID NOs is connected directly and sequentially or by a linker sequentially; and the amino acid sequence C comprises an HPV E2 antigen sequence.

In some embodiments, the variant is a conservative substitution variant. In some embodiments, each of the amino acid sequences of the variants of SEQ ID NO: 1-4 has at least 80%, 85%, 90%, 95%, 96%, 97%, 98%, 98.5%, 99%, and 99.5% sequence identity with one of the amino acid sequences of SEQ ID NOs: 1-4, respectively. In some embodiments, each of the amino acid sequences of the variants of SEQ ID NO: 5-8 has at least 80%, 85%, 90%, 95%, 96%, 97%, 98%, 98.5%, 99%, and 99.5% sequence identity with one of the amino acid sequences of SEQ ID NO: 5-8, respectively.

In some embodiments, the amino acid sequence C is the HPV E2 antigen sequence.

In some embodiments, the HPV E2 antigen sequence is SEQ ID NO: 9 or a variant thereof. In some embodiments, the variant of SEQ ID NO: 9 is a conservative substitution variant. In some embodiments, the variants of SEQ ID NO: 9 have amino acid sequences with at least 80%, 85%, 90%, 95%, 96%, 97%, 98%, 98.5%, 99%, or 99.5% sequence identity with SEQ ID NO: 9.

In some embodiments, the linker peptide comprises one, two or more amino acid residues. In some embodiments, the linker peptide is a flexible linker peptide, a rigid linker peptide, or a combination thereof. In some embodiments, the amino acid sequences of each segment shown in the SEQ ID NO are connected by different linker peptides. In some embodiments, the amino acid sequences of each segment shown in the SEQ ID NO are connected by the same linker peptide. In some embodiments, the linker peptide consists of 2-10 amino acid residues. In some embodiments, the amino acid residue is glycine, serine, and/or alanine residues. In some embodiments, the linker peptide is selected from GS linker, (Gly) 8, a spiral structured peptide segments, (XP) n, etc. In some embodiments, the amino acid sequences of each segment shown in SEQ ID NO are connected by two alanine residues.

In some embodiments, the HPV antigen polypeptide comprises SEQ ID NO: 12, SEQ ID NO: 13, SEQ ID NO: 14, SEQ ID NO: 15, or SEQ ID NO: 16, or comprises an amino acid sequence having at least 99.5%, 99%, 98.5%, 98%, 97%, 96%, 95%, 90%, 85%, or 80% sequence identity with SEQ ID NO: 12, SEQ ID NO: 13, SEQ ID NO: 14, SEQ ID NO: 15, or SEQ ID NO: 16. In some embodiments, the HPV antigen polypeptide comprises SEQ ID NO: 12, SEQ ID NO: 13, SEQ ID NO: 14, SEQ ID NO: 15, or SEQ ID NO: 16, or comprises an amino acid sequence having 98%, 98.5%, 99%, and 99.5% or more sequence identity with SEQ ID NO: 12, SEQ ID NO: 13, SEQ ID NO: 14, SEQ ID NO: 15, or SEQ ID NO: 16. In some embodiments, the HPV antigen polypeptide is SEQ ID NO: 12, SEQ ID NO: 13, SEQ ID NO: 14, SEQ ID NO: 15, or SEQ ID NO: 16.

In some embodiments, the polynucleotide molecules further comprise coding sequences of immune stimulating factors or their functional domains. In some embodiments, the coding sequence of the immune stimulating factor or its functional domain is located on the 3' or 5' end of the coding sequence of the HPV antigen polypeptide. In some embodiments, the immune stimulating factor is selected from one or more of the following: IL-3, IL-7, IL-2, IL-4, IL-5, IL-12, IL-13, Flt3L, G-CSF, M-CSF, GM-CSF, EPO, TPO, SCF, IFNα-2α, IFNα-2β, Pre IFNα-2β, MIP-α, STING, HSP70, immune checkpoint inhibitors. In some embodiments, the immune stimulating factor is an antibody or antigen-binding fragment thereof targeting any one or more of the following checkpoint molecules: 2B4, 4-1BB, 4-1BB ligand, B7-1, B7-2, B7H2, B7H3, B7H4, B7H6, BTLA, CD155, CD160, CD19, CD200, CD27, CD27 ligand, CD28, CD40, CD40 ligand, CD47, CD48, CTLA-4, DNAM-1, galectin-9, GITR, GITR ligand, HVEM, ICOS, ICOS ligand, IDOI, KIR 3DL3, LAG-3, OX40, OX40 ligands, PD-L1, PD-1, PD-L2, LAG3, PGK, SIRPα, TIM-3, PD-1, VSIG8. In some embodiments, the immune stimulating factor is Flt3L. In some embodiments, the peptide sequence of the immune stimulating factor comprises at least an amino acid sequence of SEQ ID NO: 10, a conserved substitution variant of SEQ ID NO: 10, or an amino acid sequence having at least 99%, 98%, 97%, 96%, 95%, 90%, 85%, or 80% sequence identity with SEQ ID NO: 10. In some embodiments, the peptide sequence of the immune stimulating factor is an amino acid sequence of SEQ ID NO: 10, or a conserved substitution variant of SEQ ID NO: 10, or an amino acid sequence having at least 99%, 98%, 97%, 96%, 95%, 90%, 85%, or 80% sequence identity with SEQ ID NO: 10. In some embodiments, the encoding sequence of the immune stimulating factor comprises a polynucleotide sequence of SEQ ID NO: 29 or is a polynucleotide sequence of SEQ ID NO: 29. In some embodiments, the coding sequence of the immune stimulating factor is a nucleotide sequence having at least 99%, 98%, 97%, 96%, 95%, 90%, 85%, or 80% sequence identity with SEQ ID NO: 29.

In some embodiments, the encoding sequence of the immune stimulating factor comprises a synonymous mutant of SEQ ID NO: 29 or is a synonymous mutant of SEQ ID NO: 29.

In some embodiments, the polynucleotide molecule further comprises a signal peptide encoding sequence. In some embodiments, the signal peptide coding sequence is located at the 5' end of the coding sequence of the HPV antigen polypeptide. In some embodiments, the signal peptide is a secretory signal peptide. In some embodiments, the secretory signal peptide is selected from the signal peptide of mammalian secretory proteins. In some embodiments, the mammal is human. In some embodiments, the secretory signal peptide is tPA-SP. In some embodiments, the secretory signal peptide comprises an amino acid sequence of SEQ ID NO: 11, or a conserved substituent variant of SEQ ID NO: 11, or an amino acid sequence having at least 99%, 98%, 97%, 96%, 95%, 90%, 85%, or 80% sequence identity with SEQ ID NO: 11. In some embodiments, the secretory signal peptide is an amino acid sequence as shown in SEQ ID NO: 11, or a conserved substituent variant of SEQ ID NO: 11, or an amino acid sequence having at least 99%, 98%, 97%, 96%, 95%, 90%, 85%, or 80% sequence identity with SEQ ID NO: 11. In some embodiments, the coding sequence of the secretory signal peptide comprises a polynucleotide sequence of SEQ ID NO: 28 or is a polynucleotide sequence of SEQ ID NO: 28. In some embodiments, the coding sequence of the secretory signal peptide is a nucleotide sequence having at least 99%, 98%, 97%, 96%, 95%, 90%, 85%, or 80% sequence identity with SEQ ID NO: 28.

In some embodiments, the coding sequence of the secretory signal peptide comprises a synonymous mutant of SEQ ID NO: 28 or is a synonymous mutant of SEQ ID NO: 28.

In some embodiments, from the 5' end to the 3' end, the polynucleotide molecule comprises sequentially connected coding sequence of the above signal peptide, immune stimulating factor, and HPV antigen polypeptide. In some embodiments, the coding sequence of the signal peptide, the coding sequence of the immune stimulating factor, and the coding sequence of the HPV antigen polypeptide are directly connected or connected through a polynucleotide chain. In some embodiments, the polynucleotide chain comprises 3 or multiples of 3 nucleotides. Alternatively in some embodiments, the polynucleotide molecule consists of sequentially connected coding sequence of the signal peptide, a coding sequence of the immune stimulating factor, and a coding sequence of the HPV antigen polypeptide from the 5' end to the 3' end. In some embodiments, the encoding sequence of the signal peptide, the encoding sequence of the immune stimulating factor, and the encoding sequence of the HPV antigen polypeptide are located in the same reading frame. In some embodiments, the encoding sequence of the reading frame is any one of the polynucleotide sequences shown in SEQ ID NOs: 47-54 or a nucleotide sequence having at least 99%, 98%, 97%, 96%, 95%, 90%, 85%, or 80% sequence identity with any one of the nucleotide sequences shown in SEQ ID NO: 47-54; in some embodiments, the reading frame encodes any one of proteins as shown in SEQ ID NO: 17-21, or an amino acid sequence having at least 99%, 98%, 97%, 96%, 95%, 90%, 85%, or 80% sequence identity with any one of proteins shown in SEQ ID NO: 17-21.

In some embodiments, the polynucleotide molecule is DNA, RNA, or a hybrid of DNA and RNA. In some embodiments, the polynucleotide molecule is extracted from cells. In some embodiments, the polynucleotide molecule is chemically synthesized. In some embodiments, the polynucleotide molecule is not chemically modified in vitro. In some embodiments, the polynucleotide molecule is chemically modified in vitro. In some embodiments, the chemical modification is selected from one or more of the following: m6A, m1A, m5C, m7G, ac4C, 2'-O-methylation, and pseudouracil substitution.

In some embodiments, the polynucleotide molecule comprises any one of the polynucleotide sequences selected from SEQ ID NOs: 28-54. In some embodiments, the polynucleotide molecule consists of any one of the polynucleotide sequences selected from SEQ ID NOs: 28-54. In some embodiments, the polynucleotide molecule consists of any one of the polynucleotide sequences selected from SEQ ID NOs: 39-54. In some embodiments, the polynucleotide molecule comprises a nucleic acid fragment encoded by any one of the polynucleotide sequences selected from SEQ ID NOs: 28-54. In some embodiments, the polynucleotide molecule is encoded by any one of the polynucleotide sequences selected from SEQ ID NOs: 28-54. In some embodiments, the polynucleotide molecule is encoded by any one of the polynucleotide sequences selected from SEQ ID NOs: 39-54. In some embodiments, the polynucleotide molecule comprises a sequence complementary to any one of the polynucleotide sequences selected from SEQ ID NOs: 28-54. In some embodiments, the polynucleotide molecule consists of a sequence complementary to any one of the polynucleotide sequences selected from SEQ ID NOs: 28-54. In some embodiments, the polynucleotide molecule consists of a sequence complementary to any one of the polynucleotide sequences selected from SEQ ID NOs: 39-54.

In some embodiments, the polynucleotide molecule further comprises a 5' UTR structure. In some embodiments, the polynucleotide molecule comprises a 3'UTR structure. In some embodiments, the polynucleotide molecule further comprises a 5' UTR structure and a 3' UTR structure. In some embodiments, the 5' UTR structure comprises at least a polynucleotide sequence as shown in SEQ ID NO: 22 or SEQ ID NO: 25, or a polynucleotide sequence having at least 99%, 98%, 97%, 96%, 95%, 85%, or 80% sequence identity with SEQ ID NO: 22 or SEQ ID NO: 25. In some embodiments, the 5' UTR structure is a polynucleotide sequence as shown in SEQ ID NO: 22 or SEQ ID NO: 25, or a polynucleotide sequence having at least 99%, 98%, 97%, 96%, 95%, 85%, or 80% sequence identity with SEQ ID NO: 22 or SEQ ID NO: 25. In some embodiments, the 3' UTR structure comprises at least a polynucleotide sequence as shown in SEQ ID NO: 23 or SEQ ID NO: 26, or a polynucleotide sequence having at least 99%, 98%, 97%, 96%, 95%, 85%, or 80% sequence identity with SEQ ID NO: 23 or SEQ ID NO: 26. In some embodiments, the 3' UTR structure is a polynucleotide sequence as shown in SEQ ID NO: 23 or SEQ ID NO: 26, or a polynucleotide sequence having at least 99%, 98%, 97%, 96%, 95%, 85%, or 80% sequence identity with SEQ ID NO: 23 or SEQ ID NO: 26.

In some embodiments, the polynucleotide molecule is a mRNA molecule. In some embodiments, some or all of the uridine in the mRNA molecule is pseudouridine or 1-methyl-pseuduridine. In some embodiments, the mRNA further comprises a 5' cap structure. In some embodiments, the 5' cap structure is O type, I type, and II type. In some embodiments, the 5' cap structure is m7G(5')ppp(5')(2'-OMeA)pG. In some embodiments, the mRNA further comprises a poly (A) tail. In some embodiments, the poly (A) tail sequence comprises at least 20, at least 30, at least 40, at least 50, at least 60, at least 70, at least 80, at least 90, or at least 100 adenosines. In some embodiments, the poly (A) tail sequence comprises up to 500, up to 400, up to 300, up to 200, up to 150, up to 140, up to 130, up to 120, up to 110, up to 100, up to 90, up to 80, up to 70, and up to 60 adenosine (A) residues, particularly about 120 A. In some embodiments, the poly (A) tail comprises at least a polynucleotide sequence as shown in SEQ ID NO: 24 or SEQ ID NO: 27, or a polynucleotide sequence having at least 99%, 98%, 97%, 96%, 95%, 90%, 85%, or 80% sequence identity with SEQ ID NO: 24 or SEQ ID NO: 27. In some embodiments, the poly (A) tail is a polynucleotide sequence as shown in SEQ ID NO: 24 or SEQ ID NO: 27, or a polynucleotide sequence having at least 99%, 98%, 97%, 96%, 95%, 90%, 85%, or 80% sequence identity with SEQ ID NO: 24 or SEQ ID NO: 27.

In addition, the present application also provides a polynucleotide molecule comprising a polynucleotide sequence complementary to the polynucleotide sequence of the aforementioned polynucleotide molecules.

In some embodiments, the polynucleotide molecules provided in the present application may be single stranded molecules, double stranded molecules, or cyclic molecules. In some embodiments, the polynucleotide molecules provided in the present application comprise single and double stranded structures.

In the Second aspect, the present application also provides a fusion polypeptide. In some embodiments, the fusion polypeptide is encoded by a polynucleotide molecule as described in the first aspect. In some embodiments, the fusion polypeptide comprises at least:

1) an amino acid sequence A and an amino acid sequence B;
2) an amino acid sequence C, an amino acid sequence A, and an amino acid sequence B;
3) an amino acid sequence B and an amino acid sequence A;
4) an amino acid sequence C, an amino acid sequence B, and an amino acid sequence A;
5) an amino acid sequence A, an amino acid sequence B, and an amino acid sequence C;
6) an amino acid sequence B, an amino acid sequence A, and an amino acid sequence C;
7) an amino acid sequence A, an amino acid sequence C, and an amino acid sequence B or
8) an amino acid sequence B, an amino acid sequence C, and an amino acid sequence A, sequentially from the N-terminus to the C-terminus.

wherein, the amino acid sequence A comprises at least SEQ ID NOs: 1, 2, 3, 4 or variants thereof from the N-terminus to the C-terminus, and the amino acid sequences of each segment shown in the SEQ ID NO are directly connected sequentially or sequentially connected through a linker peptide;

the amino acid sequence B comprises SEQ ID NO: 5, 6, 7, 8 or variants thereof, and the amino acid sequences of each segment shown in the SEQ ID NO are directly connected sequentially or sequentially connected through linker peptides;

The amino acid sequence C comprises an HPV E2 antigen sequence.

Preferably, the variant is a conserved substitution variant.

In some embodiments, the amino acid sequence C is the HPV E2 antigen sequence.

In some embodiments, the HPV E2 antigen sequence is SEQ ID NO: 9.

In some embodiments, the linker peptide comprises one, two or more amino acid residues. In some embodiments, the linker peptide is a flexible linker peptide, a rigid linker peptide, or a combination thereof. In some embodiments, the amino acid sequences of each segment shown in the SEQ ID NO are connected by different linker peptides. In some embodiments, the amino acid sequences of each segment shown in the SEQ ID NO are connected by the same linker peptide. In some embodiments, the amino acid sequences of each segment shown in the SEQ ID NO are connected by two alanine residues.

In some embodiments, the fusion polypeptide comprises an amino acid sequence shown in SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21, or comprises a conservative substitution variant of the amino acid sequence shown in SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 or SEQ ID NO: 21, or comprises an amino acid sequence having at least 99%, 98%, 97%, 96%, 95%, 90%, 85%, or 80% sequence identity with the amino acid sequence shown in SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20 or SEQ ID NO: 21. In some embodiments, the fusion polypeptide comprises an amino acid sequence shown in SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21, or a conservative substitution variant of the amino acid sequence shown in SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21, or an amino acid sequences having 98%, 98.5%, 99%, 99.5% or more sequence identity with the amino acid sequence shown in SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21. In some embodiments, the fusion polypeptide is an amino acid sequence as shown in SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21.

In some embodiments, the fusion polypeptide further comprises the full length or functional domain of an immunostimulating factor peptide. In some embodiments, the immune stimulating factor protein or functional domain thereof is located at the C-terminus or N-terminus of the fusion polypeptide. In some embodiments, the immune stimulating factor is selected from one or more of the following: IL-3, IL-7, IL-2, IL-4, IL-5, IL-12, IL-13, Flt3L, G-CSF, M-CSF, GM-CSF, EPO, TPO, SCF, IFNα-2α, IFNα-2β, Pre-IFNα-2β, MIP-α, STING, MHSP70, an immune checkpoint inhibitor. In some embodiments, the immune stimulating factor is an antibody or antigen-binding fragment thereof targeting any one or more of the following checkpoint molecules: 2B4, 4-1BB, 4-1BB ligand, B7-1, B7-2, B7H2, B7H3, B7H4, B7H6, BTLA, CD155, CD160, CD19, CD200, CD27, CD27 ligand, CD28, CD40, CD40 ligand, CD47, CD48, CTLA-4, DNAM-1, galectin-9, GITR, GITR ligand, HVEM, ICOS, ICOS ligand, IDOI, KIR, 3DL3, LAG-3, OX40, OX40 ligand, PD-L1, PD-1, PD-L2, LAG3, PGK, SIRPα, TIM-3, PD-1, VSIG8. In some embodiments, the immune stimulating factor is Flt3L. In some embodiments, the polypeptide sequence of the immune stimulating factor comprises at least an amino acid sequence as shown in SEQ ID NO: 10, or a conserved substitution variant of SEQ ID NO: 10, or an amino acid sequence having at least 99%, 98%, 97%, 96%, 95%, 90%, 85%, or 80% sequence identity with SEQ ID NO: 10. In some embodiments, the polypeptide sequence of the immune stimulating factor is an amino acid sequence as shown in SEQ ID NO: 10, or a conserved substitution variant of SEQ ID NO: 10, or an amino acid sequence having at least 99%, 98%, 97%, 96%, 95%, 90%, 85%, or 80% sequence identity with SEQ ID NO: 10.

In some embodiments, the fusion polypeptide further comprises a signal peptide. In some embodiments, the signal peptide is located at the C-terminus or N-terminus of the fused peptide. In some embodiments, the signal peptide is a secretory signal peptide. In some embodiments, the secretory signal peptide is selected from the signal peptide of mammalian secretory proteins. In some embodiments, the mammal is human. In some embodiments, the secretory signal peptide is tPA-SP. In some embodiments, the secretory signal peptide comprises an amino acid sequence as shown in SEQ ID NO: 11, or a conserved substituent variant of SEQ ID NO: 11, or an amino acid sequence having at least 99%, 98%, 97%, 96%, 95%, 90%, 85%, or 80% sequence identity with SEQ ID NO: 11. In some embodiments, the secretory signal peptide is an amino acid sequence as shown in SEQ ID NO: 11, or a conserved substituent variant of SEQ ID NO: 11, or an amino acid sequence having at least 99%, 98%, 97%, 96%, 95%, 90%, 85%, or 80% sequence identity with SEQ ID NO: 11.

In some embodiments, the fusion polypeptide comprises sequentially connected coding sequence of the above signal peptide, the immune stimulating factor, and the fusion polypeptide from the N-terminus to the C-terminus.

In addition, the present application also provides a HPV E2 antigen polypeptide, a polynucleotide molecule encoding the HPV E2 antigen polypeptide, and use thereof. In some embodiments, the HPV E2 antigen polypeptide comprises or consists of an amino acid sequence as shown in SEQ ID NO: 9. In some embodiments, the amino acid sequence of the HPV E2 antigen polypeptide is shown in SEQ ID NO: 9. In some embodiments, the HPV E2 antigen polypeptide comprises or consists of a conserved substituent variant of SEQ ID NO: 9. The use of HPV E2 antigen polypeptides includes administering them in combination with other HPV antigen polypeptides to individuals in need, or administering it to individuals in need after fusing it with other HPV antigen polypeptides, in order to obtain a stronger immune response against HPV. The stronger immune response refers to an immune response that is stronger than that obtained by the individual when only administering the other HPV antigen polypeptides. In some embodiments, the polynucleotide molecule encoding the HPV E2 antigen polypeptide comprises or consists of a polynucleotide sequence as shown in SEQ ID NO: 38. In some embodiments, the polynucleotide molecule encoding the HPV E2 antigen polypeptide comprises or consists of a conserved substituent variant of a polynucleotide sequence as shown in SEQ ID NO: 38, or a nucleotide sequence having at least 99%, 98%, 97%, 96%, 95%, 90%, 85%, or 80% sequence identity with SEQ ID NO: 38. The use of the polynucleotide molecules encoding the HPV E2 antigen polypeptides includes administering them in combination with polynucleotide molecules encoding other HPV antigen polypeptides to individuals in need, or administering them to individuals in need after connecting their polynucleotide sequences with the sequences of polynucleotide molecules encoding other HPV antigen polypeptides to form new polynucleotide molecules, to express HPV E2 antigen polypeptides and other HPV antigen polypeptides, or the fusion protein of the HPV E2 antigen polypeptide and other HPV antigen polypeptides. In some embodiments, the individuals in need suffer from cervical cancer.

The third aspect of the present application provides a delivery system, comprising the polynucleotide molecule of the first aspect or the fusion polypeptide of the second aspect. In some embodiments, the delivery system may be a liposome, a viral particle, or a quantum dot. In some embodiments, the delivery system is LNP (a lipid nanoparticle). In some embodiments, the LNP comprises a PEG modified lipid, a non-cationic lipids, a sterol, an ionizable lipid, or any combination thereof. In some embodiments, the LNP consists of an ionizable lipid, a phospholipid, cholesterol, a polyethylene glycol (PEG)-lipid, and the polynucleotide molecule of the first aspect.

In some embodiments, the LNP comprises an ionizable lipid, a phospholipid, cholesterol, and a PEG lipid, wherein the content of the ionizable lipid is 35 mol %-65 mol %, the content of the sum of the phospholipid and cholesterol is 35 mol %-65 mol %, and the content of the PEG lipid is 0.5 mol %-5 mol %. In some embodiments, the LNP comprises an ionizable lipid, a phospholipid, cholesterol, and a PEG lipid. In the LNP, the content of the ionizable lipid is 40 mol %-50 mol %, the content of the phospholipid is 10 mol %-15 mol %, the content of cholesterol is 35 mol %-45 mol %, and the content of PEG lipid is 1.5 mol %-2.5 mol %.

The fourth aspect of the present application provides a cell comprising the polynucleotide molecule of the first aspect or the fusion polypeptide of the second aspect. In some embodiments, the cell is a bacterial, a fungal, or a mammalian cell.

The fifth aspect of the present application provides a pharmaceutical composition, pharmaceutical product or a kit comprising the polynucleotide molecule of the first aspect, a fusion polypeptide of the second aspect, a delivery system of the third aspect, and/or cells of the fourth aspect. In some embodiments, the pharmaceutical composition or pharmaceutical product is an mRNA vaccine, and it comprises mRNA from the polynucleotide molecule of the first aspect. In some embodiments, the mRNA is encoded by any one of the polynucleotides selected from SEQ ID NO: 28-54 or a nucleotide sequence having at least 99%, 98%, 97%, 96%, 95%, 90%, 85%, or 80% sequence identity with SEQ ID NO: 28-54. In some embodiments, the mRNA is encoded by any one of the polynucleotides selected from SEQ ID NO: 39-54 or a nucleotide sequence having at least 99%, 98%, 97%, 96%, 95%, 90%, 85%, or 80% sequence identity with SEQ ID NO: 39-54.

In some embodiments, the mRNA further comprises a 5' UTR structure. In some embodiments, the mRNA comprises a 3' UTR structure. In some embodiments, the mRNA further comprises a 5' UTR structure and a 3' UTR structure. In some embodiments, the 5' UTR structure comprises at least a polynucleotide sequence as shown in SEQ ID NO: 22 or SEQ ID NO: 25, or a polynucleotide sequence having at least 99%, 98%, 97%, 96%, 95%, 90%, 85%, or 80% sequence identity with SEQ ID NO: 22 or SEQ ID NO: 25. In some embodiments, the 5' UTR structure is a polynucleotide sequence as shown in SEQ ID NO: 22 or SEQ ID NO: 25, or a polynucleotide sequence having at least 99%, 98%, 97%, 96%, 95%, 90%, 85%, or 80% sequence identity with SEQ ID NO: 22 or SEQ ID NO: 25. In some embodiments, the 3' UTR structure comprises at least a polynucleotide sequence as shown in SEQ ID NO: 23 or SEQ ID NO: 26, or a polynucleotide sequence having at least 99%, 98%, 97%, 96%, 95%, 90%, 85%, or 80% sequence identity with SEQ ID NO: 23 or SEQ ID NO: 26. In some embodiments, the 3' UTR structure is a polynucleotide sequence as shown in SEQ ID NO: 23 or SEQ ID NO: 26, or a polynucleotide sequence having at least 99%, 98%, 97%, 96%, 95%, 90%, 85%, or 80% sequence identity with SEQ ID NO: 23 or SEQ ID NO: 26.

In some embodiments, the mRNA molecule of the present application is a mature mRNA molecule, which sequentially comprises a 5' cap, a 5' UTR, a coding sequence of the secretory signal peptide, a coding sequence of the immune stimulating factor, a coding sequence of the HPV antigen polypeptide, a 3' UTR, and a poly A tail from the 5' to 3 'end, wherein the 5' UTR, the coding sequence of the secretory signal peptide, the coding sequence of the immune stimulating factor, the coding sequence of the HPV antigen polypeptide, the 3' UTR, and the poly A tail are operably linked to each other. In some embodiments, the 5' cap is an m7G(5')ppp(5')(2'-OMeA)pG structure.

In some embodiments, the 5' end of the 5' UTR also comprises an AGG, AUG, or other nucleotide triplet; or 5' UTR and one or two bases on its 5' end together form an AGG, AUG, or other nucleotide triplet; for use in different capping systems. The starting sites required for different capping systems, e.g. Clean Cap AG, Clean Cap AU, etc., are known in the art and can be routinely selected by those skilled in the art.

In some embodiments, the mRNA molecule of the present application comprises a Kozak sequence. In some specific embodiments, the Kozak sequence comprises a GCCACC located on the 5' end of the coding sequence of the secretory signaling peptide.

In some embodiments, some or all of the uridine in the mRNA is chemically modified uridine. In some embodiments, some or all of the uridine in the mRNA is pseudouridine or 1-methyl-pseuduridine.

In some embodiments, some or all of the uracil nucleotides in the mRNA are substituted by pseudouridine (v) nucleotide or N1-methyl pseudouridine (ml) nucleotide.

In some embodiments, the mRNA further comprises a 5' cap structure. In some embodiments, the 5' cap structure is O type, I type, and II type. In some embodiments, the 5' cap structure is m7G(5')ppp(5')(2'-OMeA)pG. In some embodiments, the mRNA further comprises a poly (A) tail. In some embodiments, the poly (A) tail sequence comprises at least 20, at least 30, at least 40, at least 50, at least 60, at least 70, at least 80, at least 90, or at least 100 adenosines. In some embodiments, the poly (A) tail sequence comprises up to 500, up to 400, up to 300, up to 200, up to 150, up to 140, up to 130, up to 120, up to 110, up to 100, up to 90, up to 80, up to 70, or up to 60 adenosine (A) residues, particularly about 120 A. In some embodiments, the poly (A) tail comprises at least a polynucleotide sequence as shown in SEQ ID NO: 24 or SEQ ID NO: 27, or a polynucleotide sequence having at least 99%, 98%, 97%, 96%, 95%, 90%, 85%, or 80% sequence identity with SEQ ID NO: 24 or SEQ ID NO: 27. In some embodiments, the poly (A) tail is a polynucleotide sequence as shown in SEQ ID NO: 24 or SEQ ID NO: 27, or a polynucleotide sequence having at least 99%, 98%, 97%, 96%, 95%, 90%, 85%, or 80% sequence identity with SEQ ID NO: 24 or SEQ ID NO: 27.

In some embodiments, the pharmaceutical composition, pharmaceutical product or kit further comprises immune stimulating factors and/or adjuvants. In some embodiments, the immune stimulating factors are selected from one or more of the following: IL-3, IL-7, IL-2, IL-4, IL-5, IL-12, IL-13, Flt3L, G-CSF, M-CSF, GM-CSF, EPO, TPO, SCF, IFNα-2α, IFNα-2β, Pre IFNα-2β, MIP-α, STING, HSP70, immune checkpoint inhibitors, or the encoding polynucleotides thereof. In some embodiments, the STING is $STING^{V155M}$. In some embodiments, the immune checkpoint inhibitors are PD-1 inhibitors, PD-L1 inhibitors, or CTLA-4 inhibitors. In some embodiments, the encoding polynucleotide is mRNA.

The sixth aspect of the present application provides a method for treating or preventing HPV infection and HPV infection related diseases, including administering the polynucleotide molecule of the first aspect, the fusion polypeptide of the second aspect, the delivery system of the third aspect, the cell of the fourth aspect, or the pharmaceutical combination or pharmaceutical product of the fifth aspect to an individual. In some embodiments, the HPV infection related disease is cervical cancer. In some embodiments, the administration is intratumoral or peri-lymph nodes (i.e., subcutaneous at peri-lymph nodes) or intramuscular injection. In some embodiments, the method further comprises administering immune stimulating factors, chemotherapy, radiation therapy, and/or targeted therapy to an individual. In some embodiments, the targeted therapy refers to antibodies or functional domains thereof targeting specific tumor targets of cervical cancer.

It should be understood that the aspects and embodiments described herein include aspects and embodiments of "comprising", "consisting of", and "substantially consisting of . . . ". The preferred embodiments of the present application are detailed described above. However, the present application is not limited to this. Within the scope of the technical concept of the present application, various simple variations of the technical solutions can be made, including the combination of various technical features in any other suitable way. These simple variations and combinations should also be considered as the content disclosed in the present application, all of which fall within the scope of protection of the present application.

DETAIL DESCRIPTION OF THE INVENTION

Figure 1:
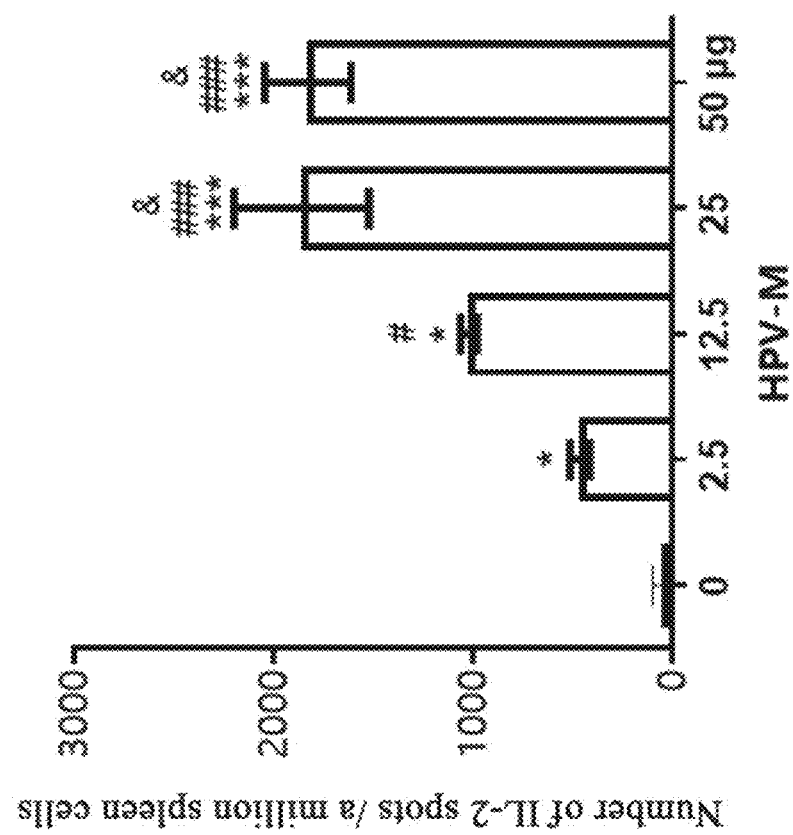
FIG. 1 shows the cellular immune response induced by different doses of HPV-M mRNA vaccines in normal mice.
Figure 1:
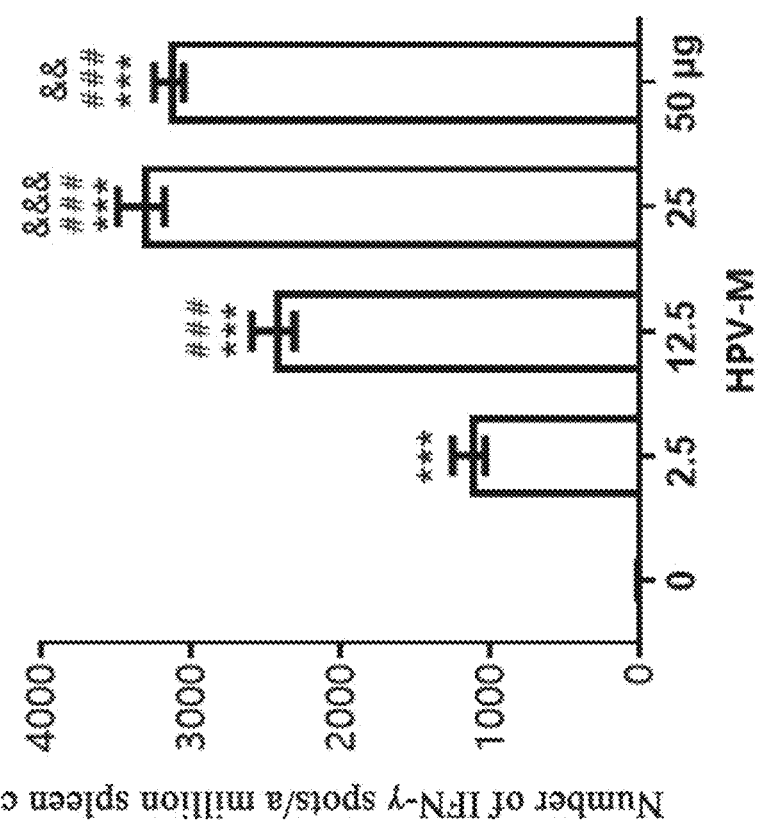
Figure 1:
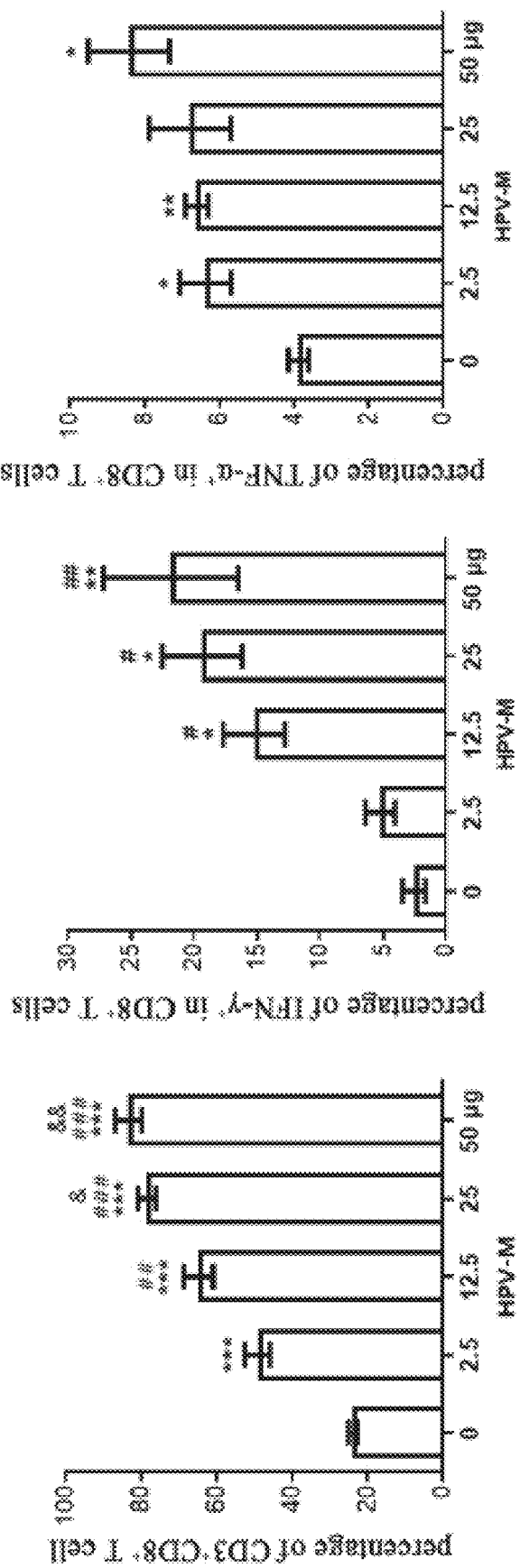

The present application provides a novel nucleotide sequence that can be used for the preparation of preventive or therapeutic nucleic acids and fusion polypeptides for HPV infection related diseases. Meanwhile, the present application also provides a pharmaceutical composition or pharmaceutical product comprising the therapeutic nucleic acid or fusion polypeptide, e.g. an mRNA vaccine, and use thereof for treating diseases.

Definitions

As used herein, "coding sequences" can refer to ribonucleotide sequences in mature mRNA that can be translated into proteins, as well as complementary sequences of deoxyribonucleotide (DNA) sequences used as templates to transcribe the ribonucleotide (RNA) sequence. In addition, the "coding sequence" of the present application may further comprise a polynucleotide sequence encoding functional nucleic acids, e.g. miRNA, shRNA, dsRNA, etc.

As used herein, the term "HPV E2 antigen sequence" is used to refer to the immunogenic amino acid sequence of E2 protein derived from HPV. In some embodiments, the HPV E2 antigen sequence comes from the E2 protein sequence of any wild-type or artificially mutated HPV subtype, or is a fusion protein of E2 protein sequences of multiple wild-type or artificially mutated HPV subtypes. In some embodiments, the HPV E2 antigen sequence is derived from a conserved peptide sequence of the HPV E2 protein, or is combination of two or more conserved peptide sequences. In some embodiments, the HPV E2 antigen sequence is a fusion protein of one or more conserved peptide sequences of the HPV E2 protein and specific E2 protein sequences of one or more wild-type and/or artificially mutated HPV subtypes. The conserved peptide sequence can be an intra genotype conserved peptide sequence, i.e., the conserved amino acid sequence in different variants of the E2 protein of a certain HPV subtype; it can also be a conserved peptide sequence between genotypes, i.e., a conserved amino acid sequence in multiple HPV subtype E2 proteins. The method for obtaining conservative peptide sequences (or conservative evaluation methods) is known in the art. Exemplarily, for example, usable full-length sequences of E2 proteins from different genotypes of HPV can be collected from protein databases such as NCBI and used as raw data input. All usable full-length sequences are used to ensure that the selected conserved peptide sequence will equivalently represent the entire environmental population. For example, before conservative evaluation, all genotypes are aligned and the sequences within each genotype are weighted to ensure an equivalent representation of genotype diversity and thus to ensure that HPV E2 antigen sequence candidates represent the entire environmental population. Then, a sliding window of 15 amino acids is used to evaluate the conservatism within the genotype (intra genotype conservatism), in order to determine the conservative values for each window based on the universality of amino acids within the combination window and the weighting of values for each sequence, in order to identify the fragments that are conserved within each genotype and the intra genotype conserved peptide sequences created for each window. 'The intra genotype conserved peptide sequence' refers to the amino acid sequence representing the weighted set of genotype sequences, rather than the most common amino acids at each position. To be classified as conservative, the window must have a conservative value within the first quartile of the conservative values of all windows in the protein. Subsequently, conserved intra genotype windows located at the same position across all genotypes are identified, regardless of the percentage identity of intra genotype standardized consensus sequences shared among genotypes (inter genotype conservation). Then, the phylogeny of the obtained region is created and the intra tree group sequences are combined to generate conserved peptide sequences between genotypes with high levels of shared identity.

As used herein, "linker peptide" refers to an amino acid residue in a fusion protein that connects two peptide fragments to each other, or a peptide chain containing two or more amino acid residues. In some embodiments, the linker peptide is a flexible linker peptide that allows the two amino acid fragments connected to have a certain degree of mobility. The addition of Ser and Thr can enable hydrogen bonds formed between the linker peptide and water molecules, endowing the linker peptide with stability in aqueous solution, thereby reducing the interaction between the linker peptide and the two proteins before and after them. The common flexible linker peptides are composed of Gly and Ser residues (GS linkers). In addition to the GS flexible linker peptide, there are also some other flexible linker peptides, such as (Gly); etc., which are known in the art. In some embodiments, the linker peptide is a rigid linker peptide that can be used to completely isolate two connected proteins and maintain their independent functions. Commonly used rigid linker peptides comprise a spiral structured peptide segments, (XP) n, etc., wherein P represents Proline and X can be any amino acid, preferably, Ala, Lys, Glu, and n represents the number of XP repetitions. Technicians in the art can independently adjust and select different linker peptides based on specific application scenarios and the 3D structure requirements of fusion proteins.

In the present application, "5' end" is used to describe the relative positional relationship between two segments of the same nucleotide sequence. Wherein, the "5' end" refers to the end of the polynucleotide sequence containing a free 5'-hydroxyl group. For example, "it further comprises encoding sequences of immune stimulating factors or their functional domains on the 5' end of the coding sequence of HPV antigen polypeptides" refers to "the encoding sequence of the immune stimulating factors or their functional domains" being closer to the 5' end of their common nucleotide sequence relative to "the encoding sequence of HPV antigen polypeptides".

The term "signal peptide" refers to a short peptide chain that guides the localization or transfer of newly synthesized proteins. Wherein, the signal peptide that guides the transfer of newly synthesized proteins to the secretion pathway is also known as the "secretory signal peptide". In most cases, the signal peptide is located at the N-terminus of the amino acid sequence. In mRNA, the coding sequence of the signal peptide is usually located after the starting codon, which is an RNA region that encodes a hydrophobic amino acid sequence. After the signal peptide guides the protein to complete localization, it is usually cleaved under the action of signal peptidase. The term "tPA-SP" refers to a tissue plasminogen activator signaling peptide, which is a secretory signal peptide.

As used herein, the "heterozygote of DNA and RNA sequences" is a polynucleotide sequence consisting of two kinds of nucleotides: DNA and RNA.

The term "5' cap" is located at the 5' end of mRNA and contains methylated guanosine. The methylated guanosine is attached to the 5' end of mRNA via pyrophosphate, forming a 5',5'-triphosphate linkage with its adjacent nucleotides. There are usually three types of 5' cap structures (m7G5'ppp5'Np, m7G5'ppp5'NmpNp, m7G5'ppp5' NmpNp), known as Type O, Type I, and Type II, respectively. Type O refers to the unmethylated ribose of the terminal nucleotide, type I refers to the methylated ribose of one terminal nucleotide, and type II refers to the methylated ribose of two nucleotides of the terminus. Herein, "Clean-Cap AG" is used to refer to m7G(5')ppp(5')(2'-OMeA)pG cap.

As used herein, the term "Poly (A) tail" or "Poly (A) sequence" refers to the uninterrupted or interrupted adenosine residue sequence typically located at the 3' end of RNA molecules. The Poly-A tail or Poly-A sequence is known to those skilled in the art and can be selected according to actual needs. In mRNA, in the presence of 3'-UTR, the Poly-A sequence is connected to the 3' end of the 3'-UTR. The characteristic of uninterrupted poly-A tail is the presence of continuous adenylate residues. The Poly-A tail can be of any length. In some embodiments, the Poly-A tail comprises or consists of at least 20, at least 30, at least 40, at least 80, or at least 100 and up to 500, up to 400, up to 300, up to 200, or up to 150 adenosine (A), particularly about 120 A. Usually, the vast majority of nucleotides in the Poly (A) tail are adenosines, wherein the vast majority refers to at least 75%, at least 80%, at least 85%, at least 90%, at least 95%, at least 96%, at least 97%, at least 98%, or at least 99% nucleotides, but allowing the remaining nucleotides to be nucleotides other than A, e.g. U (uridine), G (guanosine), or C (cytidine).

As used herein, the percentage "identity", such as 85%, 90%, 91%, 92%, 93%, 94%, 95%, 96%, 97%, 98%, 98.5%, 99%, 99.5% identity, refers to the degree of similarity between amino acid sequences or nucleotide sequences determined by sequence alignment, which is 85%, 90%, 91%, 92%, 93%, 94%, 95%, 96%, 97%, 98%, 98.5%, 99%, or 99.5%. For example, by introducing vacancies and other methods, two sequences can have the same residue in as many positions as possible, and the proportion of positions with the same base or amino acid residue to the total number of positions can be determined. The percentage "identity" can be determined using software programs known in the art. The preferred method is to use default parameters for alignment. A preferred alignment program is BLAST. The preferred programs are BLASTN and BLASTP. Details of these programs can be found at the following Internet address: ncbi.nlm.nih.gov/cgi-bin/BLAST.

As used herein, "complementarity" of nucleic acids refers to the ability of one nucleic acid to form hydrogen bonds with another through traditional Watson Crick base pairing. The percentage complementarity represents the percentage of residues in a nucleic acid molecule that can form hydrogen bonds (i.e., Watson Crick base pairing) with another nucleic acid molecule (for example, approximately 5, 6, 7, 8, 9, and 10 out of 10 are approximately 50%, 60%, 70%, 80%, 90%, and 100% complementary, respectively). "Complete complementarity" refers to the formation of hydrogen bonds between all consecutive residues of a nucleic acid sequence and the same number of consecutive residues in the second nucleic acid sequence. As used herein, "substantially complementary" refers to the degree of complementarity of any one of at least 70%, 75%, 80%, 85%, 90%, 95%, 96%, 97%, 98%, 99%, or 100% within a region of approximately 40, 50, 60, 70, 80,100,150, 200, 250, or more nucleotides, or two nucleic acids hybridized under strict conditions. For a single base or nucleotide, according to the Watson-Crick base pairing principle, when A pairs with T or U, C pairs with G or I, it is called complementary or matching, and vice versa; other base pairing is called non complementarity. The "complementary polynucleotide sequence" of a certain polynucleotide sequence in the present application refers to a polynucleotide sequence that is completely complementary to that particular polynucleotide sequence.

As used herein, "delivery system" refers to a structure formed by packaging or encapsulating larger biomolecules such as polynucleotides and polypeptides to form a structure with higher affinity for cell membranes and easier transmembrane transport from outside to inside of the cell. Delivery systems and their preparation methods are known in the art, including but not limited to liposomes (e.g. lipid nanoparticles (LNPs)), viruses (e.g. AAVs, lentiviruses), and quantum dots. The preparation method of LNPs is known in the art, such as those disclosed in CN114901360A and CN113941011A. In some embodiments, the LNPs comprises PEG modified lipids, non-cationic lipids, sterols, ionizable lipids, or any combination thereof.

As used herein, the term "immune stimulating factors" specifically refers to proteins, peptides, or nucleic acid molecules that can be produced within mammalian animals and enhance the immune system's antigen response, including but not limited to: cytokines that enhance abilities of immune cell processing and/or antigen presentation, e.g. dendritic cell growth factor (such as Flt3L); molecules that break immune suppression, including but not limited to immune checkpoint inhibitors; pro-inflammatory cytokines (such as granulocyte-macrophage colony-stimulating factor, IFNα-2a, IFNα-2β, Pre-IFNα-2β, IL-2), etc.

As used herein, the term "adjuvant" means exogenous substances that can be added to pharmaceutical compositions or formulations to enhance an individual's immune system's response to antigens, including but not limited to chemical adjuvants and bacterial antigens.

As used herein, "Flt3L" refers to the FMS-like tyrosine kinase 3 ligand. In some embodiments of the present application, the Flt3L is a human derived Flt3L, e.g. Flt3L recorded in the NCBI database with gene ID: 2323.

The term "immune checkpoint" refers to a molecule in the immune system that can turn on a signal (co-stimulatory molecule) or turn off a signal. Many cancers protect themselves from damage of immune system by inhibiting T cell signaling. As used herein, the term "immune checkpoint inhibitor" can help prevent this protective mechanism against cancer by acting on immune checkpoints. For example, immune checkpoint inhibitors can be antibodies or antigen-binding fragments thereof targeting any one or more of the following checkpoint molecules: 2B4, 4-1BB, 4-1BB ligand, B7-1, B7-2, B7H2, B7H3, B7H4, B7H6, BTLA, CD155, CD160, CD19, CD200, CD27, CD27 ligand, CD28, CD40 ligand, CD47, CD48, CTLA-4, DNAM-1, galectin-9, GITR, GITR ligand, HVEM, ICOS, ICOS ligand, IDOI. KIR, 3DL3, LAG-3, OX40, OX40 ligands, PD-L1, PD-1, PD-L2, LAG3, PGK, SIRPα, TIM-3, VSIG8. Wherein, "PD-1" (Programmed T Cell Death Receptor) is a transmembrane protein found on the surface of T cells. When binding to PD-L1 (Programmed T Cell Death Ligand 1) on tumor cells, it causes inhibition of T cell activity and decrease in T cell-mediated cytotoxicity. Therefore, PD-1 and PD-L1 are the "off switches" of immune downregulation or immune checkpoint signals.

In the present application, "immune checkpoint inhibitors" also include agonists of co-stimulatory molecules, such as agonists of CD28, CD122, and CD137, etc. CD28 is constitutively expressed on almost all human CD4+ T cells and approximately half of CD8+ T cells, promoting T cell expansion. CD122 can increase the proliferation of CD8+ effector T cells. 4-1BB (also known as CD137) is involved in T cell proliferation and can protect T cells, especially CD8+ T cells, from activation induced cell death by mediating signal transduction.

As used herein, "HPV infection related diseases" refer to any disease that is primarily or partially caused by human papillomavirus infection. Most HPV infections do not cause symptoms and can clear up on their own. However, in some cases, they persist and may lead to the appearance of common warts or precancerous lesions. In the present application, "HPV infection related diseases" include but are not limited to cervical cancer caused or partially caused by HPV. The methods for determining whether a certain disease is caused or partially caused by HPV are known in the art, such as judging by checking HPV infection history, detecting HPV antigens and/or antibodies in the patient's diseased tissue, blood, body fluids, or other related tissues or tissue fluids, etc. In the present application, HPV may cover any subtype of human papillomavirus, including but not limited to HPV16, HPV18, HPV31, HPV33, HPV35, HPV39, HPV45, HPV51, HPV52, HPV53, HPV54, HPV56, HPV58, and HPV59, etc.

As used herein, "mRNA" (messenger RNA) is any RNA that encodes at least one protein, a naturally occurring, non-naturally occurring, or modified amino acid polymer, and can be translated to produce the encoded protein in vitro, in vivo, in situ, or ex vivo. Technicians in the art should be aware that, unless otherwise specified, the polynucleotide sequence described in the present application may refer to thymine as "T" when referring to DNA sequences, but when the polynucleotide sequence represents RNA (e.g. mRNA), "T" will be replaced by "U" (Uridine). Therefore, any DNA disclosed and identified by a specific sequence number (SEQ ID NO) herein also discloses RNA (e.g. mRNA) sequences that complement or correspond to the DNA, wherein each "T" of the DNA sequence is replaced by "U".

As used herein, "open reading frame (ORF)" is a continuous DNA or RNA segment that starts with a starting codon (e.g. a methionine codon (ATG or AUG)) and ends with a termination codon (e.g. TAA, TAG or TGA, or UAA, UAG or UGA). ORF typically encodes proteins.

The terms "fusion polypeptide" and "fusion protein" used herein are interchangeable and should be understood as referring to a polypeptide that comprises a combination of sequences derived from different gene products (e.g. homologous proteins of different subtypes of HPV, different proteins of the same subtype of HPV, and non-homologous proteins of different subtypes of HPV) or a combination of sequences derived from the same gene product (e.g. a single HPV protein), wherein these sequences come from different/separate regions of wild-type gene products. For example, fusion polypeptides can comprise combinations of sequences that are typically separated by other wild-type sequence segments, as well as fusion bodies of the remaining peptide segments after removing one or more sequences.

As used herein, "at least comprising" means comprising or being. For example, "from N-terminal to C-terminal, at least sequentially comprise:
1) an amino acid sequence A and an amino acid sequence B;
2) an amino acid sequence C, an amino acid sequence A, and an amino acid sequence B;
3) an amino acid sequence B and an amino acid sequence A; or
4) an amino acid sequence C, an amino acid sequence B, and an amino acid sequence A" refers to:
a):
from N-terminal to C-terminal, it comprises:
"1) an amino acid sequence A and an amino acid sequence B;
2) an amino acid sequence C, an amino acid sequence A, and an amino acid sequence B;

3) an amino acid sequence B and an amino acid sequence A; or
4) an amino acid sequence C, an amino acid sequence B, and an amino acid sequence A", and one or more amino acids are further included between at least two adjacent amino acid sequences (e.g. sequences A and B, A and C, C and B); or b) from N-terminal to C-terminal, it comprises:
"1) an amino acid sequence A and an amino acid sequence B;
2) an amino acid sequence C, an amino acid sequence A, and an amino acid sequence B;
3) an amino acid sequence B and an amino acid sequence A; or
4) an amino acid sequence C, an amino acid sequence B, and an amino acid sequence A", and no more amino acid is included between any two adjacent amino acid sequences (e.g. sequences A and B, A and C, C and B).

As used herein, when "direct connection" is used to describe the relationship between two amino acid sequences, it means that there is no any other amino acid inserted between said two amino acid sequences; in some embodiments, "direct connection" refers to connecting the two amino acid sequences through chemical bonds; in some embodiments, "direct connection" refers to connecting the two amino acid sequences through peptide bonds (amide bonds).

Polynucleotide Sequence

In one aspect, the present application provides a polynucleotide sequence that can be used for prevention or treatment of HPV infection related diseases. Through extensive comparisons and experiments, the inventor ultimately determined that the polynucleotide sequence of the present application can induce a significant specific immune response against HPV in healthy mice, and shows significant anti-tumor activity in HPV positive tumor model mice.

The "variant" refers to a sequence or molecule that retains the same or substantially the same biological activity as the original sequence. The variant can come from the same or different species (e.g. homologous proteins from different mutant strains of the same HPV subtype), or can be synthetic sequences based on natural or existing molecules. In the present application, "variant" can be used to refer to variants of proteins, peptides, or amino acid sequences, as well as variants of nucleic acid molecules or polynucleotide sequences.

Those skilled in the art can easily identify variants of the above SEQ ID NOs: 1 to 9. For example, through sequence alignment, the segment positions of the amino acid sequences mentioned above can be determined in the corresponding protein amino acid sequences of the HPV subtype. The sequences in this segment of all mutant strains of HPV subtypes with mutations occurring in the segment positions are all variants corresponding to the amino acid sequences of each segment. Therefore, the amino acid sequence shown in SEQ ID NO: 1 or its variants comprise the E6 protein amino acid sequence corresponding to the first to the 85th amino acid sites of the E6 protein reference sequence (NCBI registration number QHA94929 or AAL96630.1) in the HPV16 subtype mutant strain; the amino acid sequence shown in SEQ ID NO: 2 or its variants comprise the E7 protein amino acid sequence corresponding to the first to the 65th amino acid sites of the E7 protein reference sequence (NCBI registration number ATI99837 or NP:041326.1) in HPV-16 subtype mutant strains, the amino acid sequence shown in SEQ ID NO: 3 or its variants comprise the E6 protein amino acid sequence corresponding to the 71st to the 158th amino acid sites of the E6 protein reference sequence in HPV-16 subtype mutant strains, the amino acid sequence shown in SEQ ID NO: 4 or its variants comprise the E7 protein amino acid sequence corresponding to the 51st to the 98th amino acid sites of the E7 protein reference sequence in the HPV-16 subtype mutant strain; the amino acid sequence shown in SEQ ID NO: 5 or its variants comprise the E6 protein amino acid sequence corresponding to the first to the 85th amino acid sites of the E6 protein reference sequence (NCBI registration number ABP99784) in the HPV-18 subtype mutant strain, the amino acid sequence shown in SEQ ID NO: 6 or its variants comprise the E7 protein reference sequence corresponding to the first to the 65th amino acid sites of the E7 protein reference sequence (NCBI registration number UZQ21949 or ABP99785.1) in the HPV-18 subtype mutant strain, the amino acid sequence shown in SEQ ID NO: 7 or its variants comprise the E6 protein amino acid sequence corresponding to the 71st to the 158th amino acid sites of the E6 protein reference sequence in the HPV-18 subtype mutant strain, and the amino acid sequence shown in SEQ ID NO: 8 or its variants comprise the E7 protein amino acid sequence corresponding to the 51st to the 105th amino acid sites of the E7 protein reference sequence in the HPV-18 subtype mutant strain. While the amino acid sequence shown in SEQ ID NO: 9 is formed by the fusion of multiple E2 proteins of HPV16, HPV18, and HPV31. The inventors of the present application have confirmed that the HPV E2 antigen sequence has the effect of enhancing the immunogenicity of HPV proteins.

In some embodiments, the "variant" of the amino acid sequence has at least one amino acid difference relative to the amino acid sequence, e.g. having at least one amino acid addition, insertion, deletion, or substitution. For example, the amino acid substitution can be conservative amino acid substitution, that is, replacing the original corresponding amino acid with an amino acid with similar properties. "Conservative substitution" can be polar to polar amino acids, such as glycine (G, Gly), serine (S, Ser), threonine (T, Thr), tyrosine (Y, Tyr), cysteine (C, Cys), asparagine (N, Asn), and glutamine (Q, Gln); non polar to non-polar amino acids, such as alanine (A, Ala), valine (V, Val), tryptophan (W, Trp), leucine (L, Leu), proline (P, Pro), methionine (M, Met), and phenylalanine (F, Phe); acidic to acidic amino acids, such as aspartic acid (D, Asp) and glutamic acid (E, Glu); alkaline to alkaline amino acids, such as arginine (R, Arg), histidine (H, His), and lysine (K, Lys); charged amino acids to charged amino acids, such as aspartic acid (D, Asp), glutamic acid (E, Glu), histidine (H, His), lysine (K, Lys), and arginine (R, Arg); hydrophobic to hydrophobic amino acids, such as alanine (A, Ala), leucine (L, Leu), isoleucine (I, Ile), valine (V, Val), proline (P, Pro), phenylalanine (F, Phe), tryptophan (W, Trp), and methionine (M, Met). In some other embodiments, the variant may also comprise non conservative substitutions. In some embodiments, the "variant" of the amino acid sequence may have sequence identity of at least about 70%, 75%, 80%, 85%, 90%, 95%, 96%, 97%, 98%, or 99% relative to the amino acid sequence. Comparing to the amino acid sequence, the "variant" of the amino acid sequence can have activity of at least 40%, 45%, 50%, 55%, 60%, 65%, 70%, 75%, 80%, 85%, 90%, 91%, 92%, 93%, 94%, 95%, 96%, 97%, 98%, 99%, or 100%, or within a range of any two of the aforementioned values. As used herein, a "conserved substitution variant" of a protein, peptide, or amino acid sequence refers to a variants with one or more amino acid residues substituted by amino acids without altering the overall conformation and function of the protein or enzyme, this includes but is not limited to replacing amino acids in the amino acid sequence of the parent protein in the manner described in the aforementioned "conservative substitution". Therefore, the similarity between two proteins or amino acid sequences with similar functions may differ. For example, 70% to 99% similarity (identity) based on the MEGALIGN algorithm. "Conservative substitution variants" also include peptides or enzymes that have more than 60% amino acid identity determined through BLAST or FASTA algorithms, preferably 75% or more, more preferably 85% or more, most preferably 90% or more, and they have same or basically similar properties or functions compared to natural or parental proteins or enzymes.

Therefore, the HPV antigen polypeptide and the fusion polypeptide described in the present application should encompass the aforementioned variants.

Those skilled in the art should be aware that variants of nucleic acid molecules or polynucleotide sequences encoding proteins comprise "synonymous mutants", which refer to nucleic acid molecules or polynucleotide sequences obtained by replacing one or more codons in the nucleic acid molecule or polynucleotide sequence with other codons encoding the same amino acid as the codon.

The term "at least comprising" refers to the fact that the polynucleotide sequence can consist of the coding sequence of the aforementioned HPV antigen polypeptide, or comprise other polynucleotide sequences besides the coding sequence comprising the HPV antigen polypeptide mentioned above.

For example, sequences that regulate the expression of the aforementioned HPV antigen polypeptides to make the polynucleotide more stable, as well as other polynucleotide sequences that can promote the stimulation of immune responses by the aforementioned HPV antigen polypeptides in the subject's body.

In some embodiments, the other polynucleotide sequences may use encoding sequences of any immune stimulating factor. The preferred immune stimulating factors include, for example, Flt3L.

The polynucleotide sequence can be a DNA sequence, an RNA sequence, or a hybrid of DNA and RNA sequences.

mRNA Vaccine

The present application also provides an mRNA vaccine for the prevention or treatment of HPV infection related diseases, wherein the mRNA vaccine comprises RNA sequences from the aforementioned polynucleotide sequences. The mRNA vaccine can achieve a preventive effect on immunity by introducing a polynucleotide sequence containing a polynucleotide encoding HPV antigen into the subject, directly translating it to form the corresponding antigen protein, inducing the body to produce a specific immune response. At the same time, it can also target and kill tumor cells containing HPV antigen.

The preparation method of mRNA vaccines is known in the art. Specifically, besides the aforementioned polynucleotide sequences, the mRNA in the mRNA vaccine further includes coding sequences for multiple necessary functional components to express, regulate, or enhance the expression level of the above HPV antigen polypeptides. The functional components include but are not limited to 5' caps, 5' UTRs, 3' UTRs, Poly (A) tails, etc. The functional components are known in the art, and those skilled in the art can choose and combine them according to actual needs. Both 5' UTR and 3' UTR are typically transcribed from genomic DNA and are elements present in pre-mature mRNA (also known as mRNA precursors or pre-mRNA). The characteristic structural features (e.g. the 5'-cap and 3'-Poly (A) tail) are typically added to transcribed (pre-mature) mRNA during mRNA processing. Therefore, in some embodiments, the mRNA is an mRNA precursor. In some embodiments, the mRNA is mature mRNA.

In some embodiments, the mRNA vaccine comprises the aforementioned RNA polynucleotide sequence(s), which has an open reading frame encoding at least one antigenic peptide with at least one modification and at least one 5' cap, and is formulated within lipid nanoparticles. According to the manufacturer's plan, the following chemical RNA cap analogues can be used to simultaneously complete 5' capping of polynucleotides during in vitro transcription reactions to produce 5'-guanosine cap structures: 3'-O-Me-m7G (5')ppp(5')G [ARCA cap], G(5')ppp(5')A, G(5')ppp(5')G, m7G(5')ppp(5')A, m7G(5')ppp(5')G (NewEnglandBioLabs, Ipswich, MA), or m7G(5')ppp(5')(2'-OMeA)pG (CleanCa-pAG). The cowpox virus capping enzyme can be used to complete the 5' capping of the modified RNA after transcription to produce a type O cap structure: m7G(5')ppp (5')G (New England BioLabs, Ipswich, MA). Both cowpox virus capping enzyme and 2'-O-methyl-transferase can be used to produce type I cap structures to produce m7G(5') ppp(5')(2'-OMeA)pG, which can also be produced by the Cleancap method. Beginning from the type I cap structure, the Type II cap structure can be produced by using 2'-O-methyl transferase to perform 2'-O-methylation on the 5'-the third to last nucleotide. Beginning from the type II cap structure, the type III cap structure can be produced by using 2'-O-methyl transferase to 2'-O-methylation on the 5'-the fourth to last nucleotide.

The 3'-Poly (A) tail is usually added to the 3' end of the transcribed mRNA. In some embodiments, it may comprise up to about 400 adenine nucleotides. In some embodiments, the length of the 3'-Poly (A) tail can be an essential element for the stability of individual mRNA.

In some embodiments, the mRNA also comprises stabilizing elements. Stabilizing elements may include, for example, histone stem loops. In some embodiments, the mRNA comprises a coding region, at least one histone stem loop, and optionally a Poly (A) sequence or polyadenylation signal. The Poly (A) sequence or polyadenylation signal should typically enhance the expression level of the encoded protein. In some embodiments, the mRNA comprises a combination of a Poly (A) sequence or polyadenylation signals with at least one histone stem loop, although the two have alternative mechanisms in nature, their synergistic effect can increase protein expression to levels beyond those observed by any individual element. The synergistic effect of the combination of Poly (A) with at least one histone stem loop does not depend on the order of the elements or the length of the Poly (A) sequence. In some embodiments, the histone stem loop is typically derived from the histone gene, and includes two adjacent parts separated by intervals (consisting of short sequences) or a loop formed by the intramolecular base pairing of completely reverse complementary sequences. Unpaired loop regions typically cannot pair with any one of the stem loop elements. The stability of the stem loop structure usually depends on its length, the number of mismatched or protruding parts, and the base composition of the pairing region. In some embodiments, swinging base pairing (non Watson Crick base pairing) can be produced. In some embodiments, at least one histone stem loop sequence comprises length of 15 to 45 nucleotides. In some embodiments, the mRNA does not comprise histone downstream elements (HDE). The "histone downstream element (HDE)" comprises purine riched polynucleotide segments of approximately 15 to 20 nucleotides located at the 3' end of the naturally occurring stem loop, representing the binding site of U7 snRNA involved in processing histone pre-mRNA into mature histone mRNA.

In some embodiments, one or more AU rich sequences of the mRNA may be removed. These sequences are sometimes referred to as AURES, which are destabilized sequences discovered in 3' UTR. AURES can be removed from mRNA. Alternatively, AURES can be retained in mRNA.

In some embodiments, the mRNA is configured within lipid nanoparticles (LNPs). In some embodiments, lipids are mixed with the mRNA to form lipid nanoparticles. In some embodiments, RNA is prepared in lipid nanoparticles. In some embodiments, the lipid nanoparticles first form empty lipid nanoparticles and are combined with or encapsulate the mRNA of the vaccine shortly before administration (e.g. within a few minutes to an hour).

The lipid nanoparticles typically contain ionizable lipids, non-cationic lipids, sterols, and PEG lipid components, as well as nucleic acid target, e.g. the aforementioned mRNA. The lipid nanoparticles disclosed herein can be produced using components, compositions, and methods commonly known in the art, see e.g. PCT/US2016/052352, PCT/US2016/068300, PCT/US2017/037551, PCT/US2015/027400, PCT/US2016/047406, PCT/US2016/000129, PCT/US2016/014280, PCT/US2016/014280, PCT/US2017/038426, PCT/US2014/027077, PCT/US2014/055394, PCT/US2016/052117, PCT/US2012/069610, PCT/US2017/027492, PCT/US2016/059575 and PCT/US2016/069491, all of which are incorporated herein by reference as a whole.

In some embodiments, the mRNA vaccine may further comprise one or more adjuvants. Adjuvants are known in the art and can be selected based on specific antigens and disease conditions. Exemplary adjuvants comprise: aluminum salt adjuvants (such as aluminum hydroxide or aluminum phosphate solution), nucleic acid adjuvants (such as CpG-ODN), lipid containing adjuvants (such as LPS), mixed adjuvants (such as MF59, Freund's adjuvants), and aggregate structure adjuvants (such as RAM1, RAM2, RAM3).

Pharmaceutical Compositions or Pharmaceutical Products

The pharmaceutical composition or pharmaceutical product provided in the present application comprises the aforementioned polynucleotide sequence, nucleic acid molecule, delivery system or cells containing the polynucleotide sequence, fusion polypeptides encoded by the aforementioned polynucleotide sequence, or mRNA vaccines, wherein, the nucleic acid molecules, delivery systems, cells, fusion polypeptides, and mRNAs in mRNA vaccines have purity that meets clinical needs.

Alternatively, the pharmaceutical composition or pharmaceutical product of the present application may further comprise one or more other active compounds according to the needs of the specific indications treated. Preferably, the compound has complementary, auxiliary, or promoting effects on the aforementioned nucleic acid molecules, delivery systems, cells, and fusion polypeptides, such as enhancing the ability of the nucleic acid molecules, delivery systems, cells, or fusion polypeptides to induce an immune response, or compounds that enhance the immune system's immune response to the nucleic acid molecules, delivery systems, cells, or fusion polypeptides without adversely affecting each other. Such compounds can exist in the desired amount for the desired purpose in the pharmaceutical composition or pharmaceutical product. For example, in some embodiments, the other active compounds may include one or more immune stimulating factors, e.g. Flt3L, granulocyte-macrophage colony stimulating factor, IFN α-2α. IFN α-2β, Pre-IFN α-2β, IL-2, as well as immune checkpoint inhibitors such as PD-1 or PD-L1 antibodies.

The above-mentioned active ingredients, e.g. nucleic acid molecules, delivery systems, cells, fusion polypeptides, etc., can be sandwiched or encapsulated in delivery systems or colloidal drug delivery systems, e.g., be sandwiched or encapsulated in liposomes, albumin microspheres, microemulsions, nanoparticles, or nanocapsules. When the pharmaceutical composition or pharmaceutical product comprises two or more active ingredients, the active ingredients can be mixed with each other or separated from each other, e.g. co-existing in the same delivery system, colloidal particles, or microcapsules, or separately existing in different delivery systems, colloidal particles, or microcapsules.

And alternatively, the pharmaceutical composition or pharmaceutical product further comprises one or more pharmaceutically acceptable carriers, excipients, or stabilizers (Remington: Remington: The Science and Practice of Pharmacy 20th edition (2000)), appearing in the form of aqueous solutions, lyophilized agents or other desiccants. The pharmaceutically acceptable carriers, excipients, or stabilizers are non-toxic to subjects at the dosage and concentration used, they include buffering agents (such as phosphate, citrate, histidine, and other organic acids), antioxidants (including ascorbic acid and methionine), preservatives, low molecular weight (less than about 10 amino acid residues) peptides, proteins (such as serum albumin, gelatin, or immunoglobulin); hydrophilic polymers, such as polyvinylpyrrolidone. Amino acids (such as glycine, glutamine, asparagine, histidine, arginine, or lysine); monosaccharides, disaccharides, and other carbohydrates (including glucose, mannose, or dextrin); chelating agents (such as EDTA), polysaccharides (such as sucrose, mannose, trehalose, or sorbitol); salt forming counterions (such as sodium); metal complexes; non-ionic surfactants (such as TWEEN™, PLURONICS™ or polyethylene glycol). Sustained release formulations can be prepared. A suitable example of sustained release formulations comprises a semi permeable matrix containing a solid hydrophobic polymer of the present application's immunoglobulin, which is in the form of a isomer, such as film or microcapsule.

It should be understood that the present application includes various aspects, embodiments, and combinations of said aspects and/or embodiments described herein. The above description and subsequent Examples are intended to illustrate rather than limit the scope of the present application. Other aspects, improvements, and modifications within the scope of the present application will be apparent to those skilled in the art. Therefore, ordinary skilled in the art should recognize that the scope of the present application also comprises the improvements and modifications to the aspects and embodiments described.

EXAMPLES

Example 1. Sequence Construction and Preparation of HPV Vaccine 1.1 Synthesis of HPV Vaccine Sequence and Construction of Recombinant Vector In this Example, the antigen sequence of the mRNA vaccine for HPV related tumor is the E6 and E7 proteins of HPV types 16 and 18, and their coding fragments are concatenated to obtain the polynucleotide sequence. From the 5' end, the encoding nucleotide sequence sequentially comprises: T7 promoter with XbaI at the 5' end, 5' UTR, tPA-SP, Flt3L, HPV E2 (if any), E6/E7 protein or variants thereof, 3' UTR and/or Poly (A) tail were digested by restriction endonuclease XbaI and NotI, and ligated with the pUC57-GW-Kan (GENEWIZ) vector skeleton fragment that was digested by XbaI and NotI to construct a recombinant plasmid. In Examples 1-6, the nucleic acid sequence component 1 is used, and the ORF encoding sequence is SEQ ID NOs: 47-48, SEQ ID NOs: 50-52, and SEQ ID NO: 54; In Examples 7-8, nucleic acid sequence component 2 is used, and the ORF encoding sequence is SEQ ID NO: 49, SEQ ID NO: 53, and SEQ ID NO: 54.

1.2 mRNA Preparation 1.2.1 Plasmid Linearization

The recombinant plasmid constructed in step I has a SapI restriction site after the last A in the poly (A) tail sequence. The plasmid containing the target gene was linearized using the restriction endonuclease SapI. The reaction system is shown in Table 1, and digested at 37° C. for 3 hours.

TABLE 1

| enzyme digestion system for plasmid linearization | |
| --- | --- |
| 10 × Cutsmart Buffer | 5 μL |
| SapI enzyme (10000 U/mL) | 1 μL |
| plasmid | 10 μg |
| ddH$_2$O | Complete to 50 μL |

2 μL of digestion products was taken and subjected to 1% agarose gel electrophoresis to detect the linearization of plasmids. The linearized plasmids were purified using PCR product recovery kit (CWBIO).

1.2.2 In Vitro Transcription and Purification

The linearized recombinant plasmid obtained in step (1) was used as the template for in vitro transcription, and a high-yield T7 RNA transcription kit was used for in vitro transcription. High Yield T7 RNA Transcription Kit, product name: High Yield T7 RNA Synthesis Kit, Shanghai Hongene Bioengineering Co., Ltd., product catalog number: ON-040; 5x Reaction Buffer, 100 mM ATP Solution, 100 mM CTP Solution, 100 mM GTP Solution, Enzyme Mix, DNase I, Ammonium Acetate Stop Solution, Lithium Chloride (LiCl) Precision Solution are all components of the High Yield T7 RNA Transcription Kit. 100 mM Y UTP Solution (pseudouridine triphosphate), the full name is N1-Me-pUTP, 100 mM, is produced by Shanghai Hongene Bioengineering Co., Ltd., with product catalog number R5-027. Each ingredient (taking a 20 μL reaction system as an example) was added according to the following system (Table 2), mixed well and reacted at 37° C. for 3 hours.

TABLE 2

| In vitro transcription system | |
| --- | --- |
| 5 × Reaction Buffer | 4 μL |
| ATP(100 mM) | 2 μL |
| ΨTP(100 mM) | 2 μL |
| CTP(100 mM) | 2 μL |
| GTP(100 mM) | 2 μL |
| Enzyme mix | 1 μL |

TABLE 2-continued

| In vitro transcription system | |
| --- | --- |
| Linearized DNA template | 500 ng-1μg |
| CleanCap AG (100 mM) | 1 μL |
| nuclease free H$_2$O | Complete to 20 μL |

Among them, CleanCap AG is m7G(5')ppp(5')(2'-OMeA) pG, item number ON-134, from Shanghai Hongene Bioengineering.

When the transcription reaction is completed, 1 μL DNase I was added, reacted at 37° C. for 15 minutes, 15 μL Ammonium Acetate Stop Solution was added, mixed well. Afterwards, ⅓ volume of 7.5 M Lithium Chloride (LiCl) Precipitation Solution was added (to a final concentration of 2.5 M) and kept at −20° C. for 30 minutes, centrifuged at 12000 g for 15 minutes, RNA was precipitated at the bottom and the supernatant was discarded. 1 mL of 70% ethanol was added to clean the RNA, centrifuged at 12000 g for 5 minutes, and the supernatant was discarded. After air drying, 50 μL of RNase free water was added to dissolve the precipitation, and the mRNA was quantified using a UV spectrophotometer to obtain capped in vitro transcribed mRNA.

1.3 Lipid Nanoparticles (LNP) Encapsulation

The mRNA stock solution obtained in step 1.2 was dispersed into a 20 mM acetic acid solution (pH 5.0) to obtain an RNA solution with mRNA concentration of 200 μg/mL. A lipid mixture was obtained by mixing according to the molar ratio of ionizable lipids: cholesterol:DSPC:DMG-PEG2000=50:38.5:10:1.5. The flow rate of the water and oil phases was controlled through a T-mixing method to mix mRNA and the lipid mixture, the injection pump was started to make the mRNA solution mix with the lipid mixture to form LNP. Then, the solution was diluted by 10 times with the diluent, after centrifugation and concentration through an ultrafiltration tube, performed three rounds of solution displacement. The solution obtained above was added to Tris aqueous solution and adjusted to pH 7.0~8.0 to obtain mRNA solution encapsulated in LNP. LNP refers to lipid nanoparticles.

The concentration and particle size of mRNA encapsulated in LNP were measured using the Ribogreen RNA quantification kit (Invitrogen, R11490) and the Darwin ZetaSizer particle size analyzer, respectively. LNP without any substance encapsulated was used as control in the experiments.

Example 2. Cellular Immunological Dose Effect Evaluation of HPV-M mRNA Vaccine 25 SPF grade 6-8 weeks old female C57BL/6 mice were randomly divided into 5 groups, with 5 mice in each group. According to the grouping shown in Table 4, the mice were immunized with mRNA vaccines every two weeks for a total of three times. 7 days after immunization, the mice were sacrificed, the spleens were taken and placed on a 70 μm cell nylon filter, and were thoroughly ground into a cell suspension in 2 ml of RPMI-1640 complete culture medium, and cell counting was performed.

TABLE 3

Grouping of mice for detection of vaccine cell immune response

| vaccine candidates | Dosage | Immunization method | Number of mice |
|---|---|---|---|
| HPV-M | 2.5 μg | intramuscular injection | 5 |
| HPV-M | 12.5 μg | intramuscular injection | 5 |
| HPV-M | 25 μg | intramuscular injection | 5 |
| HPV-M | 50 μg | intramuscular injection | 5 |
| LNP | 50 μg | intramuscular injection | 5 |

2.1 Levels of HPV16- and HPV18-E6, E7-Specific IFN γ and IL-2 Detected by ELISpot The cells were inoculated into the ELISpot plate at $1.5 \times 10^5$ cells per well, then overlapping peptide library of E6 and E7 proteins of HPV16 and HPV 18 (synthesized by SBS Company) was added. The peptides comprise 15 amino acid sequences, wherein 8 amino acid residues overlap with each consecutive peptide. PMA and ionomycin positive stimulants were added to the positive control well, while no stimulants were added to the negative control well. Then the plate was placed in a 5% $CO_2$ incubator and incubated at 37° C. for 20 hours. According to the instructions of the ELISpot assay kit (Dacron, 2210001 and Mabtech, 2210001), the cells in the plate were subjected to antibody and coloration incubation. After air drying, the plate was read using the Mabtech IRIS ELISpot/FluoroSpot reader equipped with Mabtech Apex software (version 1.1.45.114), and the spot forming units (SFUs) in the plate were detected.

2.2 Flow Cytometry Detection of HPV16- and HPV18-E6, E7-Specific T Cell Responses In order to comprehensively evaluate the cellular immune response induced by the HPV vaccines mentioned above, intracellular cytokine staining assay was also performed. After breaking the red blood cells, the obtained monoplasts were filtered, and inoculated at $1 \times 10^6$ cells per well in 96 well U-bottom cell culture plate(s). The overlapping peptide library of E6 and E7 proteins of HPV16 and HPV18 (synthesized by SBS Company) or PMA and Ionomycin were used as stimulators, BFA and monenemycin (Biolegend, 420601 and 420701) were used as blockers. After overnight incubation in a 37° C., 5% $CO_2$ incubator, extracellular staining (CD3-cy5.5, CD4-APC or FITC, and CD8-APC or FITC) was first conducted, followed by cell membrane rupture and fixation, and then intracellular cytokine IFN-γ-PE or TNF-α-PE staining. The cells obtained were detected using Cytoflex flow cytometry (Beckman coulter). The levels of IFN-γ and TNF-α in CD4+ and CD8+ cells were obtained by gating cells.

Significance analysis of each experimental group and control group was performed by using One-way ANOVA statistical method (*** $p<0.001$ vs. LNP group; ### $p<0.001$ vs. HPV-M-2.5 μg; ## $p<0.01$ vs. HPV-M-2.5 μg; && $p<0.01$ vs. HPV-M-12.5 μg; & $p<0.05$ vs. HPV-M-12.5 μg). As shown in FIG. 1, both Elispot and flow cytometry results showed that the cellular immune response produced by HPV-M showed a dose-dependent effect, reaching the platform period after a dose of 25 μg.

Example 3. Pharmacodynamic Evaluation of HPV-M mRNA Vaccine

3.1 Antitumor Effects after Intramuscular or Intratumoral Injection of HPV-M Vaccine This study used the TC-1 mouse tumor model to evaluate the pharmacodynamic effects of the HPV-M vaccine. SPF grade 6-8 weeks female C57BL/6 mice were subcutaneously inoculated with logarithmic growth phase TC-1 cells. When the volume of the tumor reached 100 mm³, the mice were randomly divided into groups based on the tumor volume, with 10 mice in each group. According to the grouping shown in Table 4, the mice were immunized with mRNA vaccines once a week for three times. The tumor size was measured twice a week and the survival status of the mice was recorded. The tumor volume was calculated according to the following formula: volume of the implanted tumor=long diameter×short diameter×short diameter/2, that is, $V=ab^2/2$. Statistical analysis was performed on tumor volume and survival rate among groups using One-way ANOVA and Log-rank, respectively.

TABLE 4

Grouping of mice for pharmacodynamic evaluation of HPV-M vaccine

| Vaccine candidates | Dosage | Immunization method | Number of mice |
|---|---|---|---|
| HPV-M | 6.25 μg | intramuscular injection | 10 |
| HPV-M | 12.5 μg | intramuscular injection | 10 |
| HPV-M | 25 μg | intramuscular injection | 10 |
| LNP Ctrl | 25 μg | intramuscular injection | 10 |
| HPV-M | 6.25 μg | intratumoral injection | 10 |
| HPV-M | 12.5 μg | intratumoral injection | 10 |
| HPV-M | 25 μg | intratumoral injection | 10 |
| LNP Ctrl | 25 μg | intratumoral injection | 10 |

Figure 2:
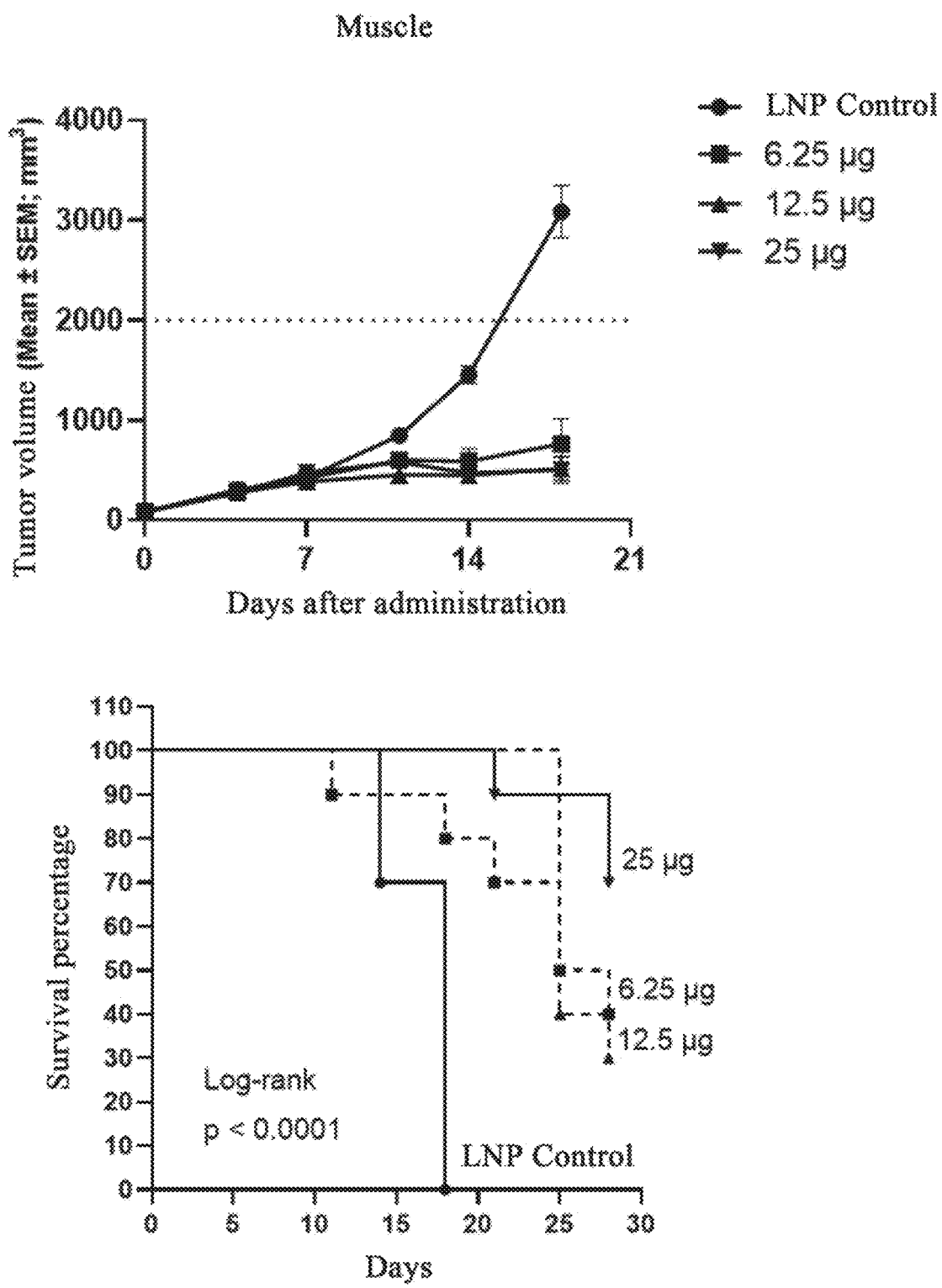
FIG. 2: The anti-tumor effect of TC-1 tumor model mice after intramuscular or intratumoral injection of HPV-M mRNA vaccine.
Figure 2:
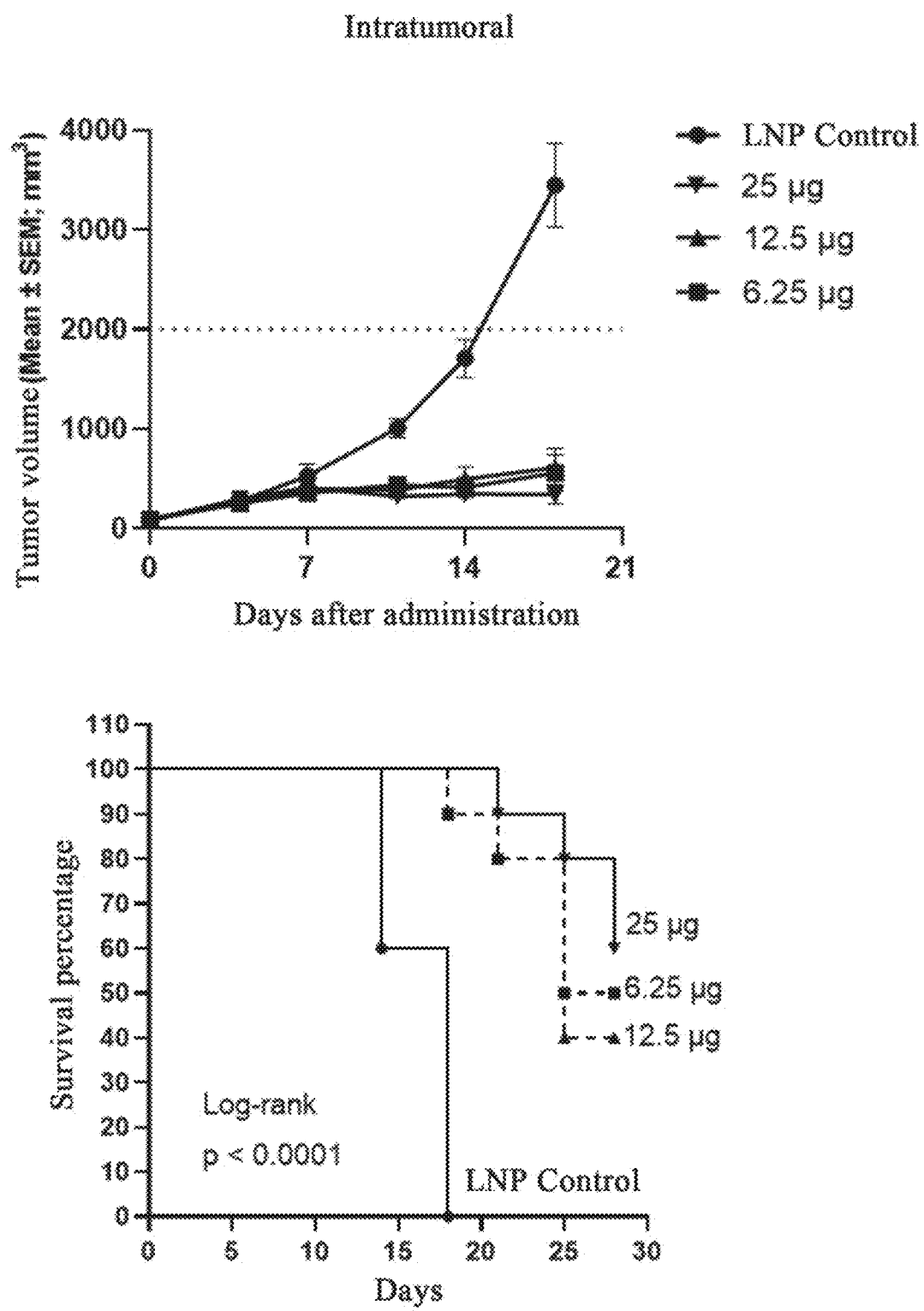

As shown in FIG. 2, on the TC-1 mouse tumor model, regardless of intramuscular or intratumoral injection, compared with the mice treated with LNP as the control group, the average tumor volume of mice treated with HPV-M at each dose group was significantly decreased, and the survival period of mice was also significantly prolonged.

3.2 Antitumor Effects of HPV-M Vaccine Injected into Muscles or Peri-Lymph Nodes Near Tumors According to the evaluation method for anti-tumor effects mentioned above, mice were immunized with mRNA vaccines according to the grouping shown in Table 5.

TABLE 5

Grouping of mice for pharmacodynamic evaluation of HPV-M vaccine

| Vaccine candidates | Dosage | Immunization method | Number of mice |
|---|---|---|---|
| HPV-M | 6.25 μg | intramuscular injection | 10 |
| HPV-M | 12.5 μg | intramuscular injection | 10 |
| HPV-M | 25 μg | intramuscular injection | 10 |
| LNP Ctrl | 25 μg | intramuscular injection | 10 |
| HPV-M | 6.25 μg | peri-lymph nodes injection | 10 |
| HPV-M | 12.5 μg | peri-lymph nodes injection | 10 |
| HPV-M | 25 μg | peri-lymph nodes injection | 10 |
| LNP Ctrl | 25 μg | peri-lymph nodes injection | 10 |

Figure 3:
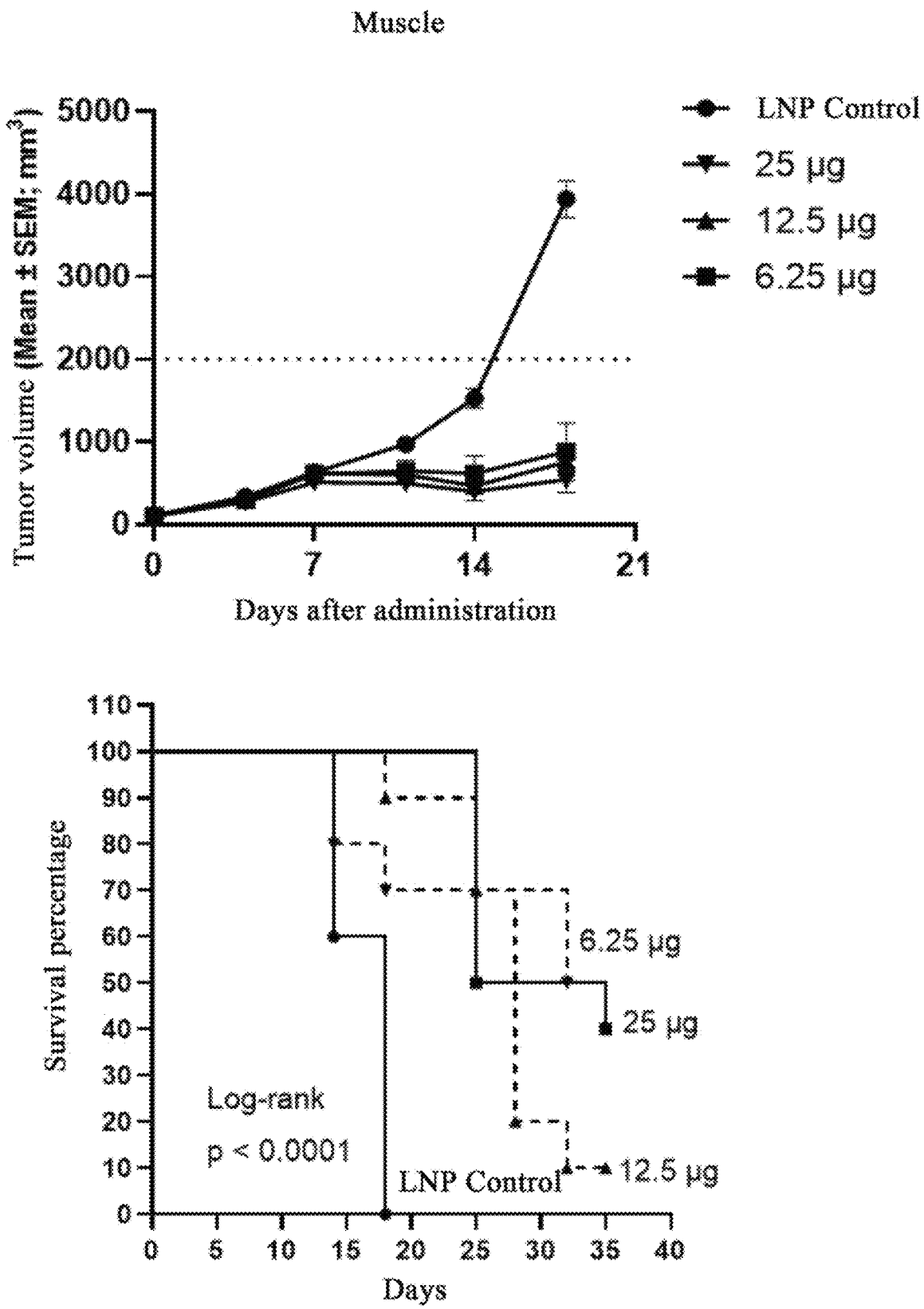
FIG. 3: The anti-tumor effect of HPV-M mRNA vaccine injected into muscles or peri-lymph nodes near the tumor in TC-1 tumor model mice.
Figure 3:
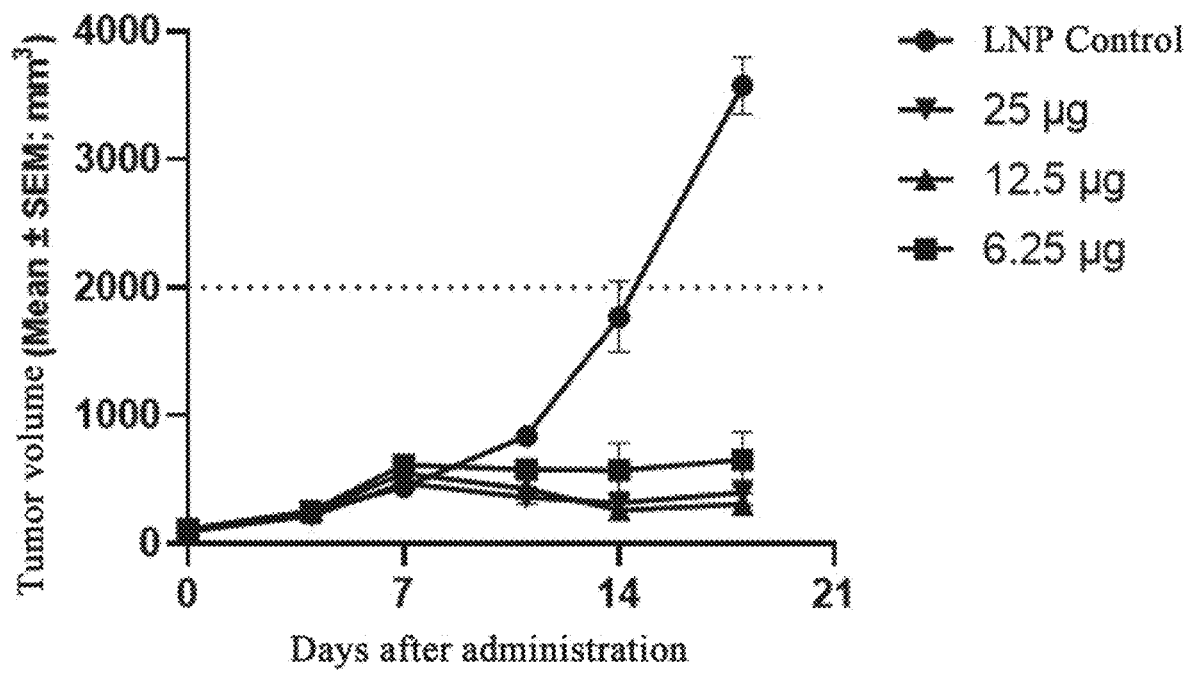
Figure 3:
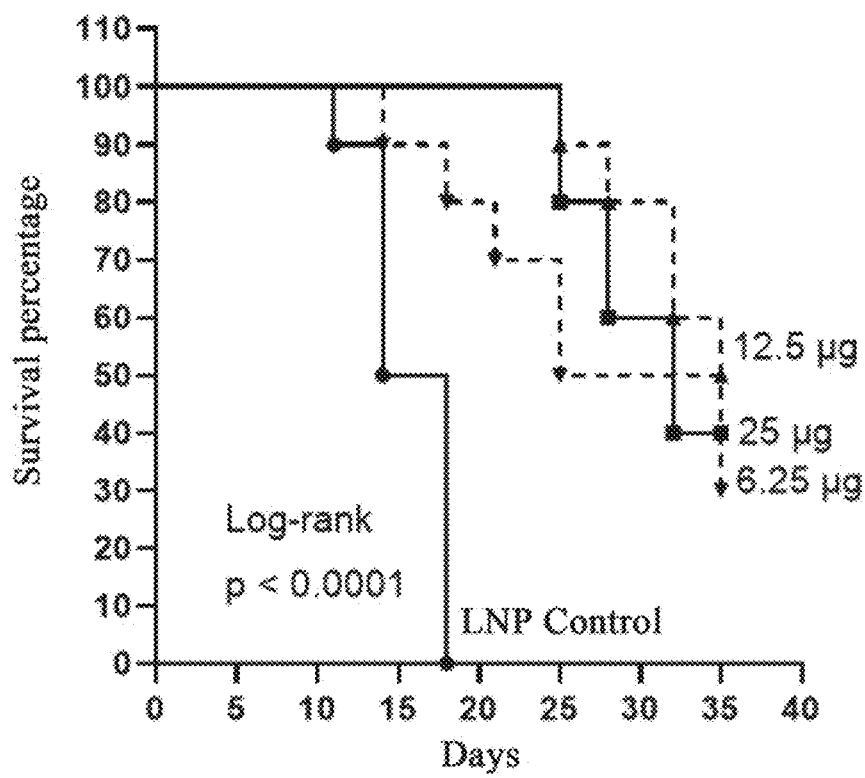

As shown in FIG. 3, on the TC-1 mouse tumor model, regardless of intramuscular or peri-lymph nodes injection, compared with the mice treated with LNP as the control group, each dose group of HPV-M significantly inhibited tumor growth and significantly prolonged mouse survival.

Example 4. Cellular Immune Evaluation of Different HPV mRNA Vaccines in Mice after Vaccination 35 SPF grade 6-8 weeks female C57BL/6 mice were randomly divided into 7 groups, with 5 mice in each group.

According to the grouping shown in Table 4, the mice were immunized with mRNA vaccines once every two weeks for twice. 7 days after the immunization, the mice were sacrificed, and the spleens were taken and placed on a 70 μm cell nylon filter, and were thoroughly ground into a cell suspension in 2 ml of RPMI-1640 complete culture medium, and cell counting was performed.

TABLE 6

Grouping of mice for detection of vaccine cell immune response

| Vaccine candidates | Dosage | Immunization method | Number of mice |
|---|---|---|---|
| HPV-1 | 5 μg | intramuscular injection | 5 |
| HPV-2 | 5 μg | intramuscular injection | 5 |
| HPV-3 | 5 μg | intramuscular injection | 5 |
| HPV-4 | 5 μg | intramuscular injection | 5 |
| HPV-M | 5 μg | intramuscular injection | 5 |
| LNP | 5 μg | intramuscular injection | 5 |

4.1 Levels of HPV16- and HPV18-E6, E7-Specific IFN γ and IL-2 Detected by ELISpot The levels of antigen-specific IFN-γ and IL-2 induced by the above five HPV vaccines were detected using the same ELISpot method as that in Example 2.

Figure 4:
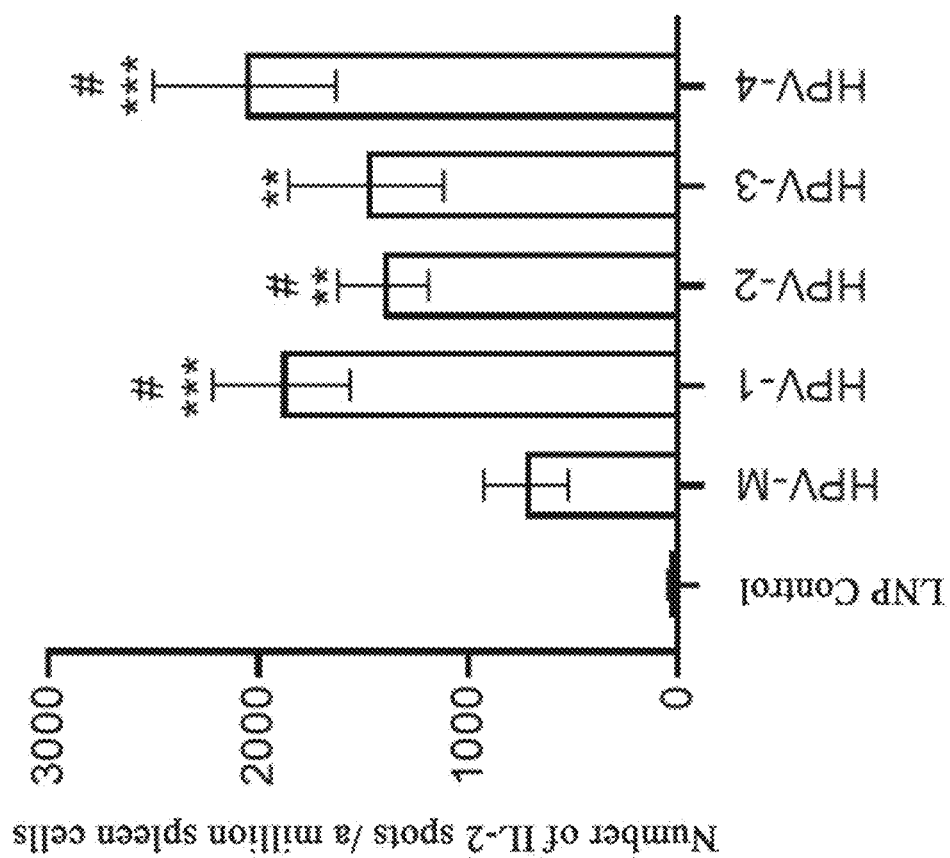
FIG. 4: the HPV16- and HPV18-E6, E7-specific IFNγ and IL-2 levels induced by two injections of immunization with 5 different mRNA vaccines (5 μg) are detected by ELISpot.
Figure 4:
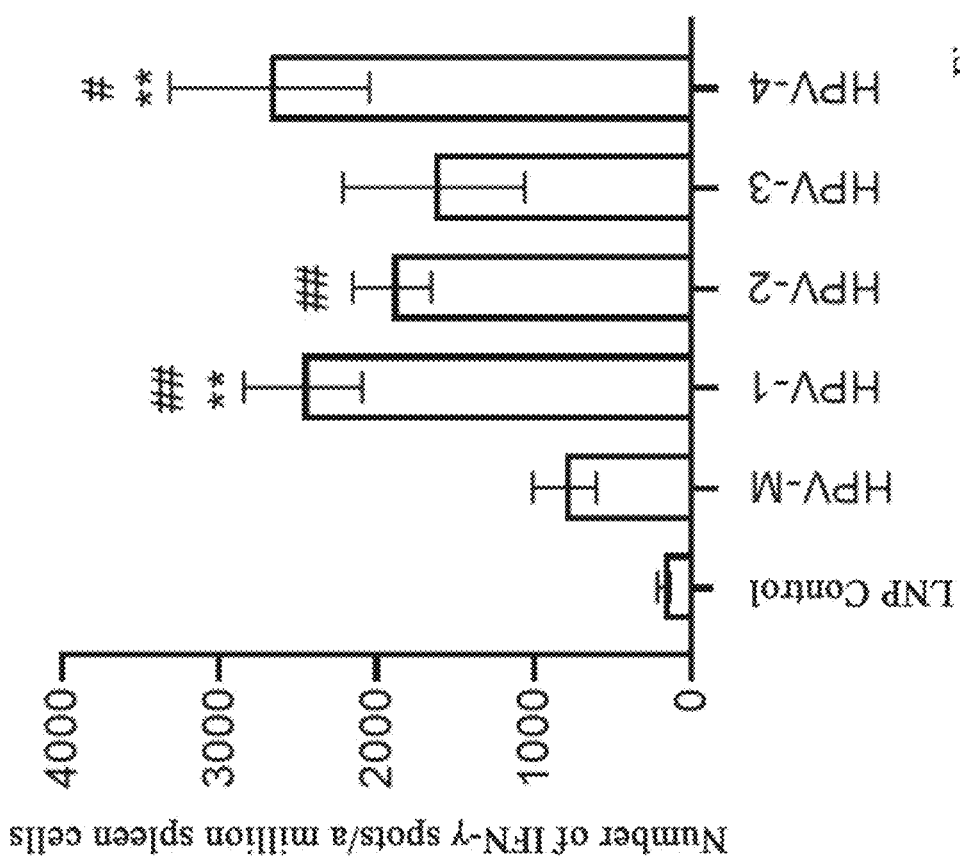

As shown in FIG. 4, when immunizing with low doses of 5 μg for two shots, the average spot size of IFN-γ and IL-2 of SFU/$10^6$ spleen cells from mice in five experimental groups was higher than that of the negative control group. Compared with the HPV-M vaccine group, the HPV-1, HPV-2, HPV-3, and HPV-4 vaccine groups all significantly increased the levels of IFN-γ and IL-2 expressed by mouse spleen cells stimulated by specific peptides, and effectively induced antigen-specific cellular immune responses. One-way ANOVA statistical analysis of the significance among each group was performed using GraphPad Prism 8 software (* $p<0.001$ vs. LNP control;  $p<0.01$ vs. LNP control; * $p<0.05$ vs. LNP control; ###$p<0.001$ vs. HPV-M; ##$p<0.01$ vs. HPV-M; #$p<0.05$ vs. HPV-M).

Figure 5:
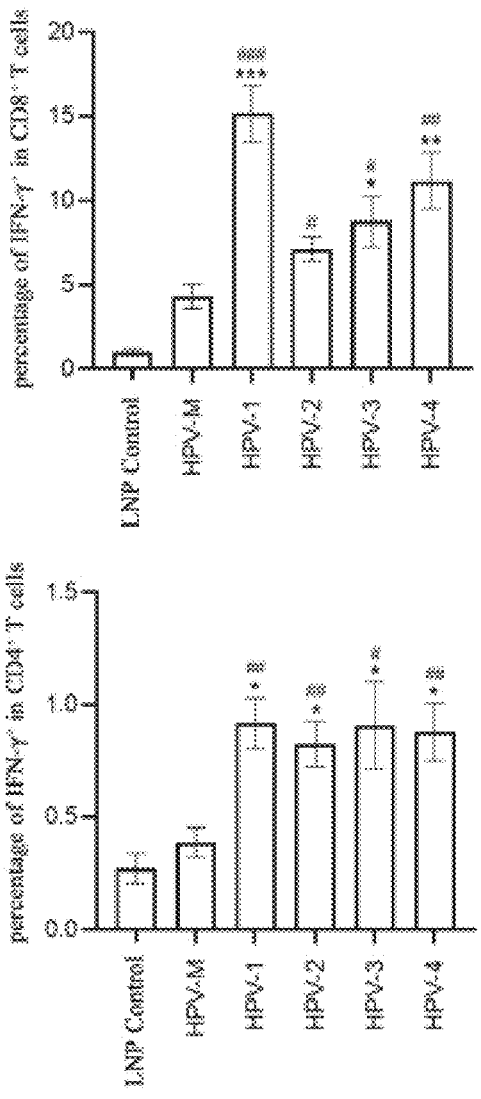
FIG. 5: the HPV16- and HPV18-E6, E7-specific T cell response induced by two injections of immunization with 5 different mRNA vaccines (5 μg) are detected by flow cytometry.
Figure 5:
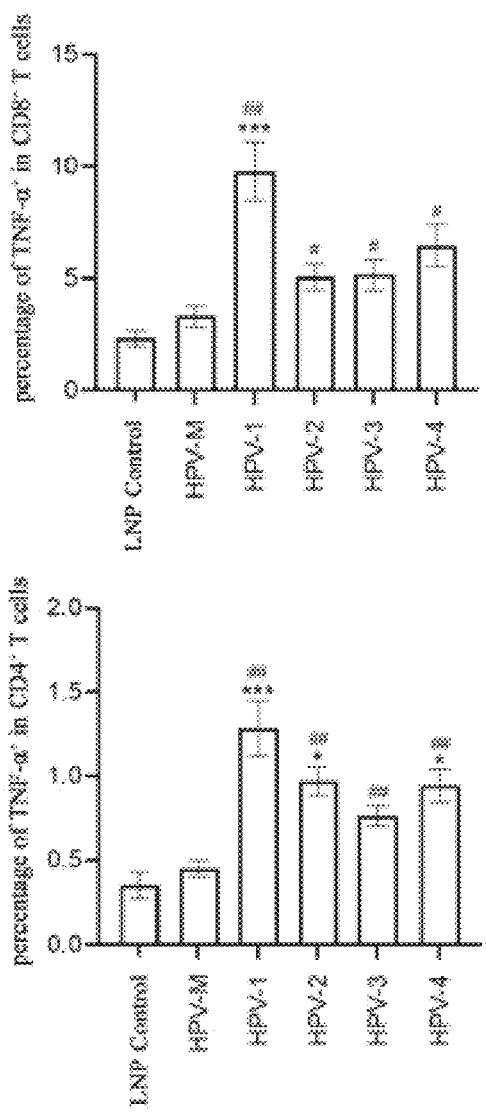

4.2 Flow Cytometry Detection of HPV16- and HPV18-E6, E7-Specific T Cell Responses Simultaneously, the antigen-specific T cell responses induced by the above five HPV vaccines' immunization were detected by the same flow cytometry method as in Example 2. By gating cells to obtain levels of IFN-γ and TNF-α in CD4+ and CD8+ cells, the significance analysis of each experimental group and control group was performed using One-way ANOVA statistical method, and the student t-test was used to pairwise compare the experimental group and the HPV-M original sequence group. As shown in FIG. 5, when immunizing with low dose of 5 μg for two shots, the percentages of IFN-γ and TNF-α in CD4+ and CD8+ cells of mouse spleen cells in the four experimental groups HPV-1, HPV-2, HPV-3, and HPV-4 were significantly higher than those of the HPV-M vaccine group, indicating that vaccination can successfully induce an effective immune response. One-way ANOVA statistical analysis of the significance among each group was performed using GraphPad Prism 8 software (* $p<0.001$ vs. LNP control;  $p<0.01$ vs. LNP control; * $p<0.05$ vs. LNP control; ###$p<0.001$ vs. HPV-M; ##$p<0.01$ vs. HPV-M; #$p<0.05$ vs. HPV-M).

Example 5. Cellular Immune Evaluation of Different HPV mRNA Vaccines in Mice after Vaccination 25 SPF grade 6-8 weeks female C57BL/6 mice were randomly divided into 7 groups, with 5 mice in each group. According to the grouping shown in Table 4, the mice were immunized with mRNA vaccines once every two weeks for a total of three times. 7 days after the immunization, the mice were sacrificed, and the spleens were taken and placed on a 70 μm cell nylon filter, and were thoroughly ground into a cell suspension in 2 ml of RPMI-1640 complete culture medium, and cell counting was performed.

TABLE 7

Grouping of mice for detection of vaccine humoral immune response

| Vaccine candidates | Dosage | Immunization method | Number of mice |
|---|---|---|---|
| HPV-1 | 12.5 μg | intramuscular injection | 5 |
| HPV-4 | 12.5 μg | intramuscular injection | 5 |
| HPV-5 | 12.5 μg | intramuscular injection | 5 |
| HPV-M | 12.5 μg | intramuscular injection | 5 |
| LNP | 12.5 μg | intramuscular injection | 5 |

5.1 Levels of HPV16- and HPV18-E6, E7-Specific IFN γ and IL-2 Detected by ELISpot Levels of the antigen-specific IFN-γ and IL-2 induced by the above four HPV vaccines were detected using the same ELISpot method as that in Example 2.

Figure 6:
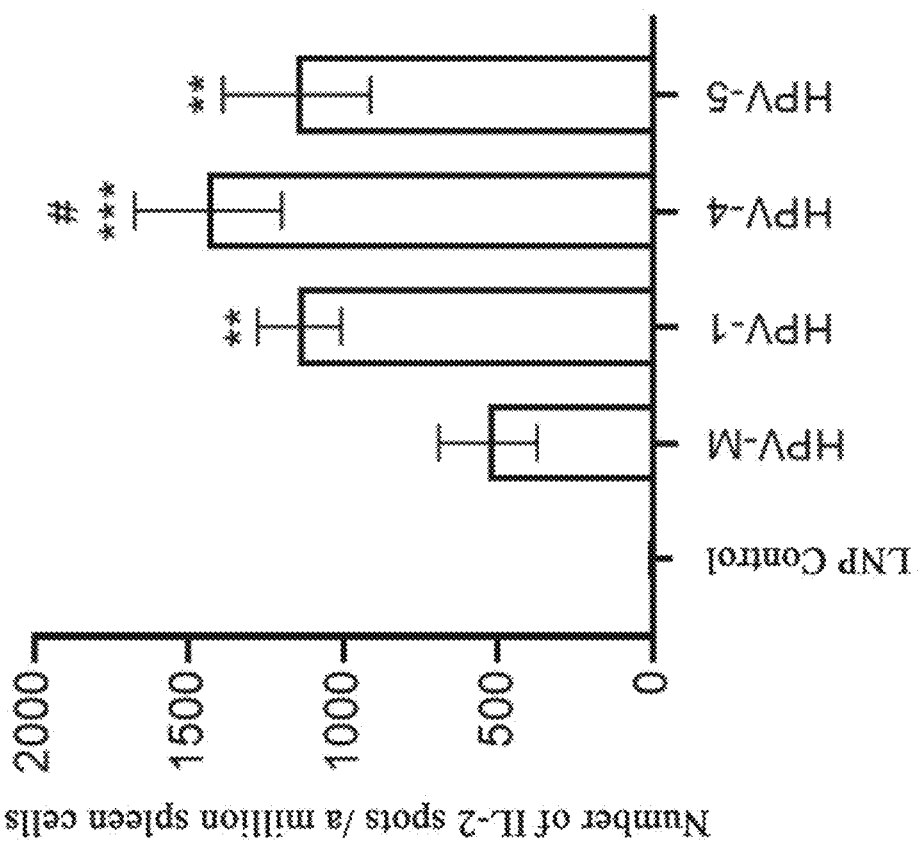
FIG. 6: the HPV16- and HPV18-E6, E7-specific IFNγ and IL-2 levels induced by three injections of immunization with of 4 different mRNA vaccines (12.5 μg) are detected by ELISpot.
Figure 6:
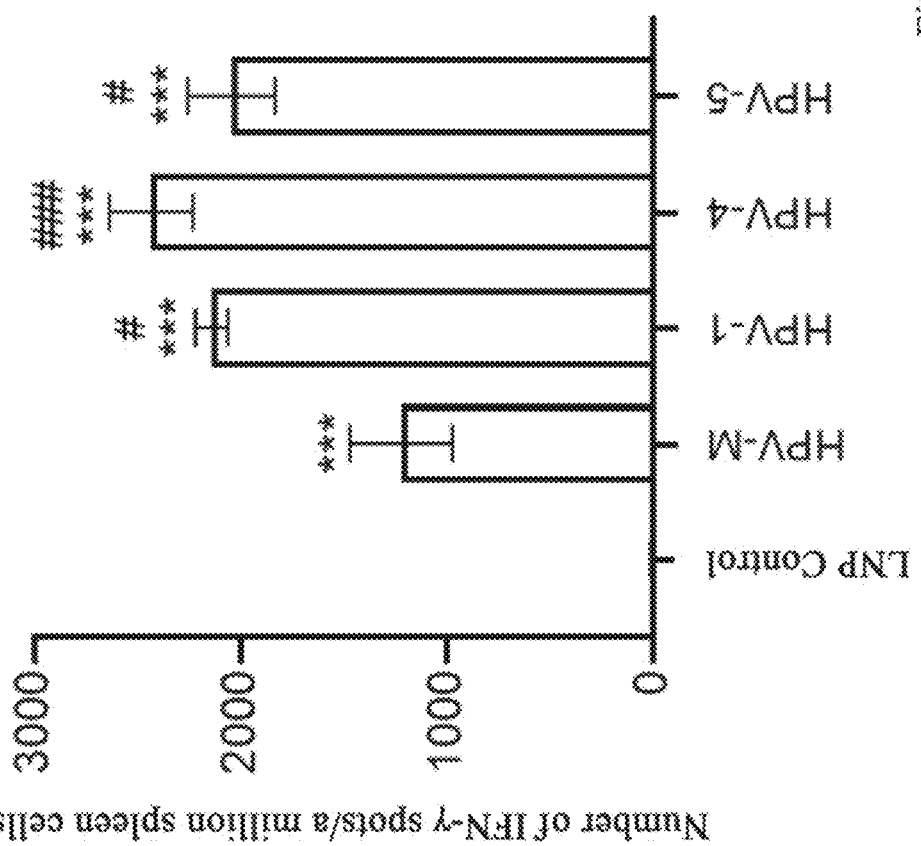

As shown in FIG. 6, when immunizing at dosage of 12.5 μg for three shots, the average spot size of IFN-γ and IL-2 of SFU/$10^6$ spleen cells of mice in the four experimental groups was higher than that of the negative control group. Compared with the HPV-M vaccine group, the HPV-1, HPV-4, and HPV-5 vaccine groups all significantly increased the levels of IFN-γ and IL-2 expressed by mouse spleen cells stimulated by specific peptides, indicating that these three vaccines significantly enhanced antigen-specific cellular immune responses. One-way ANOVA statistical analysis of the significance among each group was performed using GraphPad Prism 8 software (* $p<0.001$ vs. LNP control;  $p<0.01$ vs. LNP control; * $p<0.05$ vs. LNP control; ###$p<0.001$ vs. HPV-M; ##$p<0.01$ vs. HPV-M; #$p<0.05$ vs. HPV-M).

Figure 7:
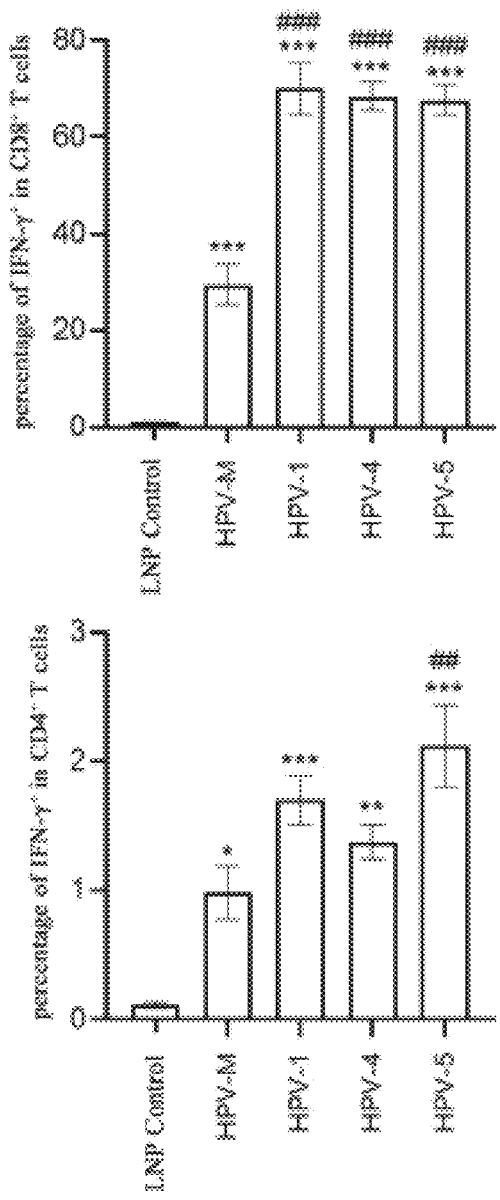
FIG. 7: the HPV16- and HPV18-E6, E7-specific T cell response induced by three injections of immunization with 4 different mRNA vaccines (12.5 μg) are detected by flow cytometry.
Figure 7:
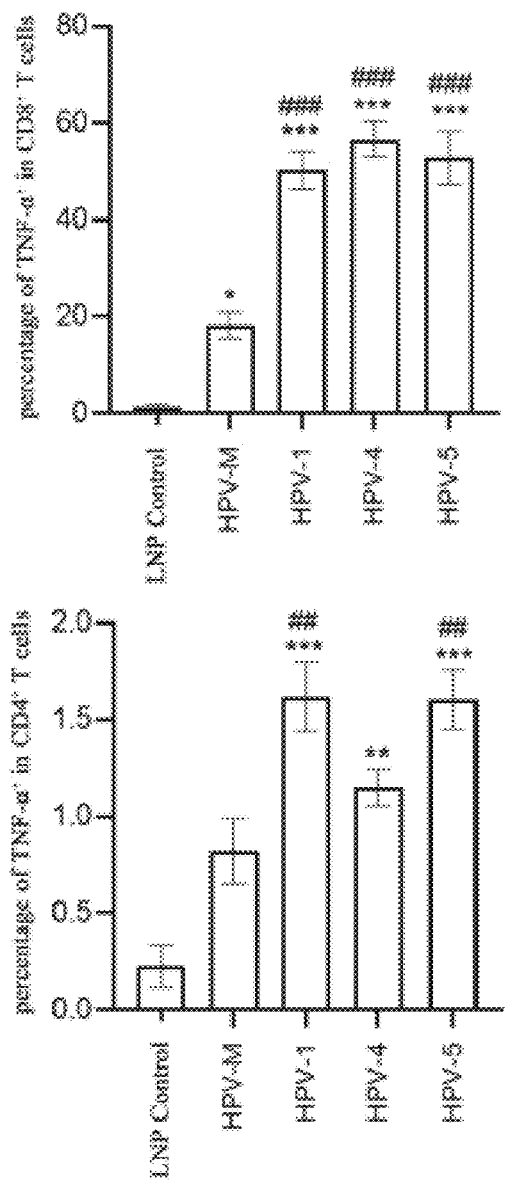

5.2 Flow Cytometry Detection of HPV16- and HPV18-E6, E7-Specific T Cell Responses Simultaneously, the antigen-specific T cell responses induced by the above four HPV vaccines were detected by the same flow cytometry method as in Example 2. By gating cells to obtain levels of IFN-γ and TNF-α in CD4+ and CD8+ cells, the significance analysis of each experimental group and control group was performed using One-way ANOVA statistical method. As shown in FIG. 7, when immunizing with dosage of 12.5 μg for three shots, the percentages of IFN-γ and TNF-α in CD4+ and CD8+ cells of mouse spleen cells in the four experimental groups were significantly higher than those of the negative control group. Compared with the HPV-M vaccine group, HPV-1, HPV-4, and HPV-5 all significantly increased the percentage of IFN-γ and TNF-α in CD8+ cells, further indicating that these three vaccines can induce stronger antigen-specific cellular immune responses than HPV-M vaccines. One-way ANOVA statistical analysis of the significance among each group was performed using GraphPad Prism 8 software (* p<0.001 vs. LNP control;  p <0.01 vs. LNP control; * p<0.05 vs. LNP control; ###p<0.001 vs. HPV-M; ##p<0.01 vs. HPV-M; #p<0.05 vs. HPV-M).

Example 6. Antitumor Effects of Different HPV mRNA Vaccines in TC-1 Mouse Tumor Model This study used the same method as that in Example 3 to evaluate the pharmacodynamic effects of different HPV mRNA vaccines in TC-1 mouse tumor model. mRNA vaccines were administered to mice according to the grouping shown in Table 8.

TABLE 8

Grouping of mice for pharmacodynamic evaluation of HPV-M vaccine

| Vaccine candidates | Dosage | Immunization method | Number of mice |
| --- | --- | --- | --- |
| HPV-1 | 12.5 μg | intramuscular administration | 10 |
| HPV-4 | 12.5 μg | intramuscular administration | 10 |
| HPV-5 | 12.5 μg | intramuscular administration | 10 |
| HPV-M | 12.5 μg | intramuscular administration | 10 |
| LNP | 12.5 μg | intramuscular administration | 10 |

Figure 8:
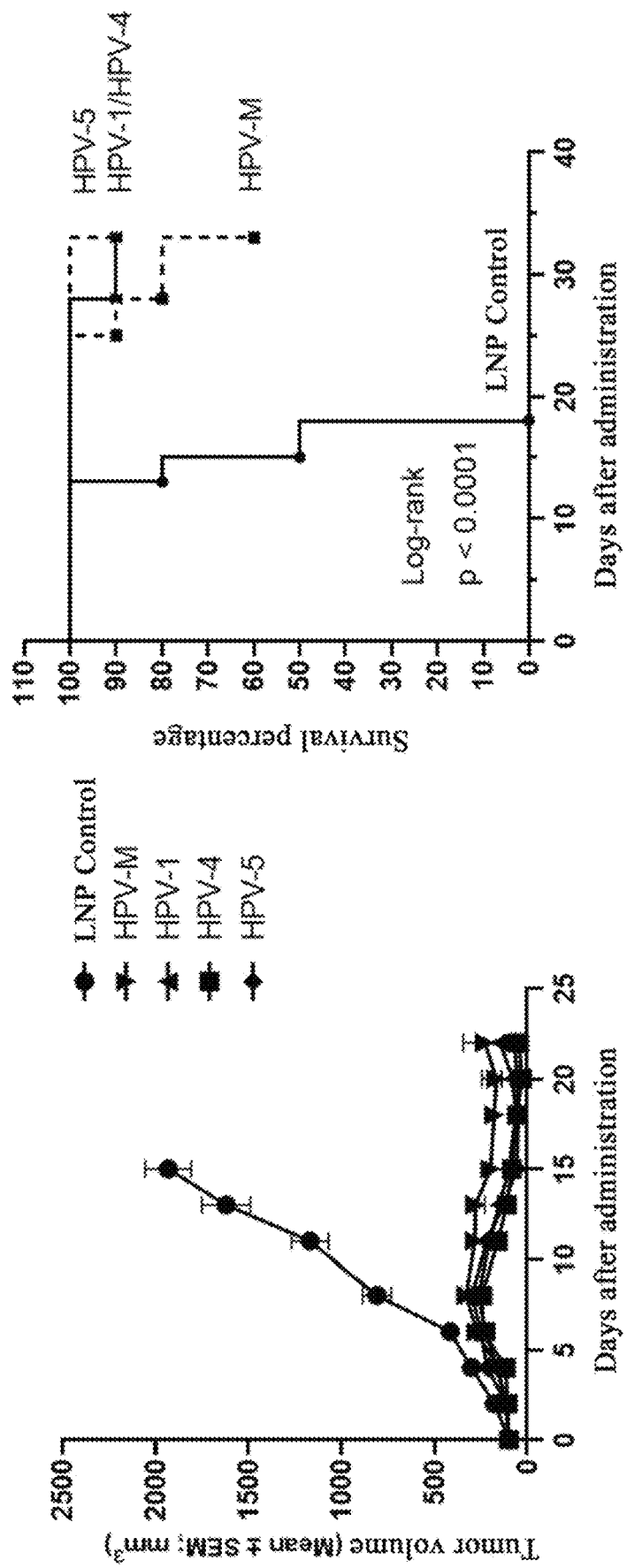
FIG. 8: The anti-tumor effects of three injections of four different mRNA vaccines (12.5 μg) on TC-1 tumor model mice.

The result is shown in FIG. 8, on the TC-1 mouse tumor model, compared with the mice treated with LNP as the control group, the average tumor volume of the mice treated with each vaccine group was significantly reduced, and the survival period of the mice was also significantly prolonged. On day 22 after administration, the proportion of tumor disappearing mice in the HPV-M, HPV-1, HPV-4, and HPV-5 vaccine groups was 30% (3/10), 50% (5/10), 60% (6/10), and 70% (7/10), respectively. Therefore, overall, at the same dose, the anti-tumor effects of HPV-1, HPV-4, and HPV-5 were better than those of the HPV-M vaccines, with HPV-5 being the best.

Figure 9:
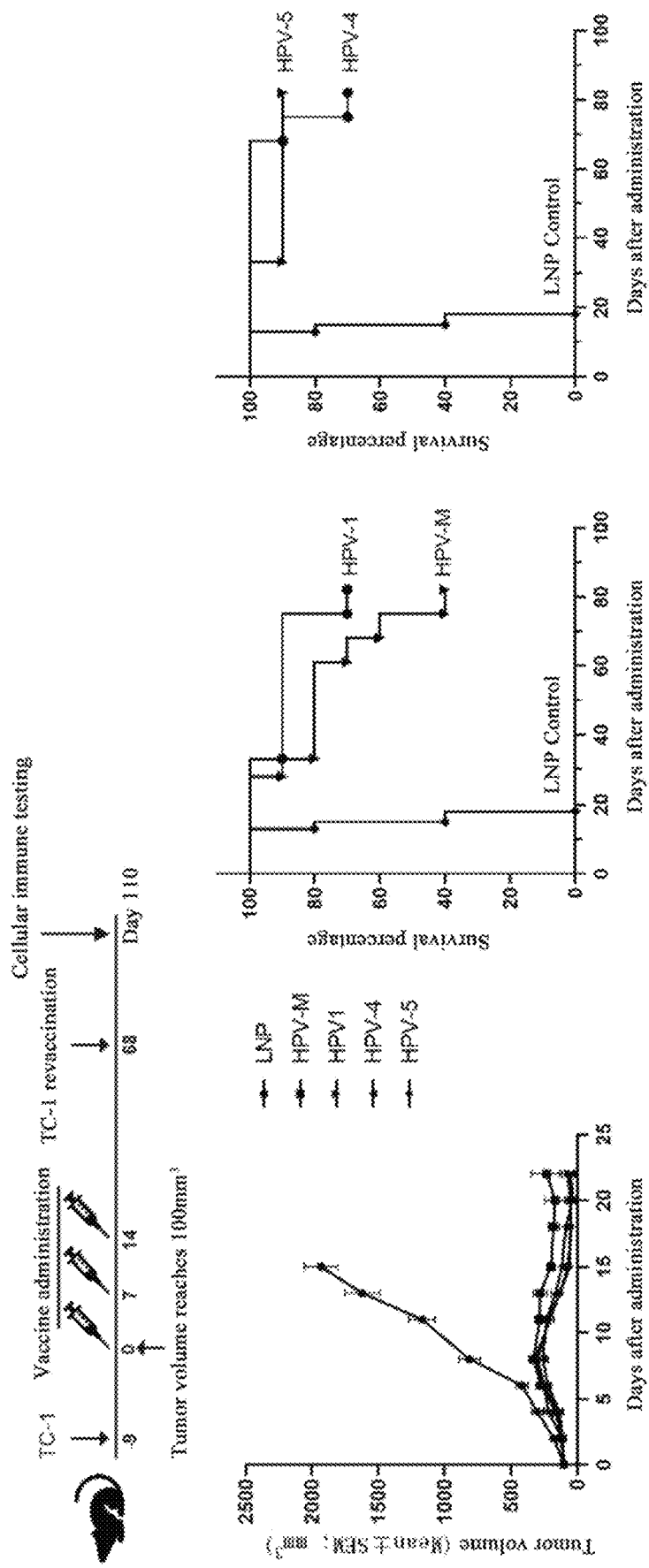
FIG. 9: The anti-tumor effects of three injections of four different mRNA vaccines (12.5 μg) on TC-1 tumor model mice.
Figure 9:
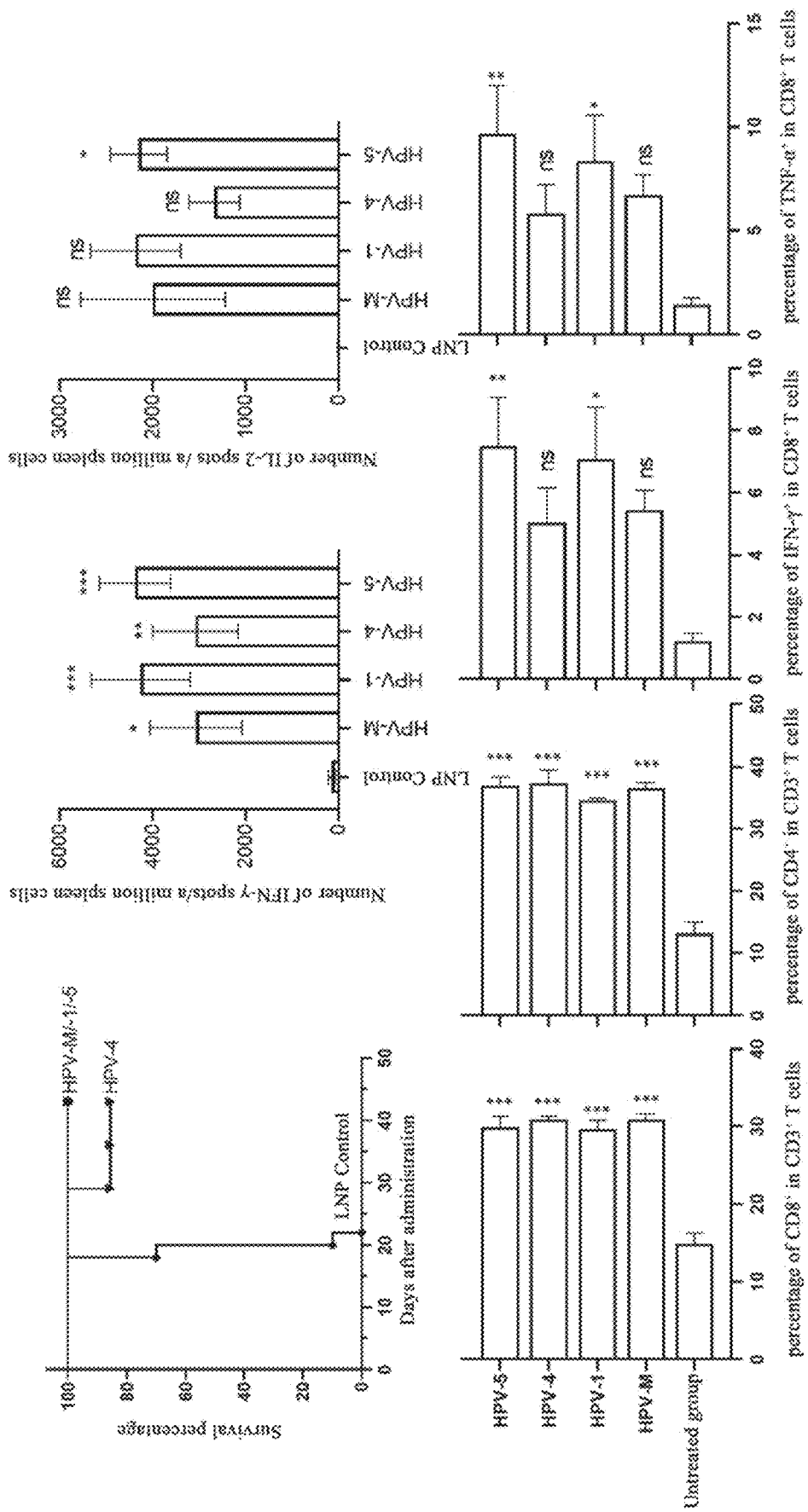

Example 7. Pharmacodynamic Evaluation of Different HPV mRNA Vaccines 6.1 Antitumor Effect of Intramuscular Injection of HPV mRNA Vaccine This study evaluated the pharmacodynamic effects of different HPV mRNA vaccines on TC-1 mouse tumor model using the same method as that in Example 3. According to the grouping shown in Table 9, the mice were immunized with mRNA vaccines once a week for three times (FIG. 9). The tumor size was measured three times a week and the survival status of the mice was recorded.

TABLE 9

Grouping of mice for pharmacodynamic evaluation of HPV-M vaccine

| Vaccine candidates | Dosage | Immunization method | Number of mice |
| --- | --- | --- | --- |
| LNP Ctrl | 12.5 μg | intramuscular injection | 10 |
| HPV-M | 12.5 μg | intramuscular injection | 10 |
| HPV-1 | 12.5 μg | intramuscular injection | 10 |
| HPV-4 | 12.5 μg | intramuscular injection | 10 |
| HPV-5 | 12.5 μg | intramuscular injection | 10 |

As shown in FIG. 9, on the TC-1 mouse tumor model, compared with the mice treated with LNP as the control group, the average tumor volume of the mice treated with each vaccine group was significantly reduced. On day 22 after administration, the proportion of tumor disappearing mice in the HPV-M, HPV-1, HPV-4, and HPV-5 vaccine groups was 40% (4/10), 70% (7/10), 70% (7/10), and 90% (9/10), respectively. The survival time of mice treated with each vaccine group was significantly prolonged, and the results of the HPV-5 treatment group were significantly better than that of the HPV-M treatment group. Therefore, overall, at the same dose, the anti-tumor effects of HPV-1, HPV-4, and HPV-5 are better than those of the HPV-M vaccines, with HPV-5 being the best.

6.2 Research on Long Term Anti-Tumor Effects and Immune Memory of Different HPV mRNA Vaccines Mice with complete regression of tumors above were selected, and on day 68 after initial administration, the mice were reinoculated on the opposite side of the mice' back with equal amount of TC-1 tumor cells, normal untreated mice were inoculated with tumor cells, used as the control group. The growth of tumors and the survival status of the mice were recorded, and the cellular immune levels of the mice at the experimental endpoint were detected using the same ELISpot and flow cytometry methods as in Example 2.

As shown in FIG. 9, compared to the rapid tumor growth in the control group, all mice treated with HPV mRNA vaccines (excluding 14.3% (1/7) of deaths in the HPV-4 group) did not have tumor recurrence and remained completely tumor free for at least 42 days. As shown in FIG. 9, the average spot size of IFN-γ and IL-2 of $SFU/10^6$ spleen cells of mice in the four experimental groups was higher than that of the negative control group, and the CD4+ and CD8+ cells in the spleen cells and the percentage of IFN-γ and TNF-α thereof were higher than those of the negative control group. Among them, both HPV-4 and HPV-5 significantly increased the percentage of IFN-γ and TNF-α in the CD8+ cells. These results all indicated that these four vaccines, especially HPV-5, can induce long-term antigen-specific immune memory, providing strong protection against tumor recurrence. One-way ANOVA statistical analysis of the significance among each group was performed using GraphPad Prism 8 software (* p<0.001 vs. LNP control;  p<0.01 vs. LNP control; * p <0.05 vs. LNP control; ns, no significant difference).

Figure 10:
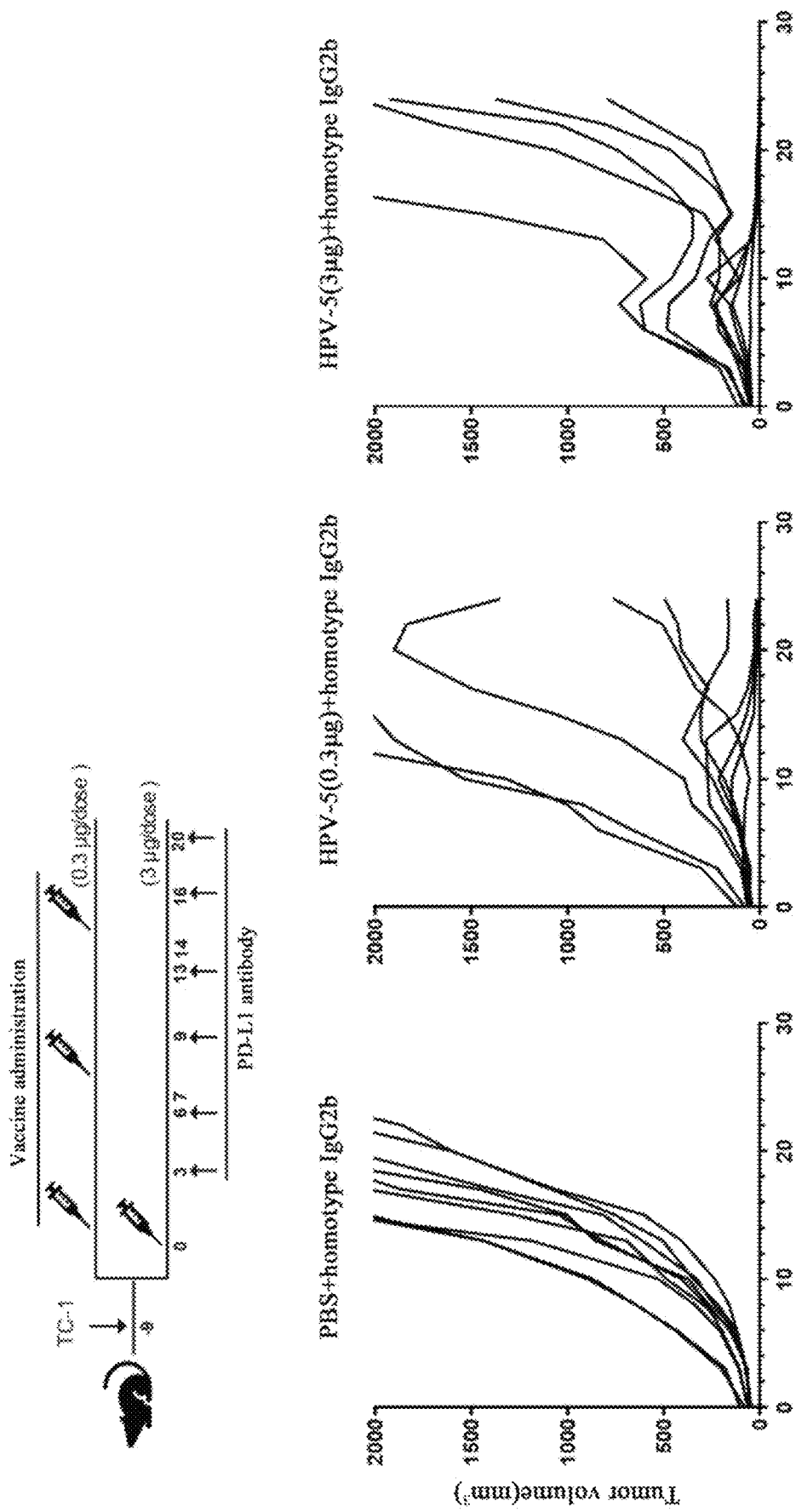
FIG. 10: Evaluation of anti-tumor effect of combination of HPV-5 mRNA vaccine and PD-L1 antibody.
Figure 10:
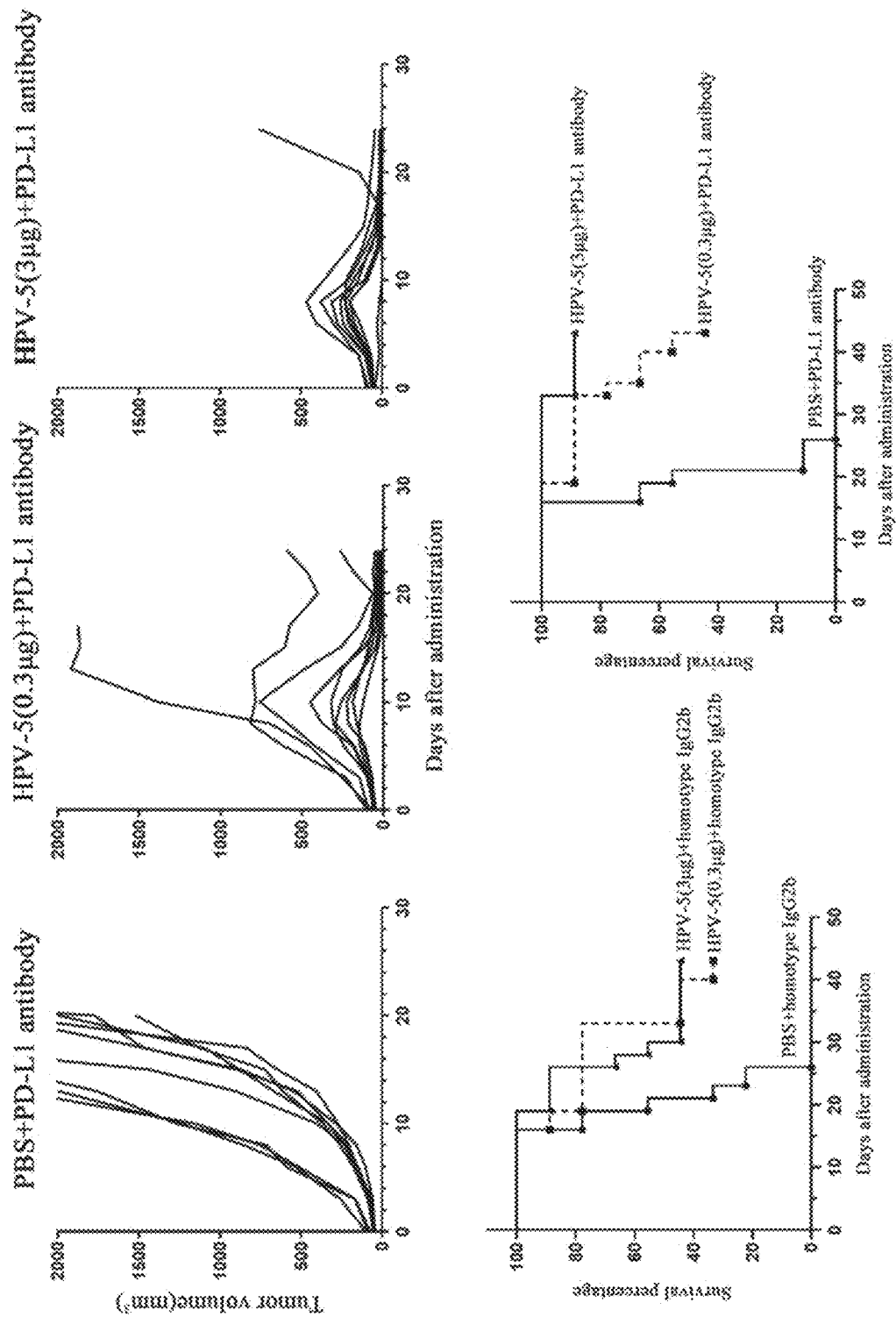

Example 8. Evaluation of the Anti-Tumor Effect of Combination of HPV-5 mRNA Vaccine and PD-L1 Antibody This study evaluated the anti-tumor effect of combination of HPV-5 mRNA vaccine and PD-L1 antibody in TC-1 mouse tumor model using the same method as in Example 3. According to the grouping shown in Table 10, mRNA vaccines and PD-L1 antibodies were administered to mice. Wherein the PD-L1 antibody (10F.9G2) and rabbit homotype IgG2b (LTF-2) were both purchased from BioXcell company, and administered intraperitoneally at dose of 10 mg/kg. The specific medication regimen is shown in FIG. 10. The tumor size was measured three times a week and the survival status of the mice was recorded. Tumor growth and survival curves were drawn based on the measurement results, and the relative tumor proliferation rate (T/C (%)) and the synergistic efficiency of drug combination were calculated by the relative tumor volume (RTV). The specific calculation formula is as follows: $RTV = V_t/V_o$, wherein the $V_t$ and $V_o$ are respectively the tumor volumes measured at a certain time point (dt) and when separating the mice into different cages and starting administration (do). T/C (%)= $(T_{RTV}/C_{RTV}) \times 100\%$, wherein $T_{RTV}$ and $C_{RTV}$ are respectively the RTV values of the experimental group and the control group. The synergistic efficiency (%) of drugs in the groups A and B=$(A_{T/C} \times B_{T/C}/AB_{T/C}) \times 100\%$, wherein $A_{T/C}$, $B_{T/C}$, and $AB_{T/C}$ are respectively the T/C values of A drug group, B drug group, and combination group of AB drug.

TABLE 10

Grouping of mice for pharmacodynamic evaluation of HPV-5 vaccine

| Group | drug | dosage | Immunization method | Number of mice |
|---|---|---|---|---|
| G1 | PBS | — | intramuscular injection | 9 |
|  | homotype IgG2b | 10 mg/kg | intraperitoneal injection |  |
| G2 | HPV-5 | 0.3 μg | intramuscular injection | 9 |
|  | homotype IgG2b | 10 mg/kg | intraperitoneal injection |  |
| G3 | HPV-5 | 3 μg | intramuscular injection | 9 |
|  | homotype IgG2b | 10 mg/kg | intraperitoneal injection |  |
| G4 | PBS | — | intramuscular injection | 9 |
|  | PD-L1 antibody | 10 mg/kg | intraperitoneal injection |  |
| G5 | HPV-5 | 0.3 μg | intramuscular injection | 9 |
|  | PD-L1 antibody | 10 mg/kg | intraperitoneal injection |  |
| G6 | HPV-5 | 3 μg | intramuscular injection | 9 |
|  | PD-L1 antibody | 10 mg/kg | intraperitoneal injection |  |

As shown in FIG. 10, on the TC-1 mouse tumor model, the PBS control group and the PD-L1 antibody monotherapy group showed rapid tumor growth and shorter survival. Compared to PBS, both of the monotherapy group of 3 μg of HPV-5 and the combination group of HPV-5 and PD-L1 antibody significantly inhibited tumor growth and significantly prolonged survival of the mice.

TABLE 11

Analysis of tumor growth data in TC-1 mouse tumor model using combination of HPV-5 and PD-L1 antibody

| Group | Drug | RTV @ day 16 | T/C (%) @ day 16 | synergy efficiency |
|---|---|---|---|---|
| G1 | PBS + homotype IgG2b | 31.24 ± 3.01 | — |  |
| G2 | HPV-5 (0.3 μg) + homotype IgG2b | 11.58 ± 4.22 | 37.07 |  |
| G3 | HPV-5 (3 μg) + homotype IgG2b | 5.65 ± 2.92 | 18.07 |  |
| G4 | PBS + PD-L1 antibody | 33.93 ± 4.45 | 108.61 |  |
| G5 | HPV-5 (0.3 μg) + PD-L1 antibody | 4.32 ± 2.76 | 13.83 | 2.91 |
| G6 | HPV-5 (3 μg) + PD-L1 antibody | 0.31 ± 0.10 | 1.00 | 19.60 |

The tumor data on day 16 after administration were calculated, and the results are shown in Table 11. The synergistic effect of the combination of HPV-5 (0.3 μg) or HPV-5 (3 μg) mRNA vaccine with PD-L1 antibody was 2.91 and 19.60, respectively (when the value >1, the two had a synergistic effect), indicating a good anti-tumor synergistic effect between HPV-5 mRNA vaccine and PD-L1 antibody.

The sequences used in the above Examples of the present application are shown in the following sequence table. It should be understood that the following sequences are only exemplary sequences of the embodiments of the present application, and are not any limitation on the embodiments of the present application. The nucleic acid sequences in the following sequence listing can represent DNA or RNA sequences, and when they represent RNA sequences, the "T" therein represents uridine.

Sequence listing

| SEQ ID NO. | name | sequence |
|---|---|---|
| Amino Acid Sequence ||| 
| 1 | HPV16-E6N | MHQKRTAMFQDPQERPRKLPHLCTELQTTIHDIILECVYCKQQLLRREVYDFAFRDLCIVYRDGNPYAVCDKCLKFYSKISEYRY |

-continued

| SEQ ID NO. | name | sequence |
|---|---|---|
| 2 | HPV16-E7N | MHGDTPTLHEYMLDLQPETTDLYCYEQLNDSSEEEDEIDGPA GQAEPDRAHYNIVTFCCKCDSTL |
| 3 | HPV16-E6C | DKCLKFYSKISEYRYYCYSVYGTTLEQQYNKPLCDLLIRCINC QKPLCPEEKQRHLDKKQRFHNIRGRWTGRCMSCCRSSRTRRE TQL |
| 4 | HPV16-E7C | HYNIVTFCCKCDSTLRLCVQSTHVDIRTLEDLLMGTLGIVCPIC SQKP |
| 5 | HPV18-E6N | MARFEDPTRRPYKLPDLCTELNTSLQDIEITCVYCKTVLELTE VFEFAFKDLFVVYRDSIPHAACHKCIDFYSRIRELRYYSDSV |
| 6 | HPV18-E7N | MYGPKATLQDIVLHLEPQNEIPVDLLCHEQLSDSEEENDEIDG VNHQHLPARRAEPQRHTMLCMC |
| 7 | HPV18-E6C | FYSRIRELRYYSDSVYGDTLEKLINTGLYNLLIRCLRCQKPLNP AEKLRHLNEKRRFHKIAGHYRGQCHSCCNRARQERLQRRRE TQV |
| 8 | HPV18-E7C | ARRAEPQRHTMLCMCCKCEARIELVVESSADDLRAFQQLFLS TLSFVCPWCASQQ |
| 9 | HPV-E2 | MNVCQDKILEHYENDSKDILEHYENDSKDLCDHICDHIDYWK HIRLECAIMYKARIRLECAIMYKAREMGFHQFDGDICNTMHY TNWIYICEDAQCTVVEGQVDKKWEVHAGGQVILCPESGQRRI KRPRSENCHPNKLLILKCLRYRFKKHCKLSSTWHWTCHDGK HKWHWTCHDGKHKNAIVTLTYDHIDYWKAIRQENAIFFAAR HQVVPALNICKAKACKAIEWNTEPKHCFKKGGQHIEVWFDY VAWDSVYYCGDDGWCKTEAEKYGCKGTWEVHFGNSIDCND SMCSTFDDNVSATELVK |
| 10 | Flt3L | ITQDCSFQHSPISSDFAVKIRELSDYLLQDYPVTVASNLQDEEL CGGLWRLVLAQRWMERLKTVAGSKMQGLLERVNTEIHFVTK CAFQPPPSCLRFVQTNISRLLQETSEQLVALKPWITRQNFSRCL ELQCQPDSSTLPPPWSPRPLEATAPTAPGGGSGD |
| 11 | tPA-SP | MDAMKRGLCCVLLLCGAVFVSPS |
| 12 | HPV-M | MHQKRTAMFQDPQERPRKLPHLCTELQTTIHDIILECVYCKQQ LLRREVYDFAFRDLCIVYRDGNPYAVCDKCLKFYSKISEYRY MHGDTPTLHEYMLDLQPETTDLYCYEQLNDSSEEEDEIDGPA GQAEPDRAHYNIVTFCCKCDSTLDKCLKFYSKISEYRYYCYS VYGTTLEQQYNKPLCDLLIRCINCQKPLCPEEKQRHLDKKQR FHNIRGRWTGRCMSCCRSSRTRRETQLHYNIVTFCCKCDSTLR LCVQSTHVDIRTLEDLLMGTLGIVCPICSQKPMARFEDPTRRP YKLPDLCTELNTSLQDIEITCVYCKTVLELTEVFEFAFKDLFVV YRDSIPHAACHKCIDFYSRIRELRYYSDSVMYGPKATLQDIVL HLEPQNEIPVDLLCHEQLSDSEEENDEIDGVNHQHLPARRAEP QRHTMLCMCFYSRIRELRYYSDSVYGDTLEKLINTGLYNLLIR CLRCQKPLNPAEKLRHLNEKRRFHKIAGHYRGQCHSCCNRAR QERLQRRRETQVARRAEPQRHTMLCMCCKCEARIELVVESSA DDLRAFQQLFLSTLSFVCPWCASQQ |
| 13 | HPV-1 and HPV-2 | MARFEDPTRRPYKLPDLCTELNTSLQDIEITCVYCKTVLELTE VFEFAFKDLFVVYRDSIPHAACHKCIDFYSRIRELRYYSDSVM YGPKATLQDIVLHLEPQNEIPVDLLCHEQLSDSEEENDEIDGV NHQHLPARRAEPQRHTMLCMCFYSRIRELRYYSDSVYGDTLE KLTNTGLYNLLIRCLRCQKPLNPAEKLRHLNEKRRFHKIAGHY RGQCHSCCNRARQERLQRRRETQVARRAEPQRHTMLCMCCK CEARIELVVESSADDLRAFQQLFLSTLSFVCPWCASQQMHQK RTAMFQDPQERPRKLPHLCTELQTTIHDIILECVYCKQQLLRR EVYDFAFRDLCIVYRDGNPYAVCDKCLKFYSKISEYRYMHGD TPTLHEYMLDLQPETTDLYCYEQLNDSSEEEDEIDGPAGQAEP DRAHYNIVTFCCKCDSTLDKCLKFYSKISEYRYYCYSVYGTT LEQQYNKPLCDLLIRCINCQKPLCPEEKQRHLDKKQRFHNIRG RWTGRCMSCCRSSRTRRETQLHYNIVTFCCKCDSTLRLCVQS THVDIRTLEDLLMGTLGIVCPICSQKP |
| 14 | HPV-3 | MHQKRTAMFQDPQERPRKLPHLCTELQTTIHDIILECVYCKQQ LLRREVYDFAFRDLCIVYRDGNPYAVCDKCLKFYSKISEYRYA AMHGDTPTLHEYMLDLQPETTDLYCYEQLNDSSEEEDEIDGP AGQAEPDRAHYNIVTFCCKCDSTLAADKCLKFYSKISEYRYY CYSVYGTTLEQQYNKPLCDLLIRCINCQKPLCPEEKQRHLDK |

| SEQ ID NO. | name | sequence |
|---|---|---|
| | | KQRFHNIRGRWTGRCMSCCRSSRTRRETQLAAHYNIVTFCCK CDSTLRLCVQSTHVDIRTLEDLLMGTLGIVCPICSQKPMARFE DPTRRPYKLPDLCTELNTSLQDIEITCVYCKTVLELTEVFEFAF KDLFVVYRDSIPHAACHKCIDFYSRIRELRYYSDSVAAMYGPK ATLQDIVLHLEPQNEIPVDLLCHEQLSDSEEENDEIDGVNHQH LPARRAEPQRHTMLCMCAAFYSRIRELRYYSDSVYGDTLEKL TNTGLYNLLIRCLRCQKPLNPAEKLRHLNEKRRFHKIAGHYR GQCHSCCNRARQERLQRRRETQVAAARRAEPQRHTMLCMCC KCEARIELVVESSADDLRAFQQLFLSTLSFVCPWCASQQ |
| 15 | HPV-4 | MNVCQDKILEHYENDSKDILEHYENDSKDLCDHICDHIDYWK HIRLECAIMYKARIRLECAIMYKAREMGFHQFDGDICNTMHY TNWIYICEDAQCTVVEGQVDKKWEVHAGGQVILCPESGQRRI KRPRSENCHPNKLLILKCLRYRFKKHCKLSSTWHWTCHDGK HKWHWTCHDGKHKNAIVTLTYDHIDYWKAIRQENAIFFAAR HQVVPALNICKAKACKAIEWNTEPKHCFKKGGQHIEVWFDY VAWDSVYYCGDDGWCKTEAEKYGCKGTWEVHFGNSIDCND SMCSTFDDNVSATELVKMHQKRTAMFQDPQERPRKLPHLCTE LQTTIHDIILECVYCKQQLLRREVYDFAFRDLCIVYRDGNPYA VCDKCLKFYSKISEYRYMHGDTPTLHEYMLDLQPETTDLYCY EQLNDSSEEEDEIDGPAGQAEPDRAHYNIVTFCCKCDSTLDKC LKFYSKISEYRYYCYSVYGTTLEQQYNKPLCDLLIRCINCQKP LCPEEKQRHLDKKQRFHNIRGRWTGRCMSCCRSSRTRRETQL HYNIVTFCCKCDSTLRLCVQSTHVDIRTLEDLLMGTLGIVCPIC SQKPMARFEDPTRRPYKLPDLCTELNTSLQDIEITCVYCKTVL ELTEVFEFAFKDLFVVYRDSIPHAACHKCIDFYSRIRELRYYSD SVMYGPKATLQDIVLHLEPQNEIPVDLLCHEQLSDSEEENDEI DGVNHQHLPARRAEPQRHTMLCMCFYSRIRELRYYSDSVYG DTLEKLINTGLYNLLIRCLRCQKPLNPAEKLRHLNEKRRFHKI AGHYRGQCHSCCNRARQERLQRRRETQVARRAEPQRHTMLC MCCKCEARIELVVESSADDLRAFQQLFLSTLSFVCPWCASQQ |
| 16 | HPV-5 | MNVCQDKILEHYENDSKDILEHYENDSKDLCDHICDHIDYWK HIRLECAIMYKARIRLECAIMYKAREMGFHQFDGDICNTMHY TNWIYICEDAQCTVVEGQVDKKWEVHAGGQVILCPESGQRRI KRPRSENCHPNKLLILKCLRYRFKKHCKLSSTWHWTCHDGK HKWHWTCHDGKHKNAIVTLTYDHIDYWKAIRQENAIFFAAR HQVVPALNICKAKACKAIEWNTEPKHCFKKGGQHIEVWFDY VAWDSVYYCGDDGWCKTEAEKYGCKGTWEVHFGNSIDCND SMCSTFDDNVSATELVKMARFEDPTRRPYKLPDLCTELNTSL QDIEITCVYCKTVLELTEVFEFAFKDLFVVYRDSIPHAACHKCI DFYSRIRELRYYSDSVMYGPKATLQDIVLHLEPQNEIPVDLLC HEQLSDSEEENDEIDGVNHQHLPARRAEPQRHTMLCMCFYSR IRELRYYSDSVYGDTLEKLINTGLYNLLIRCLRCQKPLNPAEK LRHLNEKRRFHKIAGHYRGQCHSCCNRARQERLQRRRETQV ARRAEPQRHTMLCMCCKCEARIELVVESSADDLRAFQQLFLS TLSFVCPWCASQQMHQKRTAMFQDPQERPRKLPHLCTELQTT IHDIILECVYCKQQLLRREVYDFAFRDLCIVYRDGNPYAVCDK CLKFYSKISEYRYMHGDTPTLHEYMLDLQPETTDLYCYEQLN DSSEEEDEIDGPAGQAEPDRAHYNIVTFCCKCDSTLDKCLKFY SKISEYRYYCYSVYGTTLEQQYNKPLCDLLIRCINCQKPLCPE EKQRHLDKKQRFHNIRGRWTGRCMSCCRSSRTRRETQLHYNI VTFCCKCDSTLRLCVQSTHVDIRTLEDLLMGTLGIVCPICSQK P |
| 17 | tPA-SP + Flt3L + HPV-M | MDAMKRGLCCVLLLCGAVFVSPSITQDCSFQHSPISSDFAVKI RELSDYLLQDYPVTVASNLQDEELCGGLWRLVLAQRWMERL KTVAGSKMQGLLERVNTEIHFVTKCAFQPPPSCLRFVQTNISR LLQQETSEQLVALKPWITRQNFSRCLELQCQPDSSTLPPPWSPRP LEATAPTAPGGGSGDMHQKRTAMFQDPQERPRKLPHLCTELQ TTIHDIILECVYCKQQLLRREVYDFAFRDLCIVYRDGNPYAVC DKCLKFYSKISEYRYMHGDTPTLHEYMLDLQPETTDLYCYEQ LNDSSEEEDEIDGPAGQAEPDRAHYNIVTFCCKCDSTLDKCLK FYSKISEYRYYCYSVYGTTLEQQYNKPLCDLLIRCINCQKPLC PEEKQRHLDKKQRFHNIRGRWTGRCMSCCRSSRTRRETQLHY NIVTFCCKCDSTLRLCVQSTHVDIRTLEDLLMGTLGIVCPICSQ KPMARFEDPTRRPYKLPDLCTELNTSLQDIEITCVYCKTVLEL TEVFEFAFKDLFVVYRDSIPHAACHKCIDFYSRIRELRYYSDSV MYGPKATLQDIVLHLEPQNEIPVDLLCHEQLSDSEEENDEIDG VNHQHLPARRAEPQRHTMLCMCFYSRIRELRYYSDSVYGDTL EKLTNTGLYNLLIRCLRCQKPLNPAEKLRHLNEKRRFHKIAGH YRGQCHSCCNRARQERLQRRRETQVARRAEPQRHTMLCMCC KCEARIELVVESSADDLRAFQQLFLSTLSFVCPWCASQQ |

Sequence listing

| SEQ ID NO. | name | sequence |
|---|---|---|
| 18 | tPA-SP + Flt3L + HPV-1 and tPA-SP + Flt3L + HPV-2 | MDAMKRGLCCVLLLCGAVFVSPSITQDCSFQHSPISSDFAVKI RELSDYLLQDYPVTVASNLQDEELCGGLWRLVLAQRWMERL KTVAGSKMQGLLERVNTEIHFVTKCAFQPPPSCLRFVQTNISR LLQETSEQLVALKPWITRQNFSRCLELQCQPDSSTLPPPWSPRP LEATAPTAPGGGSGDMARFEDPTRRPYKLPDLCTELNTSLQDI EITCVYCKTVLELTEVFEFAFKDLFVVYRDSIPHAACHKCIDFY SRIRELRYYSDSVMYGPKATLQDIVLHLEPQNEIPVDLLCHEQ LSDSEEENDEIDGVNHQHLPARRAEPQRHTMLCMCFYSRIRE LRYYSDSVYGDTLEKLINTGLYNLLIRCLRCQKPLNPAEKLRH LNEKRRFHKIAGHYRGQCHSCCNRARQERLQRRRETQVARR AEPQRHTMLCMCCKCEARIELVVESSADDLRAFQQLFLSTLSF VCPWCASQQMHQKRTAMFQDPQERPRKLPHLCTELQTTIHDI ILECVYCKQQLLRREVYDFAFRDLCIVYRDGNPYAVCDKCLK FYSKISEYRYMHGDTPTLHEYMLDLQPETTDLYCYEQLNDSS EEEDEIDGPAGQAEPDRAHYNIVTFCCKCDSTLDKCLKFYSKI SEYRYYCYSVYGTTLEQQYNKPLCDLLIRCINCQKPLCPEEKQ RHLDKKQRFHNIRGRWTGRCMSCCRSSRTRRETQLHYNIVTF CCKCDSTLRLCVQSTHVDIRTLEDLLMGTLGIVCPICSQKP |
| 19 | tPA-SP + Flt3L + HPV-3 | MDAMKRGLCCVLLLCGAVFVSPSITQDCSFQHSPISSDFAVKI RELSDYLLQDYPVTVASNLQDEELCGGLWRLVLAQRWMERL KTVAGSKMQGLLERVNTEIHFVTKCAFQPPPSCLRFVQTNISR LLQETSEQLVALKPWITRQNFSRCLELQCQPDSSTLPPPWSPRP LEATAPTAPGGGSGDMHQKRTAMFQDPQERPRKLPHLCTELQ TTIHDIILECVYCKQQLLRREVYDFAFRDLCIVYRDGNPYAVC DKCLKFYSKISEYRYAAMHGDTPTLHEYMLDLQPETTDLYCY EQLNDSSEEEDEIDGPAGQAEPDRAHYNIVTFCCKCDSTLAAD KCLKFYSKISEYRYYCYSVYGTTLEQQYNKPLCDLLIRCINCQ KPLCPEEKQRHLDKKQRFHNIRGRWTGRCMSCCRSSRTRRET QLAAHYNIVTFCCKCDSTLRLCVQSTHVDIRTLEDLLMGTLGI VCPICSQKPMARFEDPTRRPYKLPDLCTELNTSLQDIEITCVYC KTVLELTEVFEFAFKDLFVVYRDSIPHAACHKCIDFYSRIRELR YYSDSVAAMYGPKATLQDIVLHLEPQNEIPVDLLCHEQLSDSE EENDEIDGVNHQHLPARRAEPQRHTMLCMCAAFYSRIRELRY YSDSVYGDTLEKLINTGLYNLLIRCLRCQKPLNPAEKLRHLNE KRRFHKIAGHYRGQCHSCCNRARQERLQRRRETQVAAARRA EPQRHTMLCMCCKCEARIELVVESSADDLRAFQQLFLSTLSFV CPWCASQQ |
| 20 | tPA-SP + Flt3L + HPV-4 | MDAMKRGLCCVLLLCGAVFVSPSITQDCSFQHSPISSDFAVKI RELSDYLLQDYPVTVASNLQDEELCGGLWRLVLAQRWMERL KTVAGSKMQGLLERVNTEIHFVTKCAFQPPPSCLRFVQTNISR LLQETSEQLVALKPWITRQNFSRCLELQCQPDSSTLPPPWSPRP LEATAPTAPGGGSGDMNVCQDKILEHYENDSKDILEHYENDS KDLCDHICDHIDYWKHIRLECAIMYKARIRLECAIMYKAREM GFHQFDGDICNTMHYTNWIYICEDAQCTVVEGQVDKKWEVH AGGQVILCPESGQRRIKRPRSENCHPNKLLILKCLRYRFKKHC KLSSTWHWTCHDGKHKWHWTCHDGKHKNAIVTLTYDHIDY WKAIRQENAIFFAARHQVVPALNICKAKACKAIEWNTEPKHC FKKGGQHIEVWFDYVAWDSVYYCGDDGWCKTEAEKYGCKG TWEVHFGNSIDCNDSMCSTFDDNVSATELVKMHQKRTAMFQ DPQERPRKLPHLCTELQTTIHDIILECVYCKQQLLRREVYDFAF RDLCIVYRDGNPYAVCDKCLKFYSKISEYRYMHGDTPTLHEY MLDLQPETTDLYCYEQLNDSSEEEDEIDGPAGQAEPDRAHYNI VTFCCKCDSTLDKCLKFYSKISEYRYYCYSVYGTTLEQQYNK PLCDLLIRCINCQKPLCPEEKQRHLDKKQRFHNIRGRWTGRC MSCCRSSRTRRETQLHYNIVTFCCKCDSTLRLCVQSTHVDIRT LEDLLMGTLGIVCPICSQKPMARFEDPTRRPYKLPDLCTELNT SLQDIEITCVYCKTVLELTEVFEFAFKDLFVVYRDSIPHAACHK CIDFYSRIRELRYYSDSVMYGPKATLQDIVLHLEPQNEIPVDLL CHEQLSDSEEENDEIDGVNHQHLPARRAEPQRHTMLCMCFYS RIRELRYYSDSVYGDTLEKLINTGLYNLLIRCLRCQKPLNPAE KLRHLNEKRRFHKIAGHYRGQCHSCCNRARQERLQRRRETQ VARRAEPQRHTMLCMCCKCEARIELVVESSADDLRAFQQLFL STLSFVCPWCASQQ |
| 21 | tPA-SP + Flt3L + HPV-5 | MDAMKRGLCCVLLLCGAVFVSPSITQDCSFQHSPISSDFAVKI RELSDYLLQDYPVTVASNLQDEELCGGLWRLVLAQRWMERL KTVAGSKMQGLLERVNTEIHFVTKCAFQPPPSCLRFVQTNISR LLQETSEQLVALKPWITRQNFSRCLELQCQPDSSTLPPPWSPRP LEATAPTAPGGGSGDMNVCQDKILEHYENDSKDILEHYENDS KDLCDHICDHIDYWKHIRLECAIMYKARIRLECAIMYKAREM GFHQFDGDICNTMHYTNWIYICEDAQCTVVEGQVDKKWEVH AGGQVILCPESGQRRIKRPRSENCHPNKLLILKCLRYRFKKHC |

| SEQ ID NO. | name | sequence |
|---|---|---|
| | | KLSSTWHWTCHDGKHKWHWTCHDGKHKNAIVTLTYDHIDY WKAIRQENAIFFAARHQVVPALNICKAKACKAIEWNTEPKHC FKKGGQHIEVWFDYVAWDSVYYCGDDGWCKTEAEKYGCKG TWEVHFGNSIDCNDSMCSTFDDNVSATELVKMARFEDPTRRP YKLPDLCTELNTSLQDIEITCVYCKTVLELTEVFEFAFKDLFVV YRDSIPHAACHKCIDFYSRIRELRYYSDSVMYGPKATLQDIVL HLEPQNEIPVDLLCHEQLSDSEEENDEIDGVNHQHLPARRAEP QRHTMLCMCFYSRIRELRYYSDSVYGDTLEKLINTGLYNLLIR CLRCQKPLNPAEKLRHLNEKRRFHKIAGHYRGQCHSCCNRAR QERLQRRRETQVARRAEPQRHTMLCMCCKCEARIELVVESSA DDLRAFQQLFLSTLSFVCPWCASQQMHQKRTAMFQDPQERP RKLPHLCTELQTTIHDIILECVYCKQQLLRREVYDFAFRDLCIV YRDGNPYAVCDKCLKFYSKISEYRYMHGDTPTLHEYMLDLQP ETTDLYCYEQLNDSSEEEDEIDGPAGQAEPDRAHYNIVTFCCK CDSTLDKCLKFYSKISEYRYYCYSVYGTTLEQQYNKPLCDLLI RCINCQKPLCPEEKQRHLDKKQRFHNIRGRWTGRCMSCCRSS RTRRETQLHYNIVTFCCKCDSTLRLCVQSTHVDIRTLEDLLMG TLGIVCPICSQKP |
| Nucleic acid sequence component 1 | | |
| 22 | 5'UTR | acatttgcttctgacacaactgtgttcactagcaacctcaaacagacacc |
| 23 | 3'UTR | gctcgctttcttgctgtccaatttctattaaaggttcctttgttccctaagtccaactactaaactgg gggatattatgaagggccttgagcatctggattctgcctgctcgcttcttgctgtccaatttctatt aaaggttcctttgttccctaagtccaactactaaactgggggatattatgaagggccttgagcatctg gattctgcct |
| 24 | poly(A) tail | aaaaaaaaaaaaaaaaaaaaaaaaaaaaaaaaaaaaaaaaaaaaaaaaaaaaaG CATATGACTaaaaaaaaaaaaaaaaaaaaaaaaaaaaaaaaaaaaaaaaaaaa aaaaaaaaaa |
| Nucleic acid sequence component 2 | | |
| 25 | 5'UTR | ACTCTTCTGGTCCCCACAGACTCAGAGAGAACCCACC |
| 26 | 3'UTR | GCTGGAGCCTCGGTGGCCATGCTTCTTGCCCCTTGGGCCTC CCCCCAGCCCCTCCTCCCCTTCCTGCACCCGTACCCCCGTG GTCTTTGAATAAAGTCTGAGTGGGCGGC |
| 27 | poly(A) tail | AAAAAAAAAAAAAAAAAAAAAAAAAAAAAAAAAAAA AAAAAAAAAAAAAAAAAAAAGATATCAAAAAAAAAA AAAAAAAGAAAAAAAAAAAAAAAAAGAAAAAAAAA AAAAAAAA |
| ORF sequence | | |
| 28 | Polynucleotide sequence of tPA-SP | ATGGACGCCATGAAGCGCGGTCTTTGCTGCGTCCTGCTGTT ATGCGGCGCTGTGTTCGTCAGCCCTAGC |
| 29 | Polynucleotide sequence of Flt3L | ATAACGCAGGACTGCAGCTTCCAGCACAGCCCTATATCTTC GGACTTCGCGGTCAAGATTCGGGAGCTCTCCGACTATCTGC TCCAGGACTATCCCGTCACGGTCGCCAGCAACCTTCAGGAC GAAGAGTTGTGTGGCGGCCTGTGGCGGTTAGTCCTGGCGC AGCGTTGGATGGAGCGCCTGAAGACCGTGGCTGGTTCGAA GATGCAGGGCTTGCTGGAGCGGGTGAACACGGAGATTCAC TTCGTGACCAAGTGCGCGTTTCAGCCTCCGCCGAGCTGTCT GAGGTTCGTGCAGACGAACATCAGTCGGCTCTTGCAGGAG ACTAGCGAGCAGTTGGTCGCGTTGAAGCCGTGGATCACCC GCCAGAACTTCTCACGTTGCCTTGAGCTGCAGTGCCAGCCG GATTCCTCGACCCTCCCTCCGCCGTGGTCGCCGCGGCCGCT GGAGGCCACGGCGCCCACGGCGCCTGGCGGCGGGAGCGG AGAT |
| 30 | Polynucleotide sequence of HPV16-E6N | ATGCATCAGAAGAGAACCGCCATGTTCCAAGATCCGCAAGA GAGACCTAGAAAACTCCCTCATCTGTGCACCGAACTGCAG ACCACCATCCACGACATCATCCTGGAGTGCGTGTATTGCAA ACAACAGCTGCTGAGAAGAGAGGTGTACGACTTCGCCTTC AGAGACCTGTGCATCGTGTACCGGGACGGCAATCCCTACGC CGTGTGCGACAAGTGCCTCAAGTTCTATAGCAAGATCAGCG AGTATAGATAC |

-continued

| SEQ ID NO. | name | sequence |
|---|---|---|
| 31 | Polynucleotide sequence of HPV16-E7N | ATGCACGGAGATACGCCGACCCTGCACGAGTACATGCTGGA CCTGCAGCCCGAGACCACCGACCTGTACTGCTACGAGCAG CTGAACGACAGCAGCGAAGAGGAGGACGAGATTGACGGC CCGGCCGGCCAAGCCGAGCCCGACAGAGCCCACTACAACA TCGTGACCTTCTGCTGTAAATGCGATAGCACACTG |
| 32 | Polynucleotide sequence of HPV16-E6C | GACAAGTGCCTGAAGTTCTACAGCAAGATTAGCGAGTACA GATATTACTGCTACTCCGTGTACGGGACAACCCTGGAGCAG CAGTACAACAAGCCTCTGTGCGACCTGCTGATCCGGTGTAT TAACTGTCAGAAGCCCTTGTGTCCCGAGGAGAAGCAGAGA CACCTGGACAAGAAGCAGAGATTCCACAACATCAGAGGCA GATGGACCGGCAGATGCATGAGCTGCTGCAGAAGCAGCAG AACAAGAAGAGAGACACAACTG |
| 33 | Polynucleotide sequence of HPV16-E7C | CACTACAATATCGTCACCTTCTGCTGCAAGTGCGACTCCAC ACTGCGGCTCTGCGTGCAGAGCACCCACGTGGACATCAGA ACCCTGGAGGACCTGCTGATGGGCACCCTGGGCATCGTGTG TCCCATCTGCAGCCAAAAGCCCTGATGA |
| 34 | Polynucleotide sequence of HPV18-E6N | ATGGCCCGATTCGAAGATCCCACAAGAAGACCCTACAAGCT GCCCGACCTGTGCACCGAGCTGAACACAAGCCTCCAAGAC ATCGAGATTACCTGCGTGTACTGCAAGACCGTGCTGGAGCT GACCGAGGTGTTCGAGTTCGCCTTCAAGGACCTGTTCGTGG TGTACAGAGACAGCATCCCACACGCCGCCTGCCACAAGTG CATCGACTTCTACAGCCGGATTCGGGAACTGCGGTACTACA GCGACAGCGTG |
| 35 | Polynucleotide sequence of HPV18-E7N | ATGTATGGGCCCAAGGCCACCCTGCAAGACATCGTGCTGCA CCTGGAGCCTCAGAACGAAATACCCGTGGACCTGCTGTGCC ATGAGCAACTGAGCGACAGCGAGGAAGAGAATGATGAGAT CGACGGCGTGAATCATCAGCACCTGCCCGCTAGAAGGGCC GAGCCACAACGGCACACCATGCTGTGCATGTGC |
| 36 | Polynucleotide sequence of HPV18-E6C | TTCTACAGCAGAATCAGAGAACTCCGGTATTACAGCGACTC CGTGTACGGAGATACCCTCGAGAAGCTGACCAACACCGGC CTGTACAATCTGCTGATCAGATGTCTGAGATGTCAGAAACC CTTAAATCCCGCCGAGAAGCTGAGACACCTGAACGAGAAG AGAAGATTCCACAAGATCGCCGGCCACTACAGAGGGCAGT GCCACAGCTGCTGCAACAGAGCTAGACAAGAGAGACTGCA GAGAAGACGGGAGACCCAAGTG |
| 37 | Polynucleotide sequence of HPV18-E7C | GCTAGAAGGGCTGAGCCGCAAAGACATACCATGCTGTGTAT GTGCTGCAAATGCGAGGCTAGAATCGAGCTGGTGGTGGAG AGCAGCGCCGACGACCTGAGAGCCTTTCAGCAGCTGTTCC TGAGCACCCTGAGCTTCGTGTGTCCCTGGTGCGCTAGCCAA CAG |
| 38 | Polynucleotide sequence of HPV-E2 antigen | ATGAACGTGTGCCAGGATAAGATCTTGGAGCATTACGAGAA TGACTCCAAGGATATCCTGGAGCACTATGAGAACGACTCCA AGGATCTATGTGATCACATCTGTGATCACATAGATTATTGGA AGCACATCCGGCTGGAGTGCGCCATTATGTATAAGGCTCGG ATACGGCTGGAATGTGCTATAATGTATAAAGCCCGTGAGATG GGCTTTCACCAGTTCGATGGTGACATTTGTAACACAATGCA CTATACGAACTGGATATACATCTGCGAGGACGCGCAGTGTA CGGTAGTTGAGGGTCAGGTAGACAAGAAGTGGGAGGTTCA CGCGGGTGGGCAGGTCATCCTCTGCCCGGAGTCCGGGCAG AGGAGGATCAAGCGTCCGCGGAGTGAAAACTGCCACCCTA ACAAGCTACTGATCCTCAAGTGCCTTCGCTATCGCTTCAAG AAGCATTGCAAGTTGTCGTCCACGTGGCACTGGACTTGCCA CGACGGCAAGCACAAGTGGCACTGGACGTGCCACGACGGC AAGCACAAGAACGCGATAGTGACGCTTACCTATGATCACAT AGATTATTGGAAAGCGATCCGGCAGGAGAATGCGATATTCT TCGCTGCTAGACACCAGGTGGTGCCCGCGTTGAATATCTGC AAGGCGAAGGCCTGCAAGGCCATAGAGTGGAACACAGAGC CGAAGCACTGCTTTAAGAAAGGCGGTCAGCACATCGAGGT CTGGTTCGACTATGTGGCCTGGGACTCGGTCTACTATTGCGG CGACGACGGTTGGTGCAAGACCGAGGCCGAGAAATACGGC TGCAAAGGGACGTGGGAAGTTCACTTCGGGAACTCCATCG ATTGCAACGACTCCATGTGCAGCACGTTTGACGATAACGTG TCTGCCACGGAGTTGGTAAAG |

| SEQ ID NO. | name | sequence |
|---|---|---|
| 39 | Polynucleotide sequence of HPV-M | ATGCACCAGAAGAGAACCGCCATGTTCCAGGACCCTCAGG<br>AGAGACCTAGGAAGCTGCCTCACCTGTGTACAGAGCTCCA<br>GACAACCATCCACGACATCATCCTGGAGTGCGTGTACTGTA<br>AGCAGCAGCTGCTGAGAAGAGAGGTGTACGACTTCGCCTT<br>CAGAGACCTGTGCATCGTGTACAGAGACGGCAACCCTTAC<br>GCCGTGTGCGATAAGTGTCTGAAGTTCTATTCCAAAATCTCC<br>GAATATAGGTACATGCACGGCGACACCCCTACCCTGCACGA<br>GTACATGCTGGACCTCCAGCCTGAGACCACAGACCTGTACT<br>GCTACGAGCAGCTGAACGACAGCTCTGAGGAAGAGGACGA<br>GATTGACGGACCTGCTGGCCAGGCCGAGCCTGACAGAGCC<br>CACTACAATATCGTGACATTCTGTTGCAAATGCGACTCCACA<br>CTGGACAAGTGCCTGAAGTTCTACAGCAAGATCTCTGAGTA<br>CAGATACTACTGCTACTCTGTGTACGGCACCACACTGGAGC<br>AGCAGTACAACAAGCCTCTGTGCGACCTCCTGATCCGCTGC<br>ATCAACTGCCAGAAGCCTCTGTGCCCTGAGGAGAAGCAGA<br>GACACCTGGACAAGAAGCAGCGGTTCCACAACATCAGAGG<br>CAGATGGACCGGCAGGTGCATGTCCTGCTGTAGATCCTCCA<br>GAACCAGACGGGAGACCCAGCTGCACTACAACATCGTGAC<br>CTTCTGCTGCAAGTGCGACTCTACCCTGAGACTGTGCGTGC<br>AGTCTACCCACGTGGACATCAGAACCCTGGAGGACCTGCT<br>GATGGGCACCCTGGGCATCGTGTGCCCTATCTGCTCTCAGA<br>AGCCTATGGCCAGGTTCGAGGACCCTACCAGAAGACCCTAC<br>AAGCTGCCTGACCTGTGCACCGAGCTGAACACCTCTCTGCA<br>AGACATCGAGATCACCTGCGTGTACTGCAAGACCGTGCTGG<br>AGCTGACCGAGGTGTTCGAGTTCGCCTTCAAGGACCTGTTC<br>GTGGTGTACAGAGACAGCATCCCTCACGCTGCCTGCCACAA<br>GTGCATCGACTTCTATTCCAGGATCAGGGAGCTGCGCTATTA<br>CTCCGACTCTGTGATGTACGGCCCCAAGGCCACCCTCCAGG<br>ACATCGTGCTGCACCTGGAGCCTCAGAACGAGATCCCCGTG<br>GACCTGCTGTGCCACGAGCAGCTGTCTGACTCTGAAGAGG<br>AGAACGACGAGATCGACGGCGTGAACCACCAGCACCTGCC<br>TGCCAGGAGAGCTGAACCCCAGCGGCATACCATGCTGTGTA<br>TGTGCTTCTACTCTAGGATCAGAGAGCTGAGGTACTACTCT<br>GACTCTGTGTACGGCGACACCCTGGAGAAGCTGACCAACA<br>CCGGCCTGTACAACCTGCTGATCCGGTGCCTGAGGTGCCAG<br>AAGCCTCTGAACCCTGCCGAGAAGCTGAGACACCTGAACG<br>AGAAGAGAAGATTCCACAAGATCGCTGGCCACTACAGAGG<br>CCAGTGCCACTCTTGCTGCAACAGAGCCAGACAGGAGAGA<br>CTCCAGCGGAGAAGGGAGACCCAGGTGGCCAGGAGAGCC<br>GAGCCTCAGAGACACACCATGCTGTGCATGTGCTGCAAGTG<br>CGAGGCCAGAATCGAGCTGGTGGTGGAGAGCTCTGCCGAC<br>GACCTGAGAGCCTTCCAGCAGCTGTTCCTGTCTACCCTGAG<br>CTTCGTGTGCCCTTGGTGCGCCTCTCAGCAGTAA |
| 40 | Polynucleotide sequence-1 of HPV-1 | ATGGCTAGATTCGAGGACCCCACAAGAAGACCCTACAAGC<br>TGCCCGACCTGTGCACCGAACTGAACACAAGCCTGCAAGA<br>CATCGAGATTACCTGCGTGTATTGCAAGACCGTGCTGGAGC<br>TGACCGAGGTGTTCGAGTTCGCCTTCAAGGACCTGTTCGTG<br>GTGTACAGAGATAGCATCCCCCACGCCGCCTGCCACAAGTG<br>CATCGACTTCTATAGCAGAATCAGAGAACTGCGGTACTACA<br>GCGATAGCGTGATGTACGGCCCCAAGGCCACCCTCCAAGAC<br>ATCGTCCTGCACCTGGAGCCTCAGAATGAGATCCCCGTGGA<br>CCTGCTGTGCCACGAGCAGCTGAGCGACAGCGAGGAAGAA<br>AACGACGAGATCGACGGCGTCAATCATCAGCACCTGCCCGC<br>TAGACGGGCTGAGCCTCAGCGGCACACCATGCTGTGTATGT<br>GCTTCTACAGCAGAATTAGAGAGCTCAGATACTACAGCGAC<br>AGCGTGTATGGCGACACCCTGGAGAAGCTGACCAACACCG<br>GCCTGTACAATCTGCTGATCAGATGCCTGAGATGTCAGAAG<br>CCCCTCAACCCCGCCGAGAAGCTGAGACACCTGAACGAGA<br>AGAGAAGATTCCACAAGATCGCCGGCCACTACAGAGGGCA<br>GTGCCACAGCTGCTGCAACAGAGCTAGACAAGAGAGACTG<br>CAGAGACGGCGGGAAACCCAAGTGGCTAGAAGGGCCGAG<br>CCTCAGAGACATACAATGCTGTGCATGTGCTGCAAGTGCGA<br>AGCTAGAATCGAGCTGGTGGTGGAGAGCAGCGCCGACGAC<br>CTGAGAGCCTTTCAGCAGCTGTTCCTGAGCACCCTGAGCTT<br>CGTGTGCCCCTGGTGCGCTAGCCAACAGATGCATCAGAAGA<br>GAACCGCCATGTTCCAAGACCCCCAAGAGAGACCTAGAAA<br>GCTGCCCCACCTGTGTACCGAGCTGCAGACAACCATCCACG<br>ACATCATCCTGGAGTGCGTGTACTGCAAGCAGCAACTGCTG<br>AGAAGAGAGGTGTACGACTTCGCCTTCAGAGACCTGTGCA<br>TCGTGTACCGGGACGGGAATCCCTACGCCGTGTGCGACAAA<br>TGTCTCAAGTTTTATAGCAAGATTAGCGAGTACAGATACATG<br>CACGGCGACACCCCCACCCTGCACGAGTACATGCTGGACCT |

| SEQ ID NO. | name | sequence |
|---|---|---|
| | | GCAGCCCGAGACCACCGACCTGTACTGCTACGAACAACTG<br>AACGACAGCTCCGAGGAAGAGGACGAAATCGACGGCCCCG<br>CCGGCCAAGCCGAGCCCGACAGAGCCCACTACAACATTGT<br>GACATTCTGTTGCAAGTGTGACAGCACCCTGGACAAATGCC<br>TGAAGTTCTACAGCAAGATCAGCGAGTACAGATATTACTGC<br>TACAGCGTGTACGGCACCACCCTGGAGCAGCAGTACAACA<br>AGCCCCTGTGTGACCTGCTGATTAGATGCATCAACTGTCAG<br>AAGCCCCTGTGCCCCGAGGAGAAGCAGAGACACCTGGACA<br>AGAAGCAGAGATTCCACAACATCAGAGGCAGATGGACCGG<br>CAGATGCATGAGCTGCTGCAGAAGCAGCAGAACAAGAAGA<br>GAGACACAGCTGCACTACAATATCGTGACCTTTTGCTGCAA<br>GTGCGATAGCACCCTGCGGCTGTGCGTGCAGAGCACCCAC<br>GTGGACATCAGAACCCTGGAGGACCTGCTGATGGGCACCC<br>TGGGCATCGTGTGCCCCATCTGCAGCCAAAAGCCCTGATGA |
| 41 | Polynucleotide sequence-2 of HPV-1 | ATGGCGCGGTTCGAGGACCCGACTCGCAGGCCGTATAAGTT<br>ACCGGATCTCTGTACAGAGCTGAACAGTCCTTGCAGGACA<br>TCGAAATCACCTGCGTGTACTGCAAGACCGTCTTGGAGTTA<br>ACGGAGGTGTTCGAGTTCGCCTTCAAGGACTTGTTCGTTGT<br>GTACAGAGATTCGATACCTCATGCGGCCTGCCACAAGTGCA<br>TCGATTTCTATTCGCGCATTCGAGAGCTGAGGTACTACTCGG<br>ACAGTGTCATGTACGGGCCTAAGGCCACGTTACAGGACATT<br>GTCCTCCACCTGGAACCTCAGAATGAGATTCCGGTGGACCT<br>GCTCTGCCATGAGCAGCTCTCGGACTCCGAGGAAGAGAAC<br>GATGAGATCGACGGAGTGAACCATCAGCACCTGCCCGCGA<br>GAAGGGCAGAGCCACAGCGTCACACAATGCTGTGTATGTG<br>CTTCTACTCGCGGATCAGGGAGCTGAGGTATTACTCCGACT<br>CGGTCTACGGAGACACCTTAGAGAAGTTGACAAACACCGG<br>TTTGTACAACCTTCTCATAAGGTGTCTCCGTTGCCAAAAGC<br>CTCTGAATCCGGCGGAGAAGCTGCGGCATCTCAACGAGAA<br>GCGGCGGTTTCACAAGATCGCCGGGCACTACAGAGGACAG<br>TGCCACAGCTGCTGCAACCGCGCCAGACAGGAGCGGTTGC<br>AGCGGCGGCGCGAGACCCAGGTTGCCCGGCGAGCCGAGCC<br>GCAGCGACATACAATGCTTTGTATGTGCTGCAAGTGCGAGG<br>CTCGGATAGAGCTTGTCGTGGAATCTTCTGCGGATGACCTG<br>CGAGCATTCCAGCAGCTGTTTCTGAGCACTCTGTCGTTCGT<br>GTGCCCGTGGTGCGCGAGCCAGCAGATGCATCAGAAGCGG<br>ACTGCTATGTTCCAAGACCCGCAGGAGAGGCCACGCAAGC<br>TTCCACATCTGTGTACAGAGCTCCAAACCACCATCCACGAC<br>ATCATCCTGGAGTGCGTGTACTGCAAACAGCAGCTGCTGAG<br>AAGAGAGGTGTACGACTTCGCCTTCAGAGACCTGTGCATCG<br>TGTACAGAGATGGGAATCCCTACGCCGTGTGCGACAAGTGC<br>CTGAAGTTCTATAGCAAGATCAGCGAGTACAGATACATGCA<br>TGGCGACACACCCACCCTGCACGAGTACATGCTGGACCTGC<br>AGCCCGAGACCACCGACCTGTACTGCTATGAGCAGCTGAA<br>CGACAGCAGCGAAGAGGAGGACGAGATCGACGGCCCTGCT<br>GGCCAAGCCGAGCCCGACAGAGCCCACTATAACATCGTCA<br>CATTCTGTTGCAAATGTGACTCCACCCTGGACAAGTGTCTG<br>AAATTCTATAGCAAGATCTCCGAGTACCGGTACTACTGTTAC<br>AGCGTGTACGGCACCACACTGGAGCAGCAGTACAACAAGC<br>CGCTTTGCGATCTGCTGATCCGGTGCATCAACTGTCAGAAG<br>CCCTTGTGTCCGAAGAGAAGCAGAGACACCTGGACAAGA<br>AGCAGAGATTCCACAACATCAGAGGCAGATGGACCGGCAG<br>ATGCATGAGCTGCTGCAGAAGCAGCAGAACCGGAGAGAG<br>ACCCAACTCCACTACAATATCGTGACCTTCTGTTGCAAGTG<br>CGATAGCACCCTGAGACTGTGCGTGCAGAGCACCCACGTG<br>GACATCAGAACCCTGGAGGACCTGCTGATGGGCACCCTGG<br>GCATCGTGTGCCCTATCTGCAGCCAAAAGCCCTGATGA |
| 42 | Polynucleotide sequence of HPV-2 | ATGGCTAGATTCGAGGACCCCACAAGAAGACCCTACAAGC<br>TGCCCGATCTCTGCACAGAGCTGAACACAAGCCTGCAAGA<br>CATCGAGATCACCTGCGTGTATTGCAAGACCGTGCTGGAGC<br>TGACCGAGGTGTTCGAGTTCGCCTTCAAGGACCTGTTCGTG<br>GTGTACAGAGACAGCATCCCCCACGCCGCCTGCCACAAGT<br>GCATCGACTTCTACAGCCGGATCAGAGAGCTCCGGTACTAC<br>AGCGACTCCGTGATGTACGGCCCCAAGGCCACCCTCCAAG<br>ACATCGTGCTGCACCTGGAGCCTCAGAACGAGATCCCCGTG<br>GACCTGCTGTGCCACGAGCAGCTGAGCGACAGCGAGGAAG<br>AGAACGACGAAATTGACGCGTGAACCATCAGCACCTGCC<br>CGCTAGACGGGCCGAGCCTCAGCGGCACACCATGCTGTGTA<br>TGTGCTTCTACAGCAGAATCAGAGAACTCAGATATTACTCC<br>GACTCCGTGTACGGCGACACACTGGAGAAGCTGACCAACA<br>CCGGCCTGTACAACCTGCTGATCAGATGCCTGAGATGTCAG<br>AAGCCTCTCAATCCCGCCGAGAAGCTGAGACACCTGAACG |

Sequence listing

| SEQ ID NO. | name | sequence |
|---|---|---|
| | | AGAAGAGAAGATTCCACAAGATCGCCGGCCACTACAGAGG GCAGTGCCACAGCTGCTGCAACAGAGCTAGACAAGAGAGA CTGCAGAGAAGACGGGAGACCCAAGTGGCTAGAAGGGCC GAGCCTCAGAGACACACCATGCTGTGCATGTGCTGCAAGTG CGAAGCTAGAATCGAGCTGGTGGTGGAGAGCAGCGCCGAC GACCTGAGAGCCTTTCAGCAGCTGTTCCTGAGCACCCTGAG CTTCGTGTGCCCCTGGTGCGCTAGCCAACAGATGCATCAGA AGAGAACCGCCATGTTCCAAGACCCCCAAGAGAGACCTAG AAAGCTGCCCCACCTGTGTACAGAGCTCCAAACCACCATCC ACGACATCATCCTGGAGTGCGTGTACTGCAAACAGCAGCTG CTGAGAAGAGAGGTGTACGACTTCGCCTTCAGAGACCTGT GCATCGTGTACAGAGATGGGAATCCCTACGCCGTGTGCGAC AAGTGCCTGAAGTTTTATAGCAAGATCAGCGAGTACAGATA CATGCATGGCGACACCCCCACCCTGCACGAGTACATGCTGG ACCTGCAGCCCGAGACCACCGACCTGTACTGCTATGAGCAG CTGAACGACAGCAGCGAAGAGGAGGACGAGATCGACGGC CCCGCTGGCCAAGCCGAGCCCGACAGAGCCCACTATAACAT CGTCACATTCTGTTGCAAATGTGACTCCACCCTGGACAAGT GTCTGAAATTCTATAGCAAGATCTCCGAGTACCGGTACTACT GTTACAGCGTGTACGGCACCACACTGGAGCAGCAGTACAA CAAGCCCCTGTGCGATCTGCTGATCCGGTGCATCAACTGTC AGAAGCCCCTGTGTCCCGAAGAGAAGCAGAGACACCTGGA CAAGAAGCAGAGATTCCACAACATCAGAGGCAGATGGACC GGCAGATGCATGAGCTGCTGCAGAAGCAGCAGAACCCGGA GAGAGACCCAACTCCACTACAATATCGTGACCTTCTGTTGC AAGTGCGATAGCACCCTGAGACTGTGCGTGCAGAGCACCC ACGTGGACATCAGAACCCTGGAGGACCTGCTGATGGGCAC CCTGGGCATCGTGTGCCCCATCTGCAGCCAAAAGCCCTGAT GA |
| 43 | Polynucleotide sequence of HPV-3 | ATGCATCAGAAGAGAACCGCCATGTTCCAAGACCCCCAAG AGAGACCTAGAAAGCTGCCCCACCTGTGCACCGAGCTGCA GACCACCATCCACGACATCATCCTGGAGTGCGTGTACTGTA AGCAGCAGCTGCTGAGAAGAGAGGTGTACGACTTCGCCTT CAGAGACCTGTGCATCGTGTATAGAGACGGCAACCCCTACG CCGTGTGCGATAAGTGCCTGAATTCTACTCCAAGATCAGC GAGTACAGATACGCCGCCATGCACGGCGACACCCCCACCCT GCACGAGTACATGCTGGACCTGCAGCCCGAGACCACCGAC CTGTACTGCTACGAGCAGCTGAACGACAGCTCCGAAGAGG AGGACGAGATCGACGGCCCCGCCGGCCAAGCCGAGCCCGA CAGAGCTCACTACAATATCGTGACATTCTGCTGCAAGTGCG ACTCCACACTGGCTGCCGACAAGTGCCTCAAGTTTTACAGC AAGATCTCCGAATACAGATACTACTGCTACAGCGTGTACGG GACCACCCTGGAGCAGCAGTACAACAAACCTCTCTGCGAC CTGCTGATTAGATGCATTAATTGTCAGAAGCCCCTGTGCCCC GAGGAGAAGCAGAGACACCTGGACAAGAAGCAGAGATTC CACAACATCAGAGGCAGATGGACCGGCAGATGCATGAGCT GCTGCAGAAGCAGCAGAACAAGAAGAGAGACACAGCTGG CCGCTCACTACAACATCGTCACCTTCTGTTGTAAGTGCGAC TCCACCCTGAGACTGTGCGTGCAGAGCACCCACGTGGACA TCAGAACCCTGGAGGACCTGCTGATGGGCACCCTGGGCATC GTGTGCCCCATCTGCAGCCAAAAGCCCATGGCTAGATTCGA GGACCCCACAAGAAGACCCTACAAGCTGCCCGACCTGTGT ACAGAACTGAACACAAGCCTGCAAGACATCGAGATCACCT GCGTGTACTGCAAGACCGTGCTGGAGCTGACCGAGGTGTT CGAGTTCGCCTTCAAGGACCTGTTCGTGGTGTACAGAGACA GCATCCCCCACGCCGCCTGCCACAAGTGCATCGACTTCTAC AGCAGAATTAGAGAACTGCGGTACTACAGCGACAGCGTGG CCGCCATGTACGGCCCCAAGGCCACCCTCCAAGACATCGTG CTGCACCTCGAGCCTCAGAACGAGATCCCCGTGGACCTGCT GTGCCACGAACAGCTGAGCGACAGCGAGGAAGAGAACGA CGAGATTGACGGCGTGAACCATCAGCACCTGCCCGCTCGG AGAGCTGAGCCCCAACGGCACACCATGCTGTGTATGTGTGC CGCTTTCTATAGCAGAATCCGGGAGCTGCGGTACTATTCCGA CAGCGTGTACGGGACACACTGGAAGCTGACCAACACC GGCCTGTACAATCTGCTGATCAGATGCCTCAGATGTCAGAA ACCCCTCAACCCTGCCGAGAAGCTGAGACACCTGAACGAG AAGAGAAGATTCCACAAGATCGCCGGCCACTACAGAGGGC AGTGCCACAGCTGCTGCAACAGAGCTAGACAAGAGAGACT GCAGAGACGGAGAGAGACCCAAGTGGCCGCTGCTAGAAG GGCCGAGCCTCAGAGACACACAATGCTGTGCATGTGCTGC |

| SEQ ID NO. | name | sequence |
|---|---|---|
| | | AAATGCGAGGCTAGAATCGAGCTGGTGGTGGAGAGCAGCG CCGACGACCTGAGAGCCTTTCAGCAGCTGTTCCTGAGCACC CTGAGCTTCGTGTGCCCCTGGTGCGCTAGCCAACAGTGATG A |
| 44 | Polynucleotide sequence-1 of HPV-4 | ATGAACGTGTGCCAAGACAAGATCCTGGAACACTACGAGA ATGACAGCAAAGACATTCTGGAGCACTACGAAAATGATTCC AAGGACCTGTGTGACCATATCTGTGATCATATCGATTATTGG AAGCACATCAGACTGGAATGTGCTATCATGTACAAGGCCCG GATCAGACTGGAGTGCGCCATCATGTACAAGGCTCGGGAAA TGGGCTTCCATCAGTTCGACGGCGACATCTGCAACACCATG CACTACACCAACTGGATCTACATCTGCGAGGACGCTCAGTG CACCGTGGTGGAGGGCCAAGTGGACAAGAAGTGGGAGGT GCACGCCGGCGGCCAAGTGATCCTGTGCCCTGAAAGCGGG CAGAGAAGAATCAAGAGACCCCGGAGCGAGAACTGCCACC CCAACAAGCTGCTGATCCTGAAGTGCCTGAGATACAGATTC AAGAAGCACTGCAAGCTGAGCAGCACCTGGCACTGGACCT GCCATGATGGCAAACACAAGTGGCACTGGACCTGCCACGA CGGCAAGCATAAGAATGCCATCGTGACCCTGACCTACGACC ACATCGATTATTGGAAGGCCATCAGACAAGAGAACGCCATC TTCTTCGCCGCTAGACACCAAGTGGTGCCCGCCCTGAACAT CTGCAAGGCCAAGGCCTGCAAGGCCATCGAGTGGAACACC GAGCCCAAGCACTGCTTCAAGAAGGGCGGGCAGCACATCG AGGTGTGGTTCGACTACGTCGCCTGGGATAGCGTGTACTAC TGCGGCGACGACGCTGGTGCAAGACCGAGGCCGAGAAGT ACGGCTGCAAGGGCACCTGGGAGGTCCACTTCGGCAACAG CATCGACTGCAACGACAGCATGTGCAGCACCTTCGACGAC AACGTGAGCGCCACCGAGCTGGTGAAGATGCATCAGAAGA GAACCGCCATGTTCCAAGACCCCCAAGAGAGACCTAGAAA ACTCCCCCATCTGTGCACCGAACTGCAGACCACCATCCACG ACATCATCCTGGAGTGCGTGTATTGCAAACAACAGCTGCTG AGAAGAGAGGTGTACGACTTCGCCTTCAGAGACCTGTGCA TCGTGTACCGGGACGGCAATCCCTACGCCGTGTGCGACAAG TGCCTCAAGTTTTATAGCAAGATCAGCGAGTATAGATACATG CACGGGGACACCCCCACCCTGCACGAGTACATGCTGGACC TGCAGCCCGAGACCACCGACCTGTACTGCTACGAGCAGCT GAACGACAGCAGCGAAGAGGAGGACGAGATTGACGGCCC CGCCGGCCAAGCCGAGCCCGACAGAGCCCACTACAACATC GTGACCTTCTGCTGTAAATGCGATAGCACACTGGACAAGTG CCTGAAGTTCTACAGCAAGATTAGCGAGTACAGATATTACT GCTACTCCGTGTACGGGACAACCCTGGAGCAGCAGTACAA CAAGCCTCTGTGCGACCTGCTGATCCGGTGTATTAACTGTC AGAAGCCCCTGTGCCCCGAGGAGAAGCAGAGACACCTGGA CAAGAAGCAGAGATTCCACAACATCAGAGGCAGATGGACC GGCAGATGCATGAGCTGCTGCAGAAGCAGCAGAACAAGAA GAGAGACACAACTGCACTACAATATCGTCACCTTCTGCTGC AAGTGCGACTCCACACTGCGGCTCTGCGTGCAGAGCACCC ACGTGGACATCAGAACCCTGGAGGACCTGCTGATGGGCAC CCTGGGCATCGTGTGCCCCATCTGCAGCCAAAAGCCCATGG CTAGATTCGAGGACCCCACAAGAAGACCCTACAAGCTGCC CGACCTGTGCACCGAGCTGAACACAAGCCTCCAAGACATC GAGATTACCTGCGTGTACTGCAAGACCGTGCTGGAGCTGAC CGAGGTGTTCGAGTTCGCCTTCAAGGACCTGTTCGTGGTGT ACAGAGACAGCATCCCCACGCCGCCTGCCACAAGTGCAT CGACTTCTACAGCCGGATTCGGGAACTGCGGTACTACAGCG ACAGCGTGATGTATGGCCCCAAGGCCACCCTGCAAGACATC GTGCTGCACCTGGAGCCTCAGAACGAAATCCCGTGGACC TGCTGTGCCATGAGCAACTGAGCGACAGCGAGGAAGAGAA TGATGAGATCGACGGCGTGAATCATCAGCACCTGCCCGCTA GAAGGGCCGAGCCCAACGGCACACCATGCTGTGCATGTG CTTCTACAGCAGAATCAGAGAACTCCGGTATTACAGCGACT CCGTGTACGGGGATACCCTCGAGAAGCTGACCAACACCGG CCTGTACAATCTGCTGATCAGATGTCTGAGATGTCAGAAAC CCCTGAACCCCGCCGAGAAGCTGAGACACCTGAACGAGAA GAGAAGATTCCACAAGATCGCCGGCCACTACAGAGGGCAG TGCCACAGCTGCTGCAACAGAGCTAGACAAGAGAGACTGC AGAGAAGACGGGAGACCCAAGTGGCTAGAAGGGCTGAGC CCAAAGACATACCATGCTGTGTATGTGCTGCAAATGCGAG GCTAGAATCGAGCTGGTGGTGGAGAGCAGCGCCGACGACC TGAGAGCCTTTCAGCAGCTGTTCCTGAGCACCCTGAGCTTC GTGTGCCCCTGGTGCGCTAGCCAACAGTGATGA |

-continued

Sequence listing

| SEQ ID NO. | name | sequence |
|---|---|---|
| 45 | Polynucleotide sequence-2 of HPV-4 | ATGAACGTGTGCCAGGATAAGATCTTGGAGCATTACGAGAA<br>TGACTCCAAGGATATCCTGGAGCACTATGAGAACGACTCCA<br>AGGATCTATGTGATCACATCTGTGATCACATAGATTATTGGA<br>AGCACATCCGGCTGGAGTGCGCCATTATGTATAAGGCGCGT<br>ATCCGGCTGGAATGTGCTATAATGTATAAAGCCCGTGAGATG<br>GGCTTTCACCAGTTCGATGGTGACATTTGTAACACAATGCA<br>CTATACGAACTGGATATACATCTGCGAGGACGCGCAGTGTA<br>CGGTAGTTGAGGGTCAGGTAGACAAGAAGTGGGAGGTTCA<br>CGCCGGTGGGCAGGTCATCCTCTGCCCGGAGTCCGGGCAG<br>AGGAGGATCAAGCGTCCGCGGAGTGAAAACTGCCACCCTA<br>ACAAGCTACTGATCCTCAAGTGCCTTCGCTATCGCTTCAAG<br>AAGCATTGCAAGTTGTCGTCCACGTGGCACTGGACTTGCCA<br>CGACGGCAAGCACAAGTGGCACTGGACGTGCCACGACGGC<br>AAGCACAAGAACGCGATAGTGACGCTTACCTATGATCACAT<br>AGATTATTGGAAAGCGATCCGGCAGGAGAATGCGATATTCT<br>TCGCTGCACGCCACCAGGTGGTGCCCGCGTTGAATATCTGC<br>AAGGCGAAGGCCTGCAAGGCCATAGAGTGGAACACAGAGC<br>CGAAGCACTGCTTTAAGAAAGGCGGTCAGCACATCGAGGT<br>CTGGTTCGACTATGTGGCCTGGGACTCGGTCTACTATTGCGG<br>CGACGACGGTTGGTGCAAGACCGAGGCCGAGAAATACGGC<br>TGCAAGGGTACGTGGGAAGTTCACTTTGGTAACAGCATCGA<br>TTGCAACGACTCCATGTGCAGCACGTTTGACGATAACGTGT<br>CTGCCACGGAGTTGGTAAAGATGCACCAGAAGCGGACCGC<br>GATGTTCCAAGATCCTCAAGAGAGACCTAGAAAACTCCCGC<br>ATCTGTGCACCGAACTGCAGACCACCATCCACGACATCATC<br>CTGGAGTGCGTGTATTGCAAACAACAGCTGCTGAGAAGAG<br>AGGTGTACGACTTCGCCTTCAGAGACCTGTGCATCGTGTAC<br>CGGGACGGCAATCCCTACGCCGTGTGCGACAAGTGCCTCA<br>AGTTCTATAGCAAGATCAGCGAGTATAGATACATGCACGGC<br>GACACACCGACCCTGCACGAGTACATGCTGGACCTGCAGC<br>CCGAGACCACCGACCTGTACTGCTACGAGCAGCTGAACGA<br>CAGCAGCGAAGAGGAGGACGAGATTGACGGCCCTGCCGGC<br>CAAGCCGAGCCCGACAGAGCCCACTACAACATCGTGACCT<br>TCTGCTGTAAATGCGATAGCACACTGGACAAGTGCCTGAAG<br>TTCTACAGCAAGATTAGCGAGTACAGATATTACTGCTACTCC<br>GTGTACGGGACAACCCTGGAGCAGCAGTACAACAAGCCTC<br>TGTGCGACCTGCTGATCCGGTGTATTAACTGTCAGAAGCCA<br>CTGTGCCCTGAGGAGAAGCAGAGACACCTGGACAAGAAGC<br>AGAGATTCCACAACATCAGAGGCAGATGGACCGGCAGATG<br>CATGAGCTGCTGCAGAAGCAGCAGAACAAGAAGAGAGAC<br>ACAACTGCACTACAATATCGTCACCTTCTGCTGCAAGTGCG<br>ACTCCACACTGCGGCTCTGCGTGCAGAGCACCCACGTGGA<br>CATCAGAACCCTGGAGGACCTGCTGATGGGCACCCTGGGCA<br>TCGTGTGCCCGATCTGCAGCCAAAAGCCCATGGCTAGATTT<br>GAAGATCCCACAAGAAGACCCTACAAGCTGCCCGACCTGT<br>GCACCGAGCTGAACACAAGCCTCCAAGACATCGAGATTAC<br>CTGCGTGTACTGCAAGACCGTGCTGGAGCTGACCGAGGTG<br>TTCGAGTTCGCCTTCAAGGACCTGTTCGTGGTGTACAGAGA<br>CAGCATTCCTCACGCCGCCTGCCACAAGTGCATCGACTTCT<br>ACAGCCGGATTCGGGAACTGCGGTACTACAGCGACAGCGT<br>GATGTATGGCCCGAAGGCCACCCTGCAAGACATCGTGCTGC<br>ACCTGGAGCCTCAGAACGAAATACCCGTGGACCTGCTGTG<br>CCATGAGCAACTGAGCGACAGCGAGGAAGAGAATGATGAG<br>ATCGACGGCGTGAATCATCAGCACCTGCCCGCTAGAAGGGC<br>CGAGCCGCAACGGCACACCATGCTGTGCATGTGCTTCTACA<br>GCAGAATCAGAGAACTCCGGTATTACAGCGACTCCGTGTAC<br>GGAGACACCCTCGAGAAGCTGACCAACACCGGCCTGTACA<br>ATCTGCTGATCAGATGTCTGAGATGTCAGAAACCCTTGAAT<br>CCCGCCGAGAAGCTGAGACACCTGAACGAGAAGAGAAGAT<br>TCCACAAGATCGCCGGCCACTACAGAGGGCAGTGCCACAG<br>CTGCTGCAACAGAGCTAGACAAGAGAGACTGCAGAGAAG<br>ACGGGAGACCCAAGTGGCTAGAAGGGCTGAGCCTCAAAGA<br>CATACCATGCTGTGTATGTGCTGCAAATGCGAGGCTAGAATC<br>GAGCTGGTGGTGGAGAGCAGCGCCGACGACCTGAGAGCCT<br>TTCAGCAGCTGTTCCTGAGCACCCTGAGCTTCGTGTGTCCC<br>TGGTGCGCTAGCCAACAGTGATGA |
| 46 | Polynucleotide sequence of HPV-5 | ATGAACGTGTGCCAGGATAAGATCTTGGAGCATTACGAGAA<br>TGACTCCAAGGATATCCTGGAGCACTATGAGAACGACTCCA<br>AGGATCTATGTGATCACATCTGTGATCACATAGATTATTGGA<br>AGCACATCCGGCTGGAGTGCGCCATTATGTATAAGGCTCGG<br>ATACGGCTGGAATGTGCTATAATGTATAAAGCCCGTGAGATG<br>GGCTTTCACCAGTTCGATGGTGACATTTGTAACACAATGCA |

| SEQ ID NO. | name | sequence |
|---|---|---|
| | | CTATACGAACTGGATATACATCTGCGAGGACGCGCAGTGTA<br>CGGTAGTTGAGGGTCAGGTAGACAAGAAGTGGGAGGTTCA<br>CGCGGGTGGGCAGGTCATCCTCTGCCCGGAGTCCGGGCAG<br>AGGAGGATCAAGCGTCCGCGGAGTGAAAACTGCCACCCTA<br>ACAAGCTACTGATCCTCAAGTGCCTTCGCTATCGCTTCAAG<br>AAGCATTGCAAGTTGTCGTCCACGTGGCACTGGACTTGCCA<br>CGACGGCAAGCACAAGTGGCACTGGACGTGCCACGACGGC<br>AAGCACAAGAACGCGATAGTGACGCTTACCTATGATCACAT<br>AGATTATTGGAAAGCGATCCGGCAGGAGAATGCGATATTCT<br>TCGCTGCTAGACACCAGGTGGTGCCCGCGTTGAATATCTGC<br>AAGGCGAAGGCCTGCAAGGCCATAGAGTGGAACACAGAGC<br>CGAAGCACTGCTTTAAGAAAGGCGGTCAGCACATCGAGGT<br>CTGGTTCGACTATGTGGCCTGGGACTCGGTCTACTATTGCGG<br>CGACGACGGTTGGTGCAAGACCGAGGCCGAGAAATACGGC<br>TGCAAAGGGACGTGGGAAGTTCACTTCGGGAACTCCATCG<br>ATTGCAACGACTCCATGTGCAGCACGTTTGACGATAACGTG<br>TCTGCCACGGAGTTGGTAAAGATGGCCCGATTCGAAGATCC<br>CACAAGAAGACCCTACAAGCTGCCCGACCTGTGCACCGAG<br>CTGAACACAAGCCTCCAAGACATCGAGATTACCTGCGTGTA<br>CTGCAAGACCGTGCTGGAGCTGACCGAGGTGTTCGAGTTC<br>GCCTTCAAGGACCTGTTCGTGGTGTACAGAGACAGCATCCC<br>ACACGCCGCCTGCCACAAGTGCATCGACTTCTACAGCCGGA<br>TTCGGGAACTGCGGTACTACAGCGACAGCGTGATGTATGGG<br>CCCAAGGCCACCCTGCAAGACATCGTGCTGCACCTGGAGC<br>CTCAGAACGAAATACCCGTGGACCTGCTGTGCCATGAGCAA<br>CTGAGCGACAGCGAGGAAGAGAATGATGAGATCGACGGCG<br>TGAATCATCAGCACCTGCCCGCTAGAAGGGCCGAGCCACA<br>ACGGCACACCATGCTGTGCATGTGCTTCTACAGCAGAATCA<br>GAGAACTCCGGTATTACAGCGACTCCGTGTACGGAGATACC<br>CTCGAGAAGCTGACCAACACCGGCCTGTACAATCTGCTGAT<br>CAGATGTCTGAGATGTCAGAAACCCTTAAATCCCGCCGAGA<br>AGCTGAGACACCTGAACGAGAAGAGAAGATTCCACAAGAT<br>CGCCGGCCACTACAGAGGGCAGTGCCACAGCTGCTGCAAC<br>AGAGCTAGACAAGAGAGACTGCAGAGAAGACGGGAGACC<br>CAAGTGGCTAGAAGGGCTGAGCCGCAAAGACATACCATGC<br>TGTGTATGTGCTGCAAATGCGAGGCTAGAATCGAGCTGGTG<br>GTGGAGAGCAGCGCCGACGACCTGAGAGCCTTTCAGCAGC<br>TGTTCCTGAGCACCCTGAGCTTCGTGTGTCCCTGGTGCGCT<br>AGCCAACAGATGCATCAGAAGAGAACCGCCATGTTCCAAG<br>ATCCGCAAGAGAGACCTAGAAAACTCCCTCATCTGTGCACC<br>GAACTGCAGACCACCATCCACGACATCATCCTGGAGTGCGT<br>GTATTGCAAACAACAGCTGCTGAGAAGAGAGGTGTACGAC<br>TTCGCCTTCAGAGACCTGTGCATCGTGTACCGGGACGGCAA<br>TCCCTACGCCGTGTGCGACAAGTGCCTCAAGTTCTATAGCA<br>AGATCAGCGAGTATAGATACATGCACGGAGATACGCCGACC<br>CTGCACGAGTACATGCTGGACCTGCAGCCCGAGACCACCG<br>ACCTGTACTGCTACGAGCAGCTGAACGACAGCAGCGAAGA<br>GGAGGACGAGATTGACGGCCCGGCCGGCCAAGCCGAGCCC<br>GACAGAGCCCACTACAACATCGTGACCTTCTGCTGTAAATG<br>CGATAGCACACTGGACAAGTGCCTGAAGTTCTACAGCAAG<br>ATTAGCGAGTACAGATATTACTGCTACTCCGTGTACGGGACA<br>ACCCTGGAGCAGCAGTACAACAAGCCTCTGTGCGACCTGC<br>TGATCCGGTGTATTAACTGTCAGAAGCCCTTGTGTCCCGAG<br>GAGAAGCAGAGACACCTGGACAAGAAGCAGAGATTCCAC<br>AACATCAGAGGCAGATGGACCGGCAGATGCATGAGCTGCT<br>GCAGAAGCAGCAGAACAAGAAGAGAGACAACTGCACT<br>ACAATATCGTCACCTTCTGCTGCAAGTGCGACTCCACACTG<br>CGGCTCTGCGTGCAGAGCACCCACGTGGACATCAGAACCC<br>TGGAGGACCTGCTGATGGGCACCCTGGGCATCGTGTGTCCC<br>ATCTGCAGCCAAAAGCCCTGATGA |
| 47 | Polynucleotide sequence of tPA-SP + Flt3L + HPV-M | ATGGATGCTATGAAACGGGCCTGTGCTGCGTGCTGCTCCT<br>GTGCGGCGCTGTGTTTGTGAGCCCTAGCATCACCCAGGACT<br>GCTCCTTCCAACACAGCCCCATCTCCTCCGACTTCGCTGTC<br>AAAATCCGTGAGCTGTCTGACTACCTGCTTCAAGATTACCC<br>AGTCACCGTGGCCTCCAACCTGCAGGACGAGGAGCTCTGC<br>GGGGGCCTCTGGCGGCTGGTCCTGGCACAGCGCTGGATGG<br>AGCGGCTCAAGACTGTCGCTGGGTCCAAGATGCAAGGCTT<br>GCTGGAGCGCGTGAACACGGAGATACACTTTGTCACCAAAT<br>GTGCCTTTCAGCCCCCCCCCAGCTGTCTTCGCTTCGTCCAG<br>ACCAACATCTCCCGCCTCCTGCAGGAGACCTCCGAGCAGCT<br>GGTGGCGCTGAAGCCCTGGATCACTCGCCAGAACTTCTCCC<br>GGTGCCTGGAGCTGCAGTGTCAGCCCGACTCCTCAACCCTG<br>CCACCCCCATGGAGTCCCCGGCCCCTGGAGGCCACAGCCC |

| SEQ ID NO. | name | sequence |
|---|---|---|
| | | CGACAGCCCCGGGCGGCGGCAGCGGCGATATGCACCAGAA |
| | | GAGAACCGCCATGTTCCAGGACCCTCAGGAGAGACCTAGG |
| | | AAGCTGCCTCACCTGTGTACAGAGCTCCAGACAACCATCCA |
| | | CGACATCATCCTGGAGTGCGTGTACTGTAAGCAGCAGCTGC |
| | | TGAGAAGAGAGGTGTACGACTTCGCCTTCAGAGACCTGTG |
| | | CATCGTGTACAGAGACGGCAACCCTTACGCCGTGTGCGATA |
| | | AGTGTCTGAAGTTCTATTCCAAAATCTCCGAATATAGGTACA |
| | | TGCACGGCGACACCCCTACCCTGCACGAGTACATGCTGGAC |
| | | CTCCAGCCTGAGACCACAGACCTGTACTGCTACGAGCAGCT |
| | | GAACGACAGCTCTGAGGAAGAGGACGAGATTGACGGACCT |
| | | GCTGGCCAGGCCGAGCCTGACAGAGCCCACTACAATATCGT |
| | | GACATTCTGTTGCAAATGCGACTCCACACTGGACAAGTGCC |
| | | TGAAGTTCTACAGCAAGATCTCTGAGTACAGATACTACTGCT |
| | | ACTCTGTGTACGGCACCACACTGGAGCAGCAGTACAACAA |
| | | GCCTCTGTGCGACCTCCTGATCCGCTGCATCAACTGCCAGA |
| | | AGCCTCTGTGCCCTGAGGAGAAGCAGAGACACCTGGACAA |
| | | GAAGCAGCGGTTCCACAACATCAGAGGCAGATGGACCGGC |
| | | AGGTGCATGTCCTGCTGTAGATCCTCCAGAACCAGACGGGA |
| | | GACCCAGCTGCACTACAACATCGTGACCTTCTGCTGCAAGT |
| | | GCGACTCTACCCTGAGACTGTGCGTGCAGTCTACCCACGTG |
| | | GACATCAGAACCCTGGAGGACCTGCTGATGGGCACCCTGG |
| | | GCATCGTGTGCCCTATCTGCTCTCAGAAGCCTATGGCCAGG |
| | | TTCGAGGACCCTACCAGAAGACCCTACAAGCTGCCTGACCT |
| | | GTGCACCGAGCTGAACACCTCTCTGCAAGACATCGAGATCA |
| | | CCTGCGTGTACTGCAAGACCGTGCTGGAGCTGACCGAGGT |
| | | GTTCGAGTTCGCCTTCAAGGACCTGTTCGTGGTGTACAGAG |
| | | ACAGCATCCCTCACGCTGCCTGCCACAAGTGCATCGACTTC |
| | | TATTCCAGGATCAGGGAGCTGCGCTATTACTCCGACTCTGTG |
| | | ATGTACGGCCCCAAGGCCACCCTCCAGGACATCGTGCTGCA |
| | | CCTGGAGCCTCAGAACGAGATCCCCGTGGACCTGCTGTGCC |
| | | ACGAGCAGCTGTCTGACTCTGAAGAGGAGAACGACGAGAT |
| | | CGACGGCGTGAACCACCAGCACCTGCCTGCCAGGAGAGCT |
| | | GAACCCCAGCGGCATACCATGCTGTGTATGTGCTTCTACTCT |
| | | AGGATCAGAGAGCTGAGGTACTACTCTGACTCTGTGTACGG |
| | | CGACACCCTGGAGAAGCTGACCAACACCGGCCTGTACAAC |
| | | CTGCTGATCCGGTGCCTGAGGTGCCAGAAGCCTCTGAACCC |
| | | TGCCGAGAAGCTGAGACACCTGAACGAGAAGAGAAGATTC |
| | | CACAAGATCGCTGGCCACTACAGAGGCCAGTGCCACTCTTG |
| | | CTGCAACAGAGCCAGACAGGAGAGACTCCAGCGGAGAAG |
| | | GGAGACCCAGGTGGCCAGGAGAGCCGAGCCTCAGAGACA |
| | | CACCATGCTGTGCATGTGCTGCAAGTGCGAGGCCAGAATCG |
| | | AGCTGGTGGTGGAGAGCTCTGCCGACGACCTGAGAGCCTT |
| | | CCAGCAGCTGTTCCTGTCTACCCTGAGCTTCGTGTGCCCTT |
| | | GGTGCGCCTCTCAGCAGTAA |
| 48 | Polynucleotide sequence-1 of tPA-SP + Flt3L + HPV-1 | ATGGACGCC -continued Sequence listing

| SEQ ID NO. | name | sequence |
|---|---|---|
| | | AAGATTCCACAAGATCGCCGGCCACTACAGAGGGCAGTGC |
| | | CACAGCTGCTGCAACAGAGCTAGACAAGAGAGACTGCAGA |
| | | GACGGCGGGAAACCCAAGTGGCTAGAAGGGCCGAGCCTCA |
| | | GAGACATACAATGCTGTGCATGTGCTGCAAGTGCGAAGCTA |
| | | GAATCGAGCTGGTGGTGGAGAGCAGCGCCGACGACCTGAG |
| | | AGCCTTTCAGCAGCTGTTCCTGAGCACCCTGAGCTTCGTGT |
| | | GCCCCTGGTGCGCTAGCCAACAGATGCATCAGAAGAGAAC |
| | | CGCCATGTTCCAAGACCCCCAAGAGAGACCTAGAAAGCTG |
| | | CCCCACCTGTGTACCGAGCTGCAGACAACCATCCACGACAT |
| | | CATCCTGGAGTGCGTGTACTGCAAGCAGCAACTGCTGAGA |
| | | AGAGAGGTGTACGACTTCGCCTTCAGAGACCTGTGCATCGT |
| | | GTACCGGGACGGGAATCCCTACGCCGTGTGCGACAAATGTC |
| | | TCAAGTTTTATAGCAAGATTAGCGAGTACAGATACATGCACG |
| | | GCGACACCCCCACCCTGCACGAGTACATGCTGGACCTGCA |
| | | GCCCGAGACCACCGACCTGTACTGCTACAACAACTGAAC |
| | | GACAGCTCCGAGGAAGAGGACGAAATCGACGGCCCCGCCG |
| | | GCCAAGCCGAGCCCGACAGAGCCCACTACAACATTGTGAC |
| | | ATTCTGTTGCAAGTGTGACAGCACCCTGGACAAATGCCTGA |
| | | AGTTCTACAGCAAGATCAGCGAGTACAGATATTACTGCTAC |
| | | AGCGTGTACGGCACCACCCTGGAGCAGCAGTACAACAAGC |
| | | CCCTGTGTGACCTGCTGATTAGATGCATCAACTGTCAGAAG |
| | | CCCCTGTGCCCCGAGGAGAAGCAGAGACACCTGGACAAGA |
| | | AGCAGAGATTCCACAACATCAGAGGCAGATGGACCGGCAG |
| | | ATGCATGAGCTGCTGCAGAAGCAGCAGAACAAGAAGAGAG |
| | | ACACAGCTGCACTACAATATCGTGACCTTTTGCTGCAAGTG |
| | | CGATAGCACCCTGCGGCTGTGCGTGCAGAGCACCCACGTG |
| | | GACATCAGAACCCTGGAGGACCTGCTGATGGGCACCCTGG |
| | | GCATCGTGTGCCCCATCTGCAGCCAAAAGCCCTGATGA |
| 49 | Polynucleotide sequence-2 of tPA-SP + Flt3L + HPV-1 | ATGGACGCCATGAAGCGCGGGCTTTGCTGCGTCCTGCTGTT |
| | | ATGCGGCGCTGTGTTCGTCAGCCCTAGCATAACGCAGGACT |
| | | GCAGCTTCCAGCACAGCCCTATATCTTCGGACTTCGCGGTC |
| | | AAGATTCGGGAGCTCTCCGACTATCTGCTCCAGGACTATCC |
| | | CGTCACGGTCGCCAGCAACCTTCAGGACGAAGAGTTGTGT |
| | | GGCGGCCTGTGGCGGTTAGTCCTGGCGCAGCGTTGGATGG |
| | | AGCGCCTGAAGACCGTGGCTGGTTCGAAGATGCAGGGCTT |
| | | GCTGGAGCGGGTGAACACGGAGATTCACTTCGTGACCAAG |
| | | TGCGCGTTTCAGCCTCCGCCGAGCTGTCTGAGGTTCGTGCA |
| | | GACGAACATCAGTCGGCTCTTGCAGGAGACTAGCGAGCAG |
| | | TTGGTCGCGTTGAAGCGTGGATCACCCGCCAGAACTTTAG |
| | | TCGGTGCCTCGAGCTGCAGTGCCAGCCAGATTCCTCGACCC |
| | | TCCCTCCGCCGTGGTCGCCGCGGCCGCTGGAGGCCACGGC |
| | | GCCCACGGCGCCTGGCGGCGGGAGCGGTGACATGGCGCGG |
| | | TTCGAGGACCCGACTCGCAGGCCGTATAAGTTACCGGATCT |
| | | CTGTACAGAGCTGAACACGTCCTTGCAGGACATCGAAATCA |
| | | CCTGCGTGTACTGCAAGACCGTCTTGGAGTTAACGGAGGTG |
| | | TTCGAGTTCGCCTTCAAGGACTTGTTCGTTGTGTACAGAGA |
| | | TTCGATACCTCATGCGGCCTGCCACAAGTGCATCGATTTCTA |
| | | TTCGCGCATTCGAGAGCTGAGGTACTACTCGGACAGTGTCA |
| | | TGTACGGGCCTAAGGCCACGTTACAGGACATTGTCCTCCAC |
| | | CTGGAACCTCAGAATGAGATTCCGGTGGACCTGCTCTGCCA |
| | | TGAGCAGCTCTCGGACTCCGAGGAAGAGAACGATGAGATC |
| | | GACGGAGTGAACCATCAGCACCTGCCCGCGAGAAGGGCAG |
| | | AGCCACAGCGTCACACAATGCTGTGTATGTGCTTCTACTCG |
| | | CGGATCAGGGAGCTGAGGTATTACTCCGACTCGGTCTACGG |
| | | AGACACCTTAGAGAAGTTGACAAACACCGGTTTGTACAAC |
| | | CTTCTCATAAGGTGTCTCCGTTGCCAAAAGCCTCTGAATCC |
| | | GGCGGAGAAGCTGCGGCATCTCAACGAGAAGCGGCCGTTT |
| | | CACAAGATCGCCGGGCACTACAGAGGACAGTGCCACAGCT |
| | | GCTGCAACCGCGCCAGACAGGAGCGGTTCAGCGGCGGCG |
| | | CGAGACCCAGGTTGCCCGGCGAGCCGAGCCGCAGCGACAT |
| | | ACAATGCTTTGTATGTGCTGCAAGTGCGAGGCTCGGATAGA |
| | | GCTTGTCGTGGAATCTTCTGCGGATGACCTGCGAGCATTCC |
| | | AGCAGCTGTTTCTGAGCACTCTGTCGTTCGTGTGCCCGTGG |
| | | TGCGCGAGCCAGCAGATGCATCAGAAGCGGACTGCTATGTT |
| | | CCAAGACCCGCAGGAGAGGCCACGCAAGCTTCCACATCTG |
| | | TGTACAGAGCTCCAAACACCATCCACGACATCATCCTGGA |
| | | GTGCGTGTACTGCAAACAGCAGCTGCTGAGAAGAGAGGTG |
| | | TACGACTTCGCCTTCAGAGACCTGTGCATCGTGTACAGAGA |
| | | TGGGAATCCCTACGCCGTGTGCGACAAGTGCCTGAAGTTCT |
| | | ATAGCAAGATCAGCGAGTACAGATACATGCATGGCGACACA |
| | | CCCACCCTGCACGAGTACATGCTGGACCTGCAGCCCGAGA |
| | | CCACCGACCTGTACTGCTATGAGCAGCTGAACGACAGCAG |
| | | CGAAGAGGAGGACGAGATCGACGGCCCCGCTGGCCAAGCC |

| SEQ ID NO. | name | sequence |
|---|---|---|
| | | GAGCCCGACAGAGCCCACTATAACATCGTCACATTCTGTTG |
| | | CAAATGTGACTCCACCCTGGACAAGTGTCTGAAATTCTATA |
| | | GCAAGATCTCCGAGTACCGGTACTACTGTTACAGCGTGTAC |
| | | GGCACCACACTGGAGCAGCAGTACAACAAGCCGCTTTGCG |
| | | ATCTGCTGATCCGGTGCATCAACTGTCAGAAGCCCTTGTGT |
| | | CCCGAAGAGAAGCAGAGACACCTGGACAAGAAGCAGAGA |
| | | TTCCACAACATCAGAGGCAGATGGACCGGCAGATGCATGA |
| | | GCTGCTGCAGAAGCAGCAGAACCCGGAGAGAGACCCAACT |
| | | CCACTACAATATCGTGACCTTCTGTTGCAAGTGCGATAGCAC |
| | | CCTGAGACTGTGCGTGCAGAGCACCCACGTGGACATCAGA |
| | | ACCCTGGAGGACCTGCTGATGGGCACCCTGGGCATCGTGTG |
| | | CCCTATCTGCAGCCAAAAGCCCTGATGA |
| 50 | Polynucleotide sequence of tPA-SP + Flt3L + HPV-2 | ATGGACGCCATGAAGAGAGGCCTGTGCTGCGTGCTGCTCCT |
| | | GTGCGGCGCCGTGTTCGTGAGCCCTAGCATCACCCAAGACT |
| | | GCAGCTTTCAGCACAGCCCCATCAGCAGCGACTTCGCCGTG |
| | | AAGATCAGAGAACTCAGCGACTACCTGCTGCAAGACTACC |
| | | CCGTGACCGTGGCTAGCAACCTGCAAGACGAGGAGCTGTG |
| | | CGGCGGCCTGTGGAGACTGGTGCTGGCTCAGAGATGGATG |
| | | GAGAGACTGAAGACCGTGGCCGGCAGCAAGATGCAAGGCC |
| | | TGCTGGAGAGAGTGAACACCGAGATCCACTTCGTGACCAA |
| | | GTGCGCCTTTCAGCCCCCTCCTAGCTGCCTGAGATTCGTGC |
| | | AGACCAACATCAGCAGACTGCTGCAAGAGACAAGCGAGCA |
| | | GCTGGTGGCCCTGAAGCCCTGGATCACAAGACAGAACTTC |
| | | AGCAGATGCCTGGAGCTGCAATGTCAGCCCGACAGCAGCA |
| | | CCCTCCCCCCTCCCTGGAGCCCTAGACCCCTCGAAGCCACC |
| | | GCTCCCACCGCCCCGGCGGGGCAGCGGCGACATGGCTA |
| | | GATTCGAGGACCCCACAAGAAGACCCTACAAGCTGCCCGA |
| | | TCTCTGCACAGAGCTGAACACAAGCCTGCAAGACATCGAG |
| | | ATCACCTGCGTGTATTGCAAGACCGTGCTGGAGCTGACCGA |
| | | GGTGTTCGAGTTCGCCTTCAAGGACCTGTTCGTGGTGTACA |
| | | GAGACAGCATCCCCCACGCCGCCTGCCACAAGTGCATCGA |
| | | CTTCTACAGCCGGATCAGAGAGCTCCGGTACTACAGCGACT |
| | | CCGTGATGTACGGCCCCAAGGCCACCCTCCAAGACATCGTG |
| | | CTGCACCTGGAGCCTCAGAACGAGATCCCCGTGGACCTGCT |
| | | GTGCCACGAGCAGCTGAGCGACAGCGAGGAAGAGAACGA |
| | | CGAAATTGACGGCGTGAACCATCAGCACCTGCCCGCTAGAC |
| | | GGGCCGAGCCTCAGCGGCACACCATGCTGTGTATGTGCTTC |
| | | TACAGCAGAATCAGAGAACTCAGATATTACTCCGACTCCGT |
| | | GTACGGCGACACACTGGAGAAGCTGACCAACACCGGCCTG |
| | | TACAACCTGCTGATCAGATGCCTGAGATGTCAGAAGCCTCT |
| | | CAATCCCGCCGAGAAGCTGAGACACCTGAACGAGAAGAGA |
| | | AGATTCCACAAGATCGCCGGCCACTACAGAGGGCAGTGCC |
| | | ACAGCTGCTGCAACAGAGCTAGACAAGAGAGACTGCAGAG |
| | | AAGACGGGAGACCCAAGTGGCTAGAAGGGCCGAGCCTCA |
| | | GAGACACACCATGCTGTGCATGTGCTGCAAGTGCGAAGCTA |
| | | GAATCGAGCTGGTGGTGGAGAGCAGCGCCGACGACCTGAG |
| | | AGCCTTTCAGCAGCTGTTCCTGAGCACCCTGAGCTTCGTGT |
| | | GCCCCTGGTGCGCTAGCCAACAGATGCATCAGAAGAGAAC |
| | | CGCCATGTTCCAAGACCCCCAAGAGAGACCTAGAAAGCTG |
| | | CCCCACCTGTGTACAGAGCTCCAAACCACCATCCACGACAT |
| | | CATCCTGGAGTGCGTGTACTGCAAACAGCAGCTGCTGAGA |
| | | AGAGAGGTGTACGACTTCGCCTTCAGAGACCTGTGCATCGT |
| | | GTACAGAGATGGGAATCCCTACGCCGTGTGCGACAAGTGCC |
| | | TGAAGTTTTATAGCAAGATCAGCGAGTACAGATACATGCAT |
| | | GGCGACACCCCCACCCTGCACGAGTACATGCTGGACCTGC |
| | | AGCCCGAGACCACCGACCTGTACTGCTATGAGCAGCTGAA |
| | | CGACAGCAGCGAAGAGGAGGACGAGATCGACGGCCCCGCT |
| | | GGCCAAGCCGAGCCCGACAGAGCCCACTATAACATCGTCA |
| | | CATTCTGTTGCAAATGTGACTCCACCCTGGACAAGTGTCTG |
| | | AAATTCTATAGCAAGATCTCCGAGTACCGGTACTACTGTTAC |
| | | AGCGTGTACGGCACCACACTGGAGCAGCAGTACAACAAGC |
| | | CCCTGTGCGATCTGCTGATCCGGTGCATCAACTGTCAGAAG |
| | | CCCTGTGTCCCGAAGAGAAGCAGAGACACCTGGACAAGA |
| | | AGCAGAGATTCCACAACATCAGAGGCAGATGGACCGGCAG |
| | | ATGCATGAGCTGCTGCAGAAGCAGCAGAACCCGGAGAGAG |
| | | ACCCAACTCCACTACAATATCGTGACCTTCTGTTGCAAGTG |
| | | CGATAGCACCCTGAGACTGTGCGTGCAGAGCACCCACGTG |
| | | GACATCAGAACCCTGGAGGACCTGCTGATGGGCACCCTGG |
| | | GCATCGTGTGCCCCATCTGCAGCCAAAAGCCCTGATGA |

Sequence listing

| SEQ ID NO. | name | sequence |
|---|---|---|
| 51 | Polynucleotide sequence of tPA-SP + Flt3L + HPV-3 | ATGGACGCCATGAAGAGAGGCCTGTGCTGCGTGCTGCTCCT GTGCGGCGCCGTGTTCGTGAGCCCTAGCATCACCCAAGACT GCAGCTTTCAGCACAGCCCCATCAGCAGCGACTTCGCCGTG AAGATCCGGGAGCTGTCCGACTACCTGCTGCAAGACTACCC CGTGACCGTGGCTAGCAACCTGCAAGACGAGGAGCTGTGC GGCGGCCTGTGGAGACTGGTGCTGGCTCAGAGATGGATGG AGAGACTGAAGACCGTGGCCGGCAGCAAGATGCAAGGCCT GCTGGAGAGAGTGAACACCGAGATCCACTTCGTGACCAAG TGCGCCTTTCAGCCCCCTCCTAGCTGCCTGAGATTCGTGCA GACCAACATCAGCAGACTGCTGCAAGAGACAAGCGAGCAG CTGGTGGCCCTGAAGCCCTGGATCACAAGACAGAACTTCA GCAGATGCCTGGAACTCCAATGTCAGCCCGACAGCAGCAC CCTGCCTCCCCCTGGAGCCCTAGACCCCTCGAAGCCACAG CCCCCACAGCCCCGGGGGGGCAGCGGCGACATGCATCA GAAGAGAACCGCCATGTTCCAAGACCCCCAAGAGAGACCT AGAAAGCTGCCCCACCTGTGCACCGAGCTGCAGACCACCA TCCACGACATCATCCTGGAGTGCGTGTACTGTAAGCAGCAG CTGCTGAGAAGAGAGGTGTACGACTTCGCCTTCAGAGACC TGTGCATCGTGTATAGAGACGGCAACCCCTACGCCGTGTGC GATAAGTGCCTGAAATTCTACTCCAAGATCAGCGAGTACAG ATACGCCGCCATGCACGGCGACACCCCCACCCTGCACGAGT ACATGCTGGACCTGCAGCCCGAGACCACCGACCTGTACTGC TACGAGCAGCTGAACGACAGCTCCGAAGAGGAGGACGAGA TCGACGGCCCCGCCGGCCAAGCCGAGCCCGACAGAGCTCA CTACAATATCGTGACATTCTGCTGCAAGTGCGACTCCACAC TGGCTGCCGACAAGTGCCTCAAGTTTTACAGCAAGATCTCC GAATACAGATACTACTGCTACAGCGTGTACGGGACCACCCT GGAGCAGCAGTACAACAAACCTCTCTGCGACCTGCTGATTA GATGCATTAATTGTCAGAAGCCCCTGTGCCCCGAGGAGAAG CAGAGACACCTGGACAAGAAGCAGAGATTCCACAACATCA GAGGCAGATGGACCGGCAGATGCATGAGCTGCTGCAGAAG CAGCAGAACAAGAAGAGAGACACAGCTGGCCGCTCACTAC AACATCGTCACCTTCTGTTGTAAGTGCGACTCCACCCTGAG ACTGTGCGTGCAGAGCACCCACGTGGACATCAGAACCCTG GAGGACCTGCTGATGGGCACCCTGGGCATCGTGTGCCCCAT CTGCAGCCAAAAGCCCATGGCTAGATTCGAGGACCCCACA AGAAGACCCTACAAGCTGCCCGACCTGTGTACAGAACTGA ACACAAGCCTGCAAGACATCGAGATCACCTGCGTGTACTGC AAGACCGTGCTGGAGCTGACCGAGGTGTTCGAGTTCGCCT TCAAGGACCTGTTCGTGGTGTACAGAGACAGCATCCCCCAC GCCGCCTGCCACAAGTGCATCGACTTCTACAGCAGAATTAG AGAACTGCGGTACTACAGCGACAGCGTGGCCGCCATGTAC GGCCCCAAGGCCACCCTCCAAGACATCGTGCTGCACCTCG AGCCTCAGAACGAGATCCCCGTGGACCTGCTGTGCCACGA ACAGCTGAGCGACAGCGAGGAAGAGAACGACGAGATTGA CGGCGTGAACCATCAGCACCTGCCCGCTCGGAGAGCTGAG CCCCAACGGCACACCATGCTGTGTATGTGTGCCGCTTTCTAT AGCAGAATCCGGGAGCTGCGGTACTATTCCGACAGCGTGTA CGGGGACACACTGGAGAAGCTGACCAACACCGGCCTGTAC AATCTGCTGATCAGATGCCTCAGATGTCAGAAACCCCTCAA CCCTGCCGAGAAGCTGAGACACCTGAACGAGAAGAGAAGA TTCCACAAGATCGCCGGCCACTACAGAGGGCAGTGCCACA GCTGCTGCAACAGAGCTAGACAAGAGAGACTGCAGAGACG GAGAGAGACCCAAGTGGCCGCTGCTAGAAGGGCCGAGCCT CAGAGACACACAATGCTGTGCATGTGCTGCAAATGCGAGG CTAGAATCGAGCTGGTGGTGGAGAGCAGCGCCGACGACCT GAGAGCCTTTCAGCAGCTGTTCCTGAGCACCCTGAGCTTCG TGTGCCCCTGGTGCGCTAGCCAACAGTGATGA |
| 52 | Polynucleotide sequence-1 of tPA-SP +Flt3L + HPV-4 | ATGGACGCCATGAAGAGAGGCCTGTGCTGCGTGCTGCTCCT GTGCGGCGCCGTGTTCGTGAGCCCTAGCATCACCCAAGACT GCAGCTTTCAGCACAGCCCCATCAGCAGCGACTTCGCCGTG AAGATCAGAGAGCTGAGCGACTACCTGCTGCAAGACTACCC CGTGACCGTGGCTAGCAACCTGCAAGACGAGGAGCTGTGC CGGCGGCCTGTGGAGACTGGTGCTGGCTCAGAGATGGATG GAGAGACTGAAGACCGTGGCCGGCAGCAAGATGCAAGGCC TGCTGGAGAGAGTGAACACCGAGATCCACTTCGTGACCAA GTGCGCCTTTCAGCCCCCTCCTAGCTGCCTGAGATTCGTGC AGACCAACATCAGCAGACTGCTGCAAGAGACAAGCGAGCA GCTGGTGGCCCTGAAGCCCTGGATCACAAGACAGAACTTC AGCAGATGCCTGGAGCTGCAGTGTCAGCCTGACAGCAGCA CCCTCCCCCCTCCCTGGAGCCCCGGCCTCTGGAGGCTACA GCCCCACAGCCCCGGCGGGGGCAGCGGCGACATGAACG |

| SEQ ID NO. | name | sequence |
|---|---|---|
| | | TGTGCCAAGACAAGATCCTGGAACACTACGAGAATGACAG
CAAAGACATTCTGGAGCACTACGAAAATGATTCCAAGGACC
TGTGTGACCATATCTGTGATCATATCGATTATTGGAAGCACAT
CAGACTGGAATGTGCTATCATGTACAAGGCCCGGATCAGAC
TGGAGTGCGCCATCATGTACAAGGCTCGGGAAATGGGCTTC
CATCAGTTCGACGGCGACATCTGCAACACCATGCACTACAC
CAACTGGATCTACATCTGCGAGGACGCTCAGTGCACCGTGG
TGGAGGGCCAAGTGGACAAGAAGTGGGAGGTGCACGCCG
GCGGCCAAGTGATCCTGTGCCCTGAAAGCGGGCAGAGAAG
AATCAAGAGACCCCGGAGCGAGAACTGCCACCCCAACAAG
CTGCTGATCCTGAAGTGCCTGAGATACAGATTCAAGAAGCA
CTGCAAGCTGAGCAGCACCTGGCACTGGACCTGCCATGATG
GCAAACACAAGTGGCACTGGACCTGCCACGACGGCAAGCA
TAAGAATGCCATCGTGACCCTGACCTACGACCACATCGATTA
TTGGAAGGCCATCAGACAAGAGAACGCCATCTTCTTCGCCG
CTAGACACCAAGTGGTGCCCGCCCTGAACATCTGCAAGGC
CAAGGCCTGCAAGGCCATCGAGTGGAACACCGAGCCCAAG
CACTGCTTCAAGAAGGGCGGGCAGCACATCGAGGTGTGGT
TCGACTACGTCGCCTGGGATAGCGTGTACTACTGCGGCGAC
GACGGCTGGTGCAAGACCGAGGCCGAGAAGTACGGCTGCA
AGGGCACCTGGGAGGTCCACTTCGGCAACAGCATCGACTG
CAACGACAGCATGTGCAGCACCTTCGACGACAACGTGAGC
GCCACCGAGCTGGTGAAGATGCATCAGAAGAGAACCGCCA
TGTTCCAAGACCCCAAGAGAGACCTAGAAAACTCCCCCA
TCTGTGCACCGAACTGCAGACCACCATCCACGACATCATCC
TGGAGTGCGTGTATTGCAAACAACAGCTGCTGAGAAGAGA
GGTGTACGACTTCGCCTTCAGAGACCTGTGCATCGTGTACC
GGGACGGCAATCCCTACGCCGTGTGCGACAAGTGCCTCAA
GTTTTATAGCAAGATCAGCGAGTATAGATACATGCACGGGG
ACACCCCCACCCTGCACGAGTACATGCTGGACCTGCAGCCC
GAGACCACCGACCTGTACTGCTACGAGCAGCTGAACGACA
GCAGCGAAGAGGAGGACGAGATTGACGGCCCCGCCGGCCA
AGCCGAGCCCGACAGAGCCCACTACAACATCGTGACCTTCT
GCTGTAAATGCGATAGCACACTGGACAAGTGCCTGAAGTTC
TACAGCAAGATTAGCGAGTACAGATATTACTGCTACTCCGTG
TACGGGACAACCCTGGAGCAGCAGTACAACAAGCCTCTGT
GCGACCTGCTGATCCGGTGTATTAACTGTCAGAAGCCCCTG
TGCCCCGAGGAGAAGCAGAGACCACCTGGACAAGAAGCAG
AGATTCCACAACATCAGAGGCAGATGGACCGGCAGATGCAT
GAGCTGCTGCAGAAGCAGCAGAACAAGAAGAGAGACACA
ACTGCACTACAATATCGTCACCTTCTGCTGCAAGTGCGACT
CCACACTGCGGCTCTGCGTGCAGAGCACCCACGTGGACAT
CAGAACCCTGGAGGACCTGCTGATGGGCACCCTGGGCATC
GTGTGCCCCATCTGCAGCCAAAAGCCCATGGCTAGATTCGA
GGACCCCACAAGAAGACCCTACAAGCTGCCCGACCTGTGC
ACCGAGCTGAACACAAGCCTCCAAGACATCGAGATTACCT
GCGTGTACTGCAAGACCGTGCTGGAGCTGACCGAGGTGTT
CGAGTTCGCCTTCAAGGACCTGTTCGTGGTGTACAGAGACA
GCATCCCCCACGCCGCCTGCCACAAGTGCATCGACTTCTAC
AGCCGGATTCGGGAACTGCGGTACTACAGCGACAGCGTGA
TGTATGGCCCCAAGGCCACCCTGCAAGACATCGTGCTGCAC
CTGGAGCCTCAGAACGAAATCCCCGTGGACCTGCTGTGCCA
TGAGCAACTGAGCGACAGCGAGGAAGAGAATGATGAGATC
GACGGCGTGAATCATCAGCACCTGCCCGCTAGAAGGGCCG
AGCCCCAACGGCACACCATGCTGTGCATGTGCTTCTACAGC
AGAATCAGAGAACTCCGGTATTACAGCGACTCCGTGTACGG
GGATACCCTCGAGAAGCTGACCAACACCGGCCTGTACAATC
TGCTGATCAGATGTCTGAGATGTCAGAAACCCCTGAACCCC
GCCGAGAAGCTGAGACACCTGAACGAGAAGAGAAGATTCC
ACAAGATCGCCGGCCACTACAGAGGGCAGTGCCACAGCTG
CTGCAACAGAGCTAGACAAGAGAGACTGCAGAGAAGACG
GGAGACCCAAGTGGCTAGAAGGGCTGAGCCCCAAAGACAT
ACCATGCTGTGTATGTGCTGCAAATGCGAGGCTAGAATCGA
GCTGGTGGTGGAGAGCAGCGCCGACGACCTGAGAGCCTTT
CAGCAGCTGTTCCTGAGCACCCTGAGCTTCGTGTGCCCCTG
GTGCGCTAGCCAACAGTGATGA |
| 53 | Polynucleotide sequence-2 of tPA-SP + Flt3L + HPV-4 | ATGGACGCCATGAAGCGCGGTCTGTGCTGCGTCCTGCTGTT
ATGCGGCGCTGTGTTCGTCAGCCCTAGCATAACGCAGGACT
GCAGCTTCCAGCACAGCCCTATATCTTCGGACTTCGCGGTC
AAGATTCGGGAGCTCTCCGACTATCTGCTCCAGGACTATCC
CGTCACGGTCGCCAGCAACCTTCAGGACGAAGAGTTGTGT
GGCGGCCTGTGCGCGGTTAGTCCTGGCGCAGCGTTGGATGG
AGCGCCTGAAGACCGTGGCTGGTTCGAAGATGCAGGGCTT |

| SEQ ID NO. | name | sequence |
|---|---|---|
| | | GCTGGAGCGGGTGAACACGGAGATTCACTTCGTGACCAAG |
| | | TGCGCGTTTCAGCCTCCGCCGAGCTGTCTGAGGTTCGTGCA |
| | | GACGAACATCAGTCGGCTCTTGCAGGAGACTAGCGAGCAG |
| | | TTGGTCGCGTTGAAGCCGTGGATCACCCGCCAGAACTTCTC |
| | | ACGTTGCCTTGAGCTGCAGTGCCAGCCGGATTCCTCGACCC |
| | | TCCCTCCGCCGTGGTCGCCGCGGCCGCTGGAGGCCACGGC |
| | | GCCCACGGCGCCTGGCGGAGGGTCGGGCGACATGAACGTG |
| | | TGCCAGGATAAGATCTTGGAGCATTACGAGAATGACTCCAA |
| | | GGATATCCTGGAGCACTATGAGAACGACTCCAAGGATCTAT |
| | | GTGATCACATCTGTGATCACATAGATTATTGGAAGCACATCC |
| | | GGCTGGAGTGCGCCATTATGTATAAGGCGCGTATCCGGCTG |
| | | GAATGTGCTATAATGTATAAAGCCCGTGAGATGGGCTTTCAC |
| | | CAGTTCGATGGTGACATTTGTAACACAATGCACTATACGAA |
| | | CTGGATATACATCTGCGAGGACGCGCAGTGTACGGTAGTTG |
| | | AGGGTCAGGTAGACAAGAAGTGGGAGGTTCACGCCGGTGG |
| | | GCAGGTCATCCTCTGCCCGGAGTCCGGGCAGAGGAGGATC |
| | | AAGCGTCCGCGGAGTGAAAACTGCCACCCTAACAAGCTAC |
| | | TGATCCTCAAGTGCCTTCGCTATCGCTTCAAGAAGCATTGC |
| | | AAGTTGTCGTCCACGTGGCACTGGACTTGCCACGACGGCA |
| | | AGCACAAGTGGCACTGGACGTGCCACGACGGCAAGCACAA |
| | | GAACGCGATAGTGACGCTTACCTATGATCACATAGATTATTG |
| | | GAAAGCGATCCGGCAGGAGAATGCGATATTCTTCGCTGCAC |
| | | GCCACCAGGTGGTGCCCGCGTTGAATATCTGCAAGGCGAA |
| | | GGCCTGCAAGGCCATAGAGTGGAACACAGAGCCGAAGCAC |
| | | TGCTTTAAGAAAGGCGGTCAGCACATCGAGGTCTGGTTCGA |
| | | CTATGTGGCCTGGGACTCGGTCTACTATTGCGGCGACGACG |
| | | GTTGGTGCAAGACCGAGGCCGAGAAATACGGCTGCAAGGG |
| | | TACGTGGGAAGTTCACTTTGGTAACAGCATCGATTGCAACG |
| | | ACTCCATGTGCAGCACGTTTGACGATAACGTGTCTGCCACG |
| | | GAGTTGGTAAAGATGCACCAGAAGCGGACCGCGATGTTCC |
| | | AAGATCCTCAAGAGAGACCTAGAAAACTCCCGCATCTGTGC |
| | | ACCGAACTGCAGACCACCATCCACGACATCATCCTGGAGTG |
| | | CGTGTATTGCAAACAACAGCTGCTGAGAAGAGAGGTGTAC |
| | | GACTTCGCCTTCAGAGACCTGTGCATCGTGTACCGGGACGG |
| | | CAATCCCTACGCCGTGTGCGACAAGTGCCTCAAGTTCTATA |
| | | GCAAGATCAGCGAGTATAGATACATGCACGGCGACACACCG |
| | | ACCCTGCACGAGTACATGCTGGACCTGCAGCCCGAGACCA |
| | | CCGACCTGTACTGCTACGAGCAGCTGAACGACAGCAGCGA |
| | | AGAGGAGGACGAGATTGACGGCCCTGCCGGCCAAGCCGAG |
| | | CCCGACAGAGCCCACTACAACATCGTGACCTTCTGCTGTAA |
| | | ATGCGATAGCACACTGGACAAGTGCCTGAAGTTCTACAGCA |
| | | AGATTAGCGAGTACAGATATTACTGCTACTCCGTGTACGGGA |
| | | CAACCCTGGAGCAGCAGTACAACAAGCCTCTGTGCGACCT |
| | | GCTGATCCGGTGTATTAACTGTCAGAAGCCACTGTGCCCTG |
| | | AGGAGAAGCAGAGACACCTGGACAAGAAGCAGAGATTCC |
| | | ACAACATCAGAGGCAGATGGACCGGCAGATGCATGAGCTG |
| | | CTGCAGAAGCAGCAGAACAAGAAGAGAGACACAACTGCA |
| | | CTACAATATCGTCACCTTCTGCTGCAAGTGCGACTCCACAC |
| | | TGCGGCTCTGCGTGCAGAGCACCCACGTGGACATCAGAAC |
| | | CCTGGAGGACCTGCTGATGGGCACCCTGGGCATCGTGTGCC |
| | | CGATCTGCAGCCAAAAGCCCATGGCTAGATTTGAAGATCCC |
| | | ACAAGAAGACCCTACAAGCTGCCCGACCTGTGCACCGAGC |
| | | TGAACACAAGCCTCCAAGACATCGAGATTACCTGCGTGTAC |
| | | TGCAAGACCGTGCTGGAGCTGACCGAGGTGTTCGAGTTCG |
| | | CCTTCAAGGACCTGTTCGTGGTGTACAGAGACAGCATTCCT |
| | | CACGCCGCCTGCCACAAGTGCATCGACTTCTACAGCCGGAT |
| | | TCGGGAACTGCGGTACTACAGCGACAGCGTGATGTATGGCC |
| | | CGAAGGCCACCCTGCAAGACATCGTGCTGCACCTGGAGCC |
| | | TCAGAACGAAATACCCGTGGACCTGCTGTGCCATGAGCAAC |
| | | TGAGCGACAGCGAGGAAGAGAATGATGAGATCGACGGCGT |
| | | GAATCATCAGCACCTGCCCGCTAGAAGGGCCGAGCCGCAA |
| | | CGGCACACCATGCTGTGCATGTGCTTCTACAGCAGAATCAG |
| | | AGAACTCCGGTATTACAGCGACTCCGTGTACGGAGACACCC |
| | | TCGAGAAGCTGACCAACACCGGCCTGTACAATCTGCTGATC |
| | | AGATGTCTGAGATGTCAGAAACCCTTGAATCCCGCCGAGAA |
| | | GCTGAGACACCTGAACGAGAAGAGAAGATTCCACAAGATC |
| | | GCCGGCCACTACAGAGGGCAGTGCCACAGCTGCTGCAACA |
| | | GAGCTAGACAAGAGAGACTGCAGAGAAGACGGGAGACCC |
| | | AAGTGGCTAGAAGGGCTGAGCCTCAAAGACATACCATGCT |
| | | GTGTATGTGCTGCAAATGCGAGGCTAGAATCGAGCTGGTGG |
| | | TGGAGAGCAGCGCCGACGACCTGAGAGCCTTTCAGCAGCT |
| | | GTTCCTGAGCACCCTGAGCTTCGTGTGTCCCTGGTGCGCTA |
| | | GCCAACAGTGATGA |

| SEQ ID NO. | name | sequence |
|---|---|---|
| 54 | Polynucleotide sequence of tPA-SP + Flt3L + HPV-5 | ATGGACGCCATGAAGCGCGGTCTTTGCTGCGTCCTGCTGTT ATGCGGCGCTGTGTTCGTCAGCCCTAGCATAACGCAGGACT GCAGCTTCCAGCACAGCCCTATATCTTCGGACTTCGCGGTC AAGATTCGGGAGCTCTCCGACTATCTGCTCCAGGACTATCC CGTCACGGTCGCCAGCAACCTTCAGGACGAAGAGTTGTGT GGCGGCCTGTGGCGGTTAGTCCTGGCGCAGCGTTGGATGG AGCGCCTGAAGACCGTGGCTGGTTCGAAGATGCAGGGCTT GCTGGAGCGGGTGAACACGGAGATTCACTTCGTGACCAAG TGCGCGTTTCAGCCTCCGCCGAGCTGTCTGAGGTTCGTGCA GACGAACATCAGTCGGCTCTTGCAGGAGACTAGCGAGCAG TTGGTCGCGTTGAAGCCGTGGATCACCCGCCAGAACTTCTC ACGTTGCCTTGAGCTGCAGTGCCAGCCGGATTCCTCGACCC TCCCTCCGCCGTGGTCGCCGCGGCCGCTGGAGGCCACGGC GCCCACGGCGCCTGGCGGCGGGAGCGGAGATATGAACGTG TGCCAGGATAAGATCTTGGAGCATTACGAGAATGACTCCAA GGATATCCTGGAGCACTATGAGAACGACTCCAAGGATCTAT GTGATCACATCTGTGATCACATAGATTATTGGAAGCACATCC GGCTGGAGTGCGCCATTATGTATAAGGCTCGGATACGGCTG GAATGTGCTATAATGTATAAAGCCCGTGAGATGGGCTTTCAC CAGTTCGATGGTGACATTTGTAACACAATGCACTATACGAA CTGGATATACATCTGCGAGGACGCGCAGTGTACGGTAGTTG AGGGTCAGGTAGACAAGAAGTGGGAGGTTCACGCGGGTGG GCAGGTCATCCTCTGCCCGGAGTCCGGGCAGAGGAGGATC AAGCGTCCGCGGAGTGAAAACTGCCACCCTAACAAGCTAC TGATCCTCAAGTGCCTTCGCTATCGCTTCAAGAAGCATTGC AAGTTGTCGTCCACGTGGCACTGGACTTGCCACGACGGCA AGCACAAGTGGCACTGGACGTGCCACGACGGCAAGCACAA GAACGCGATAGTGACGCTTACCTATGATCACATAGATTATTG GAAAGCGATCCGGCAGGAGAATGCGATATTCTTCGCTGCTA GACACCAGGTGGTGCCCGCGTTGAATATCTGCAAGGCGAA GGCCTGCAAGGCCATAGAGTGGAACACAGAGCCGAAGCAC TGCTTTAAGAAAGGCGGTCAGCACATCGAGGTCTGGTTCGA CTATGTGGCCTGGGACTCGGTCTACTATTGCGGCGACGACG GTTGGTGCAAGACCGAGGCCGAGAAATACGGCTGCAAAGG GACGTGGGAAGTTCACTTCGGGAACTCCATCGATTGCAACG ACTCCATGTGCAGCACGTTTGACGATAACGTGTCTGCCACG GAGTTGGTAAAGATGGCCCGATTCGAAGATCCCACAAGAA GACCCTACAAGCTGCCCGACCTGTGCACCGAGCTGAACAC AAGCCTCCAAGACATCGAGATTACCTGCGTGTACTGCAAGA CCGTGCTGGAGCTGACCGAGGTGTTCGAGTTCGCCTTCAAG GACCTGTTCGTGGTGTACAGAGACAGCATCCCACACGCCGC CTGCCACAAGTGCATCGACTTCTACAGCCGGATTCGGAAC TGCGGTACTACAGCGACAGCGTGATGTATGGGCCCAAGGCC ACCCTGCAAGACATCGTGCTGCACCTGGAGCCTCAGAACG AAATACCCGTGACCTGCTGTGCCATGAGCAACTGAGCGAC AGCGAGGAAGAGAATGATGAGATCGACGGCGTGAATCATC AGCACCTGCCCGCTAGAAGGGCCGAGCCACAACGGCACAC CATGCTGTGCATGTGCTTCTACAGCAGAATCAGAGAACTCC GGTATTACAGCGACTCCGTGTACGGAGATACCCTCGAGAAG CTGACCAACACCGGCCTGTACAATCTGCTGATCAGATGTCT GAGATGTCAGAAACCCTTAAATCCCGCCGAGAAGCTGAGA CACCTGAACGAGAAGAGAAGATTCCACAAGATCGCCGGCC ACTACAGAGGGCAGTGCCACAGCTGCTGCAACAGAGCTAG ACAAGAGAGACTGCAGAGAAGACGGGAGACCCAAGTGGC TAGAAGGGCTGAGCCGAAAGACATACCATGCTGTGTATGT GCTGCAAATGCGAGGCTAGAATCGAGCTGGTGGTGGAGAG CAGCGCCGACGACCTGAGAGCCTTTCAGCAGCTGTTCCTG AGCACCCTGAGCTTCGTGTGTCCCTGGTGCGCTAGCCAACA GATGCATCAGAAGAGAACCGCCATGTTCCAAGATCCGCAAG AGAGACCTAGAAAACTCCCTCATCTGTGCACCGAACTGCA GACCACCATCCACGACATCATCCTGGAGTGCGTGTATTGCA AACAACAGCTGCTGAGAAGAGAGGTGTACGACTTCGCCTTT CAGAGACCTGTGCATCGTGTACCGGGACGGCAATCCCTACG CCGTGTGCGACAAGTGCCTCAAGTTCTATAGCAAGATCAGC GAGTATAGATACATGCACGGAGATACGCCGACCCTGCACGA GTACATGCTGGACCTGCAGCCCGAGACCACCGACCTGTACT GCTACGAGCAGCTGAACGACAGCAGCGAAGAGGAGGACG AGATTGACGGCCCGGCCGGCCAAGCCGAGCCCGACAGAGC CCACTACAACATCGTGACCTTCTGCTGTAAATGCGATAGCA CACTGGACAAGTGCCTGAAGTTCTACAGCAAGATTAGCGA GTACAGATATTACTGCTACTCCGTGTACGGGACAACCCTGG AGCAGCAGTACAACAAGCCTCTGTGCGACCTGCTGATCCG GTGTATTAACTGTCAGAAGCCCTTGTGTCCCGAGGAGAAGC AGAGACACCTGGACAAGAAGCAGAGATTCCACAACATCAG |

```
                              Sequence listing
─────────────────────────────────────────────────────────────────────
SEQ ID
NO.       name         sequence
─────────────────────────────────────────────────────────────────────
                       AGGCAGATGGACCGGCAGATGCATGAGCTGCTGCAGAAGC
                       AGCAGAACAAGAAGAGAGACACAACTGCACTACAATATCG
                       TCACCTTCTGCTGCAAGTGCGACTCCACACTGCGGCTCTGC
                       GTGCAGAGCACCCACGTGGACATCAGAACCCTGGAGGACC
                       TGCTGATGGGCACCCTGGGCATCGTGTGTCCCATCTGCAGC
                       CAAAAGCCCTGATGA
─────────────────────────────────────────────────────────────────────
```

The invention claimed is:

1. A polynucleotide molecule, comprising at least a coding sequence of an HPV antigen polypeptide, the antigen polypeptide sequentially from the N-terminus to the C-terminus comprises at least:
an amino acid sequence C, an amino acid sequence B, and an amino acid sequence A;
wherein,
the amino acid sequence A sequentially from the N-terminus to the C-terminus comprises at least SEQ ID NOs: 1-4, and each of the amino acid sequences represented by the SEQ ID NOs is connected directly and sequentially or by a linker sequentially;
the amino acid sequence B sequentially from the N-terminus to the C-terminus comprises at least SEQ ID NOs: 5-8, and each of the amino acid sequences represented by the SEQ ID NOs is connected directly and sequentially or by a linker sequentially; and
the amino acid sequence C comprises an HPV E2 antigen sequence.

2. The polynucleotide molecule according to claim 1, wherein the HPV E2 antigen sequence is SEQ ID NO: 9.

3. The polynucleotide molecule according to claim 1, wherein the HPV antigen polypeptide comprises SEQ ID NO: 16, or an amino acid sequence having at least 99%, 98%, 97%, 96%, 95%, 90%, 85%, or 80% sequence identity with SEQ ID NO: 16.

4. The polynucleotide molecule according to claim 1, further comprising an encoding sequence of an immune stimulating factor Flt3L or a functional domain thereof at the 5' end of the coding sequence of the HPV antigen polypeptide;
wherein the polypeptide sequence of the immune stimulating factor Flt3L comprises at least an amino acid sequence represented by SEQ ID NO: 10, or an amino acid sequence having at least 99%, 98%, 97%, 96%, 95%, 90%, 85%, or 80% sequence identity with SEQ ID NO: 10.

5. The polynucleotide molecule according to claim 1, further comprising a coding sequence of a secretory signal peptide tPA-SP;
wherein the secretory signal peptide tPA-SP comprises the amino acid sequence represented by SEQ ID NO: 11, or an amino acid sequence having at least 99%, 98%, 97%, 96%, 95%, 90%, 85%, or 80% sequence identity with SEQ ID NO: 11.

6. The polynucleotide molecule according to claim 1, comprising coding sequences of a secretory signal peptide, an immune stimulating factor, and HPV antigen polypeptide which are sequentially connected from the 5' end to the 3' end.

7. The polynucleotide molecule according to claim 6, wherein the amino acid sequence of the secretory signal peptide, immune stimulating factor, and HPV antigen polypeptide comprises SEQ ID NO: 21, or an amino acid sequence having at least 99%, 98%, 97%, 96%, 95%, 90%, 85%, or 80% sequence identity with SEQ ID NO: 21.

8. The polynucleotide molecule according to claim 1, comprising any one polynucleotide sequence selected from SEQ ID NO: 46 or 54 or consisting of any one polynucleotide sequence selected from SEQ ID NO: 46 or 54, or encoded by any one polynucleotide sequence selected from SEQ ID NO: 46 or 54.

9. The polynucleotide molecule according to claim 1, wherein the polynucleotide molecule is an mRNA molecule, comprising a 5' cap structure, 5'UTR structure, 3'UTR structure and/or poly (A) tail.

10. The polynucleotide molecule according to claim 9, wherein the 5'UTR structure comprises at least a polynucleotide sequence represented by SEQ ID NO: 25, or a polynucleotide sequence having at least 99%, 98%, 97%, 96%, 95%, 90%, 85%, or 80% sequence identity with SEQ ID NO: 25.

11. The polynucleotide molecule according to claim 9, wherein the 3'UTR structure comprises at least a polynucleotide sequence represented by SEQ ID NO: 26, or a polynucleotide sequence having at least 99%, 98%, 97%, 96%, 95%, 90%, 85%, or 80% sequence identity with SEQ ID NO: 26.

12. The polynucleotide molecule according to claim 9, wherein part or all of the uridines in the mRNA molecule are chemically modified uridines.

13. The polynucleotide molecule according to claim 9, wherein the poly (A) tail comprises at least a polynucleotide sequence represented by SEQ ID NO: 27, or a polynucleotide sequence having at least 99%, 98%, 97%, 96%, 95%, 90%, 85%, or 80% sequence identity with SEQ ID NO: 27.

14. A fusion polypeptide, which is encoded by the polynucleotide molecule according to claim 1.

15. The fusion polypeptide according to claim 14, comprising an amino acid sequence represented by SEQ ID NO: 16 or SEQ ID NO: 21, or an amino acid sequence having at least 99%, 98%, 97%, 96%, 95%, 90%, 85%, or 80% sequence identity with the amino acid sequence represented by SEQ ID NO: 16 or SEQ ID NO: 21.

16. A delivery system, comprising the polynucleotide molecule according to claim 1.

17. The delivery system according to claim 16, wherein the delivery system is a lipid nanoparticle (LNP), wherein the LNP comprises ionizable lipid, phospholipid, cholesterol, and polyethylene glycol (PEG)-lipid.

18. A pharmaceutical composition, comprising the polynucleotide molecule according to claim 1.

19. The pharmaceutical composition according to claim 18, further comprising an immune stimulating factor and/or an adjuvant or a nucleic acid molecule encoding the immune stimulating factor and/or an adjuvant, wherein the immune stimulating factor is any one or more selected from the group consisting of: IL-3, IL-7, IL-2, IL-4, IL-5, IL-12, IL-13, Flt3L, G-CSF, M-CSF, GM-CSF, EPO, TPO, SCF, IFNα-2a, IFNα-2β, Pre IFNα-2β, MIP-α, STING, HSP70, and an immune checkpoint inhibitor.

20. The pharmaceutical composition according to claim 19, wherein the immune checkpoint inhibitor is a PD-1 inhibitor or a PD-L1 inhibitor.

21. A method for treating or inducing an immune response against HPV infection or a HPV infection related disease, comprising administration of the polynucleotide molecule according to claim 1 to an individual.

22. The method according to claim 21, wherein the HPV infection related disease is cervical cancer.

23. The method according to claim 22, wherein the administration is intratumoral injection, peri-lymph nodes injection, or intramuscular injection.

24. The method according to claim 23, further comprising administration of immune stimulating factor or a nucleic acid molecule encoding the immune stimulating factor, chemotherapy, radiation therapy, and/or targeted therapy to an individual; wherein the immune stimulating factor is one or more selected from the group consisting of: IL-3, IL-7, IL-2, IL-4, IL-5, IL-12, IL-13, F13L, G-CSF, M-CSF, GM-CSF, EPO, TPO, SCF, IFNα-2α, IFNα-2β, Pre IFNα-2β, MIP-α, STING, HSP70, and an immune checkpoint inhibitor.

25. The method according to claim 24, wherein the immune checkpoint inhibitor is a PD-1 inhibitor or a PD-L1 inhibitor.

* * * * *